United States Patent
Tuaillon et al.

(10) Patent No.: US 9,737,599 B2
(45) Date of Patent: Aug. 22, 2017

(54) COMBINATION OF FCγRIIB-SPECIFIC ANTIBODIES AND CD20-SPECIFIC ANTIBODIES AND METHODS OF USE THEREOF

(71) Applicant: MacroGenics, Inc., Rockville, MD (US)

(72) Inventors: Nadine Tuaillon, Gettysburg, PA (US); Christopher Rankin, Cabin John, MD (US)

(73) Assignee: MacroGenics, Inc., Rockville, MD (US)

( * ) Notice: Subject to any disclaimer, the term of this patent is extended or adjusted under 35 U.S.C. 154(b) by 412 days.

(21) Appl. No.: 14/295,579

(22) Filed: Jun. 4, 2014

(65) Prior Publication Data

US 2014/0328843 A1 Nov. 6, 2014

Related U.S. Application Data

(60) Division of application No. 12/342,305, filed on Dec. 23, 2008, now Pat. No. 8,778,339, which is a continuation-in-part of application No. PCT/US2007/072151, filed on Jun. 26, 2007.

(60) Provisional application No. 60/816,772, filed on Jun. 26, 2006.

(51) Int. Cl.
| | |
|---|---|
| *A61K 39/40* | (2006.01) |
| *A61K 39/42* | (2006.01) |
| *A61K 39/395* | (2006.01) |
| *C07K 16/28* | (2006.01) |
| *G01N 33/543* | (2006.01) |
| *G01N 33/564* | (2006.01) |
| *G01N 33/574* | (2006.01) |
| *A61K 45/06* | (2006.01) |
| *C07K 16/00* | (2006.01) |
| *A61K 39/00* | (2006.01) |

(52) U.S. Cl.
CPC ........ *A61K 39/39558* (2013.01); *A61K 45/06* (2013.01); *C07K 16/283* (2013.01); *C07K 16/2887* (2013.01); *G01N 33/54393* (2013.01); *G01N 33/564* (2013.01); *G01N 33/574* (2013.01); *G01N 33/57426* (2013.01); *A61K 2039/507* (2013.01); *C07K 2317/24* (2013.01); *C07K 2317/52* (2013.01); *C07K 2317/56* (2013.01); *C07K 2317/565* (2013.01); *C07K 2317/72* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,752,601 A | 6/1988 | Hahn |
| 5,024,835 A | 6/1991 | Rao et al. |
| 5,225,539 A | 7/1993 | Winter |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,723,584 A | 3/1998 | Schatz |
| 5,736,135 A | 4/1998 | Goeddel et al. |
| 5,736,137 A | 4/1998 | Anderson et al. |
| 5,837,243 A | 11/1998 | Deo et al. |
| 5,874,239 A | 2/1999 | Schatz |
| 5,877,396 A | 3/1999 | Ravetch et al. |
| 5,888,533 A | 3/1999 | Dunn |
| 5,932,433 A | 8/1999 | Schatz |
| 5,945,115 A | 8/1999 | Dunn et al. |
| 5,985,599 A | 11/1999 | Mckenzie et al. |
| 6,019,968 A | 2/2000 | Platz et al. |
| 6,025,485 A | 2/2000 | Kamb et al. |
| 6,114,147 A | 9/2000 | Frenken et al. |
| 6,132,764 A | 10/2000 | Li et al. |
| 6,132,992 A | 10/2000 | Ledbetter et al. |

(Continued)

FOREIGN PATENT DOCUMENTS

| | | |
|---|---|---|
| EP | 0 327 378 | 8/1989 |
| EP | 0 332 865 | 9/1989 |

(Continued)

OTHER PUBLICATIONS

US 6,331,391, 12/2001, Wittrup et al. (withdrawn)

(Continued)

*Primary Examiner* — Chun Dahle
(74) *Attorney, Agent, or Firm* — William C. Schrot; AuerbachSchrot LLC

(57) ABSTRACT

The present invention relates to methods of treatment, prevention, management or amelioration of one or more symptoms of diseases or disorders associated with CD20 expression that encompass administration of a combination of: (A) one or more antibodies that specifically bind FcγRIIB, particularly human FcγRIIB, with greater affinity than said antibodies bind FcγRIIA, and (B) one or more antibodies that specifically bind to CD20. Such methods include methods of treating, preventing, managing or ameliorating one or more symptoms of a B cell related disease or disorder or an inflammatory disorder. The invention also provides pharmaceutical compositions comprising an anti-FcγRIIB antibody and an anti-CD20 antibody.

16 Claims, 16 Drawing Sheets

(56) References Cited

U.S. PATENT DOCUMENTS

| | | | |
|---|---|---|---|
| 6,165,745 A | 12/2000 | Ward et al. |
| 6,180,370 B1 | 1/2001 | Queen et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |
| 6,277,375 B1 | 8/2001 | Ward |
| 6,300,065 B1 | 10/2001 | Kieke et al. |
| 6,339,069 B1 | 1/2002 | Meers et al. |
| 6,420,149 B1 | 7/2002 | Fukuda et al. |
| 6,423,538 B1 | 7/2002 | Wittrup et al. |
| 6,455,263 B2 | 9/2002 | Payan |
| 6,472,511 B1 | 10/2002 | Leung et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,696,550 B2 | 2/2004 | Larosa et al. |
| 6,737,056 B1 | 5/2004 | Presta |
| 6,821,505 B2 | 11/2004 | Ward |
| 6,982,321 B2 | 1/2006 | Winter |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,425,619 B2 | 9/2008 | Koenig et al. |
| 7,425,620 B2 | 9/2008 | Koenig et al. |
| 7,632,497 B2 | 12/2009 | Stavenhagen |
| 7,655,229 B2 | 2/2010 | Chan et al. |
| 7,662,925 B2 | 2/2010 | Lazar et al. |
| 7,662,926 B2 | 2/2010 | Chan et al. |
| 7,786,270 B2 | 8/2010 | Johnson et al. |
| 2001/0036459 A1 | 11/2001 | Ravetch |
| 2002/0004587 A1 | 1/2002 | Miller et al. |
| 2002/0028486 A1 | 3/2002 | Morrison et al. |
| 2003/0077282 A1 | 4/2003 | Bigler et al. |
| 2003/0115614 A1 | 6/2003 | Kanda et al. |
| 2003/0158389 A1 | 8/2003 | Idusogie et al. |
| 2003/0190319 A1 | 10/2003 | Adolf et al. |
| 2003/0207346 A1 | 11/2003 | Arathoon et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0235065 A1 | 11/2004 | Hansen et al. |
| 2004/0236078 A1 | 11/2004 | Carter et al. |
| 2005/0025764 A1 | 2/2005 | Watkins et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0090648 A1 | 4/2005 | Tsurushita et al. |
| 2005/0215767 A1 | 9/2005 | Koenig et al. |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0177439 A1 | 8/2006 | Koenig et al. |
| 2007/0004909 A1 | 1/2007 | Johnson et al. |
| 2007/0036799 A1 | 2/2007 | Stavenhagen et al. |
| 2007/0253948 A1 | 11/2007 | Chan et al. |
| 2008/0044417 A1 | 2/2008 | Johnson et al. |
| 2008/0051563 A1 | 2/2008 | Lazar et al. |
| 2008/0131435 A1 | 6/2008 | Stavenhagen et al. |
| 2008/0138344 A1 | 6/2008 | Stavenhagen et al. |
| 2008/0286819 A1 | 11/2008 | Ravetch et al. |
| 2009/0053218 A1 | 2/2009 | Koenig et al. |

FOREIGN PATENT DOCUMENTS

| | | |
|---|---|---|
| EP | 0 629 703 | 12/1994 |
| EP | 0 359 096 | 11/1997 |
| EP | 0 953 639 | 11/1999 |
| EP | 1 006 183 | 6/2000 |
| EP | 0 343 950 | 10/2000 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/19362 | 4/1999 |
| WO | WO 99/41285 | 8/1999 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | WO 01/79299 | 10/2001 |
| WO | WO 02/02781 | 1/2002 |
| WO | WO 02/060919 | 8/2002 |
| WO | WO 02/086070 | 10/2002 |
| WO | WO 03/035835 | 5/2003 |
| WO | WO 03/066095 | 8/2003 |
| WO | WO 03/074679 | 9/2003 |
| WO | WO 2004/016750 | 2/2004 |
| WO | WO 2004/029207 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2005/018669 | 3/2005 |
| WO | WO 2005/070963 | 8/2005 |
| WO | WO 2005/110474 | 11/2005 |
| WO | WO 2005/115452 | 12/2005 |
| WO | WO 2006/020114 | 2/2006 |
| WO | WO 2006/028956 | 3/2006 |
| WO | WO 2006/066078 | 6/2006 |
| WO | WO 2006/088494 | 8/2006 |
| WO | WO 2006/113665 | 10/2006 |
| WO | WO 2007/021841 | 2/2007 |
| WO | WO 2007/024249 | 3/2007 |
| WO | WO 2007/106707 | 9/2007 |
| WO | WO 2008/002933 | 1/2008 |
| WO | WO 2008/009545 | 1/2008 |
| WO | WO 2008/019199 | 2/2008 |
| WO | WO 2009/083009 | 7/2009 |
| WO | WO 2009/151717 | 9/2009 |

OTHER PUBLICATIONS

Abra et al. The next generation of liposome delivery systems: recent experience with tumor-targeted, sterically-stabilized immunoliposomes and active-loading gradients. J Liposome Res. Feb.-May 2002;12(1-2):1-3.

Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.

Altman et al., "Phenotypic Analysis of Antigen-Specific T Lymphocytes", Science 274:94-96, 1996.

Amit et al. (1986) Three-dimensional structure of an antigen-antibody complex at 2.8 A resolution.; Science 233:747-753.

Angal et al., "A single amino acid substitution abolishes the heterogeneity of chimeric mouse/human (IgG4) antibody," Mol Immunol 30 :105-108, 1993.

Armour et al., "The contrasting IgG-binding interactions of human and herpes simplex virus Fc receptors," Biochemical Society Transactions 30:495-500, 2002.

Armour et al., "Recombinant human IgG molecules lacking Fcgamma receptor I binding and monocyte triggering activities," Eur J Immunol 29:2613-2624, 1999.

Armour et al., "Differential binding to human FcgammaRIIa and FcgammaRIIb receptors by human IgG wildtype and mutant antibodies," Mol Immunol 40 :585-593, 2003.

(56) References Cited

OTHER PUBLICATIONS

Armstrong, S. et al. "Heterogeneity of IgG1 monoclonal anti-Rh(D): an investigation using ADCC and macrophage binding assays," Brit. J. Haematol. 66:257-262 (1987).
Bachmann et al. (2005) "Recall Proliferation of Memory CD8+ T Cells and Antiviral Protection," J. Immunol. 175:4677-4685.
Baggiolini M, Dewald B. "Cellular models for the detection and evaluation of drugs that modulate human phagocyte activity," Experientia. Oct. 15;44(10):841-848, 1988.
Bendas G, Immunoliposomes: a promising approach to targeting cancer therapy. BioDrugs. 2001;15(4):215-24.
Bendig, M.M. (1995) Methods: A Companion to Methods in Enzymology 8:83-93.
Bernard et al. (1986) "A unique epitope on the CD2 molecule defined by the monoclonal antibody 9-1: epitope-specific modulation of the E-rosette receptor and effects on T-cell functions," Hum. Immunol. 17(4):388-405.
Bewarder et al., 1996, "In vivo and in vitro specificity of protein tyrosine kinases for immunoglobulin G receptor (FcgammaRII) phosphorylation," Mol. Cell. Biol. 16 (9):4735-43.
Billadeau et al., ITAMs versus ITIMs: striking a balance during cell regulation, J Clin Invest. Jan. 2002;109(2):161-8.
Boder and Wittrup, 1997, "Yeast surface display for screening combinatorial polypeptide libraries", Nature Biotechnology 15:553-557.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder et al., "Directed evolution of antibody fragments with monovalent femtomolar antigen-binding affinity," Proc. Natl. Acad. Sci. USA 97:10701-10705, 2000.
Bolland et al., Genetic modifiers of systemic lupus erythematosus in Fc.gamma.RIIB(-/-) mice. J Exp Med. May 6, 2002;195(9):1167-74.
Bolland and Ravetch., Inhibitory pathways triggered by ITIM-containing receptors. Adv Immunol. 1999;72:149-177.
Boruchov et al. (2005) Activating and inhibitory IgG Fc receptors on human DCs mediate opposing functions. The Journal of Clinical Investigation 115(10):2914-2923.
Boruchov et al., "Expression and Modulation of the Inhibitory Fcγ Receptor, FcγRIIB (CD32B), on Human Dendritic Cells (DCs)," Blood 102(11):Abstract #1908, 2003.
Boyer et al. (1999) "Relative cytotoxic activity of immunotoxins reactive with different epitopes on the extracellular domain of the c-erbB-2 (HER-2/neu) gene product p185," Int. J. Cancer. 82(4):525-531.
Brauweiler et al., Partially distinct molecular mechanisms mediate inhibitory Fc.gamma.RIIB signaling in resting and activated B cells. J Immunol. 2001;167:204-211.
Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brown (2001) "Factors Modifying the Migration of Lymphocytes Across the Blood-Brain Barrier," Int Immunopharmacol. Nov. 2001;1(12):2043-62.
Brown EJ., "In Vitro Assays of Phagocytic Function of Human Peripheral Blood Leukocytes: Receptor Modulation and Signal Transduction," vol. 45 (Microbes as Tools for Cell Biology) in *Methods in Cell Biololgy*, Russell ed. Academic Press Inc. pp. 147-164, 1994.
Budde et al., Specificity of CD32 mAB for Fc.gamma.RIIa, Fc.gamma.RIIb1, and Fc.gamma.RIIb2 expressed in transfected mouse B cells and BHK-21 cells. Leukocyte Typing V: White cell differentiation antigens. 1995;828-832 (Schlossman, Boumsell, Gilks, Harlan, Kishomoto, eds.).
Burgess et al. (1990) "Possible dissociation of the heparin-binding and mitogenic activities of the heparin-binding (acidic fibroblast) growth factor-1 from its receptor binding activities by site directed mutagenesis of a single lysine residue," J. Cell Biol. 111:2129-2138.
Burlmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Callanan et al., The IgG Fc Receptor, Fc.gamma.RIIB is a target for deregulation by chromosomal translocation in malignant lymphoma. PNAS. Jan. 2000;97(1):309-314.
Canfield and Morrison, "The binding affinity of human IgG for its high affinity Fc receptor is determined by multiple amino acids in the CH2 domain and is modulated by the hinge region," J Exp Med 173:1483-1491, 1991.
Campbell et al. (2003) "Monoclonal antibody therapy for lymphoma," Blood Rev. 17(3):143-152.
Cameron et al., Differentiation of the human monocyte cell line, U937, with dibutyryl cyclicAMP induces the expression of the inhibitory Fc receptor, Fc.gamma.RIIb. Immunol Lett. Oct. 1, 2002;83(3):171-9.
Camilleri-Broet et al., Fc.gamma.RIIB is differentially expressed during B cell maturation and in B-cell lymphomas. Br J Haematol. 2004;124(1):55-62.
Caron et al., "Engineered humanized dimeric forms of IgG are more effective antibodies," J Exp Med 176 :1191-5, 1992.
Carter et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Cassard et al., Modulation of tumor growth by inhibitory Fc.gamma. receptor expressed by human melanoma cells. The J Clin Invest. Nov. 2002;110(10):1549-1557.
Casset et al. (2003) A peptide mimetic of an anti-CD4 monoclonal antibody by rational design, Biochem. Biophs. Res. Commun. 307:198-205.
Cavacini et al. (1995) "Influence of heavy chain constant regions on antigen binding and HIV-1 neutralization by a human monoclonal antibody," J Immunol. 155(7):3638-3644.
Chappel et al., "Identification of the Fc gamma receptor class I binding site in human IgG through the use of recombinant IgG1/IgG2 hybrid and point-mutated antibodies," Proc. Natl. Acad. Sci USA 88:9036-9040, 1991.
Chappel et al., "Identification of a secondary Fc gamma RI binding site within a genetically engineered human IgG antibody," J Biol. Chem 268:25124-25131, 1993.
Chattergee et al. (1994) "Idiotypic Antibody Immunotherapy of Cancer," Cancer Immuno. Immunother. 38:75-82.
Chen, et al. (1999) "Selection and Analysis of an Optimized Anti-VEGF Antibody: Crystal Structure of an Affinity-Matured Fab in Complex with Antigen," J. Molec. Biol. 293:865-881.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Modulation of immune complex-induced inflammation in vivo by the coordinate expression of activation and inhibitory Fe receptors," J Exp Med 189:179-185, 1999.
Clynes et al., "Inhibitory Fc receptors modulate in vivo cytoxicity against tumor targets," Nature Medicine 6 :443-446, 2000.
Clynes et al., "Fe receptors are required in passive and active immunity to melanoma," Proc. Natl. Acad. Sci USA 95:652-656, 1998.

(56) References Cited

OTHER PUBLICATIONS

Clynes et al., "Uncoupling of immune complex formation and kidney damage in autoimmune glomerulonephritis," Science 279:1052-1054, 1998.
Colman, P.M. (1994) "Effects of amino acid sequence changes on antibody-antigen interactions," Res. Immunol. 145:33-36.
Daeron et al., The Same Tyrosine Based Inhibition Motif, in the Intracytoplasmic Domain of Fc.gamma.RIIB, regulates negatively BCR, TCR- and FcR dependent cell activation. Immunity. Nov. 1995;3: 635-646.
Damle et al., B-cell chronic lymphocytic leukemia cells express a surface membrane phenotype of activated, antigen-experienced B lymphocytes. Blood Jun. 1, 2002;99(11):4087-4093.
Davies et al., Expression of GnTIII in a recombinant anti-CD20 CHO production cell line: Expression of antibodies with altered glycoforms leads to an increase in ADCC through higher affinity for FC.sub..gamma. RIII. Biotechnol Bioeng. Aug. 20, 2001;74(4):288-94.
Davies et al. (1995) Antibody VH domains as small recognition units, Bio/Technology 13:475-479.
de Haas, Wien Kin "IgG-Fc receptors and the clinical relevance of their polymorphisms," Wien Klin Wochenscha 113:825-831, 2001.
Deisenhofer, "Crystallographic refinement and atomic models of a human Fc fragment and its complex with fragment B of protein A from Staphylococcus aureus at 2.9- and 2.8-A resolution," Biochem. 20:2361-2370, 1981.
Deo et al., "Clinical significance of IgG Fc receptors and Fc gamma R-directed immunotherapies," Immunology Today 18:127-135, 1997.
DePascalis et al. (2002) "Grafting of Abbreviated Complementarity Determining Regions Containing Specificity Determining Residues Essential for Ligand Contact to Engineer a Less Immunogenic humanized monoclonal antibody," J. Immunol. 169:3076-3084.
De Santes et al. (1992) "Radiolabeled Antibody Targeting of the Her-2/neu Oncoprotein," Cancer Res. 52:1916-1923.
Dermer (1994) "Another Anniversary for the War on Cancer," Biotechnology 12:320 (1994).
Ding et al., Inhibition of the function of the Fc.gamma.RIIB by a monoclonal antibody to thymic shared antigen-1, a Ly-6 family antigen. Immunology. Sep. 2001;104(1):28-36.
Dumoulin et al. (2002) Single-domain antibody fragments with high conformational stability, Protein Science 11:500-512.
Duncan and Winter, "The binding site for C1q on IgG," Nature 332 :738-740, 1988.
Duncan and Winter, "Localization of the binding site for the human high-affinity Fc receptor on IgG," Nature 332:563-564, 1988.
Edberg et al., "Modulation of Fcgamma and Complement Receptor Function by the Glycosyl-Phosphatidylinositol-Anchored Form of FcgammaRIII," Journal of Immunology 152: 5826-5835, 1994.
Efferson et al. (2005) "Stimulation of Human T Cells by an Influenza A Vector Expressing a CTL Epitope from the HER-2/neu Protooncogene Results in Higher Numbers of Antigen Specific TCRhi Cells than Stimulation with Peptide," Anticancer Research 25:715-724.
Ellman, J. et al. "Biosynthetic Method for Introducing Unnatural Amino Acids Site-Specifically into Proteins," Methods Enzymol. 202:301-336, 1991.
Eppstein et al., Biological activity of liposome-encapsulated murine interferon .gamma. is mediated by a cell membrane receptor. Proc Natl Acad Sci U S A. Jan. 1985;82(11):3688-9.
Fanger et al., Production and use of anti-FcR bispecific antibodies. Immunomethods. Feb. 1994;4(1):72-81.
Farag, et al., Fc.gamma.RIIIa and Fc.gamma.RIIIa polymorphisms do not predict response to Rituximab in B-cell chronic lymphocytic leukemia. Blood. Oct. 16, 2003 (15 pp.).
Flesch and Neppert, "Functions of the Fe receptors for immunoglobulin G," J Clin Lab Anal 14:141-156, 2000.
Fidler, I. J., Macrophages and metastasis—a biological approach to cancer therapy. Cancer Res. Oct. 1985;45(10):4714-26.

Fleit et al., 1995 "Cross-linking of mAb to Fc.gamma.RII results in tyrosine phosphorylation of multiple polypeptides including FC.gamma.RII itself." Leukocyte Typing V: White cell differentiation antigens 826-827 (Schlossman, Boumsell, Gilks, Harlan, Kishomoto, eds.).
Gamberale et al., 2003, "To the Editor: Expression of Fc.gamma. receptors type II (Fc.gamma.RII) in chronic lymphocytic leukemia B cells." Blood (Correspondence) 102(7):2698-2699.
Gerber et al., Stimulatory and inhibitory signals originating from the macrophage Fc.gamma. receptors. Microbes Infect. Feb. 2001;3(2):131-9.
Gergeley et al., "Fe receptors on lymphocytes and K cells," Biochemical Society Transactions 12:739-743, 1984.
Gergely and Sarmay, "The two binding-site models of human IgG binding Fc gamma receptors," FASEB J 4:3275-3283, 1990.
Greenwood and Clark, Effector functions of matched sets of recombinant human IgG subclass antibodies. (final version edited Feb. 11, 1993).
Greenwood et al., "Structural motifs involved in human IgG antibody effector functions," Eur J Immunol 23:1098-1104, 1993.
Greenwood et al., "Engineering multiple-domain forms of the therapeutic antibody CAMPATH-1H: effects on complement lysis," Therapeutic Immunology 1:247-255, 1994.
Gura (1997) "Systems for Identifying New Drugs are Often Faulty," Science 278:1041-1042.
Hadley et al., "The functional activity of Fc gamma RII and Fc gamma RIII on subsets of human lymphocytes," Immunology 76:446-451, 1992.
Hatta et al., "Association of Fe gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Henry et al. (2004) "A prostate-specific membrane antigen-targeted monoclonal antibody-chemotherapeutic conjugate designed for the treatment of prostate cancer," Cancer Res. 64(21):7995-8001.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide/MHC," Proc. Natl. Acad. Sci. U.S.A. 97 :5387-92, 2000.
Holm et al, (2007) "Functional Mapping and Single Chain Construction of the Anti-Cytokeratin 8 Monoclonal Antibody TS1," Molecular Immunology 44:1075-1084.
Holmes et al., Alleles of the Ly-17 alloantigen define polymorphisms of the murine IgG Fc receptor. Proc Natl Acad Sci USA. Nov. 1985;82(22):7706-10.
Holt, L.J. (2003) "Domain Antibodies: Proteins for Therapy," TRENDS in Biochemistry 21(11)484-490.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Hulett et al., "Chimeric Fc receptors identify functional domains of the murine high affinity receptor for IgG," J Immunol 147 :1863-1868, 1991.
Hwang et al., Hepatic uptake and degradation of unilamellar sphingomyelin/cholesterol liposomes: a kinetic study. Proc Natl Acad Sci U S A. Jul. 1980;77(7):4030-4.
Ibragimova et al. (1999) "Stability of the beta-sheet of the WW domain: A molecular dynamics simulation study," Biophys. J. 77(4):2191-2198.
Idusogie et al., "Mapping of the C1q binding site on rituxan, a chimeric antibody with a human IgG1 Fc," J Immunol 164: 4178-4184, 2000.

(56) References Cited

OTHER PUBLICATIONS

Idusogie et al., "Engineered antibodies with increased activity to recruit complement," J Immunol 166 :2571-2575, 2001.
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jain et al. "Barriers to Drug Delivery in Solid Tumors," Scientific American Jul. 1994:58-65.
Jassal et al., "Remodeling glycans on IgG by genetic re-engineering," Biochem Soc Trans 26 :S113, 1998.
Jefferis and Lund, "Interaction sites on human IgG-Fc for FcgammaR: current models," Immunology Letters 82 :57-65, 2002.
Jefferis et al., "Recognition sites on human IgG for Fc gamma receptors: the role of glycosylation," Immunol Lett 44 :111-7, 1995.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jendeberg et al., "Engineering of Fc(1) and Fc(3) from human immunoglobulin G to analyse subclass specificity for *staphylococcal* protein A," J Immunological Methods 201 :25-34, 1997.
Jiang et al. (Epub Nov. 9, 2004) "A novel peptide isolated from a phage display peptide library with trastuzumab can mimic antigen epitope of HER-2," J Biol Chem. 280(6):4656-4662.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kadar et al., "Modulatory effect of synthetic human IgG Fc peptides on the in vitro immune response of murine spleen cells," Int J Immunpharmaeol 13 :1147-55, 1991.
Kagari et al., Essential Role of Fc.gamma. Receptors in anti-type II collagen antibody induced arthritis. J. Immunol. Apr. 2003;170:4318-24.
Kang, C.Y. et al. (1988) "Inhibition of Self-Binding Antibodies (Autobodies) by a VH-Derived Peptide," Science 240(4855):1034-1036.
Kato et al., "Structural basis of the interaction between IgG and Fcγ receptors," J Mol Biol 295:213-224, 2000.
Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.
Kepley et al. (2004) "Co-aggregation of FcgammaRII with FcepsilonRI on human mast cells inhibits antigeninduced secretion and involves SHIP-Grb2-Dok complexes" J. Biol. Chem. 279(34) 35139-35149.
Kieke et al., "Selection of functional T cell receptor mutants from a yeast surface-display library," Proc. Natl. Acad. Sci. U.S.A. 96 :5651-56, 1999.
Kim et al., "Analysis of FcγRIII and IgG Fc polymorphism reveals functional and evolutionary implications of protein-protein interaction," J Mol Evol 53:1-9, 2001.
Kim et al. (2002) "Both the epitope specificity and isotype are important in the antitumor effect of monoclonal antibodies against Her-2/neu antigen," Int. J. Cancer. 102(4):428-434.
Kimura et al. (1981) "A new mouse cell-surface antigen (Ly-m20) controlled by a gene linked to Mls locus and defined by monoclonal antibodies," Immunogenetics. 14(1-2):3-14.
Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V/F polymorphism influences the binding of IgG by natural killer cell Fc gammaRIIIa, independently of the Fc gammaRIIIa-48L/R/H phenotype," Blood 90 :1109-1114, 1997.
Kranz et al., "Mechanisms of ligand binding by monoclonal antifluorescyl antibodies," J. Biol. Chem. 257:6987-6995, 1982.
Kumpel, B.M. Brit. "Human monoclonal anti-D antibodies," J. Haematol. 71:415-420 (1989).
Kurlander et al., 1986, "Comparison of intravenous gamma globulin and a monoclonal anti-Fc receptor antibody as inhibitors of immune clearance in vivo in mice." J. Clin. Invest. 77(6):2010-2018.
Lazar et al. (1988) Transforming growth factor a: mutation of aspartic acid 47 and leucine 48 results in different biological activities, Molec. Cell. Biol. 8:1247-1252.
Le Gall, F. et al. (Epub May 4, 2004) "Effect of Linker Sequences Between the Antibody Variable Domains on the Formation, Stability and Biological Activity of a Bispecific Tandem Diabody," Protein Eng Des Sel. 17(4):357-366.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Lewis et al. (1993) "Differential responses of human tumor cell lines to anti-p185HER2 monoclonal antibodies," Cancer Immunol Immunother. 37(4):255-263.
Li et al. (2007) Regeneration of nigrostriatal dopaminergic axons by degradation of chondroitin sulfate is accompanied by elimination of the fibrotic scar and glia limitans in the lesion site. J. Neurosci. Res. 85:636-547.
Li et al., "Reconstitution of human Fc gamma RIII cell type specificity in transgenic mice," J Exp Med 183 :1259-1263, 1996.
Lifely et al., Glycosylation and biological activity of CAMPATH-1H expressed in different cell lines and grown under different culture conditions. Glycobiology. Dec. 1995;5(8):813-22.
Lin et al., Colony-stimulating factor 1 promotes progression of mammary tumors to malignancy. J Exp Med. 2001;193(6):727-739.
Lin et al., The macrophage growth factor CSF-1 in mammary gland development and tumor progression. J Mammary Gland Biol Neoplasia. 2002;7(2):147-62.
Liu et al., "Production of a mouse-human chimeric monoclonal antibody to CD20 with potent Fc-dependent biologic activity," J. Immunol. 139:3521-3526, 1987.
Looney et al., 1986, "Human Monocytes and U(#& Cells Bear Two Distinct Fc Receptors for IgG." J. Immunol. 136(5):1641-1647.
Lu, D. et al. (2003) "Di-Diabody: A Novel Tetravalent Bispecific Antibody Molecule by Design," J. Immunol. Meth. 279:219-232.
Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.
Lund et al., "Oligosaccharide-protein interactions in IgG can modulate recognition by Fc gamma receptors," FASEB J 9 :115-119, 1995.
Lund et al., "Human Fc gamma RI and Fc gamma RII interact with distinct but overlapping sites on human IgG," J Immunol 147 :2657-62, 1991.
Lund et al., "Multiple interactions of IgG with its core oligosaccharide can modulate recognition by complement and human Fc gamma receptor I and influence the synthesis of its oligosaccharide chains," J Immunol 157 :4963-4969, 1996.
Lund et al., "Multiple binding sites on the CH2 domain of IgG for mouse Fc gamma R11," Molecular Immunology 29:53-59, 1992.

(56) References Cited

OTHER PUBLICATIONS

Lyden et al., The Fc receptor for IgG expressed in the villus endothelium of human placenta is Fc.gamma. RIIb2. J Immunol. Mar. 15, 2001;166(6):3882-9.

MacCallum et al. (1996) "Antibody-Antigen Interactions: Contact Analysis and Binding Site Topography," J. Molec. Biol. 262:732-745.

Malbec et al., Fcs receptor I-associated lyn-dependent phosphorylation of Fc.gamma. receptor IIB during negative regulation of mast cell activation. J Immunol. Feb. 15, 1998;160(4):1647-58.

Maenaka et al., "The human low affinity Fcgamma receptors IIa, IIb, and III bind IgG with fast kinetics and distinct thermodynamic properties," J Biol Chem 48 :44898-904, 2001.

Maresco et al.., 1999, "The SH2-Containing 5'-Inositol Phosphatase (SHIP) is Tyrosine Phosphorylated after Fc.gamma. Receptor Clustering in Monocytes." J. Immunol. 162:6458-6465.

Maruyama K, In vivo targeting by liposomes. Biol Pharm Bull. Jul. 2000;23(7):791-9.

Masui et al. (1986) "Mechanism of antitumor activity in mice for anti-epidermal growth factor receptor monoclonal antibodies with different isotypes.," Canc. Res. 46:5592-5598.

McDevitt et al. "An alpha-particle emitting antibody ([213Bi]J591) for radioimmunotherapy of prostate cancer.," Cancer Res. 60(21):6095-6100.

Melero et al. (1998) The frequent expansion of a subpopulation of B cells that express RF-associated cross-reactive idiotypes: evidence from analysis of a panel autoreactive monoclonal antibodies; Scand. J. Immunol. 48:152-158 1998.

Michaelsen et al., "One disulfide bond in front of the second heavy chain constant region is necessary and sufficient for effector functions of human IgG3 without a genetic hinge," Immunolgy 91 :9243-9247, 1994.

Metcalfe, Mast Cells, Physiol Rev. Oct. 1997;77(4):1033-79.

Micklem et al., Different isoforms of human FcRII distinguished by CDw32 antibodies. J Immunol. Mar. 1990;144:2295-2303.

Morgan et al., "The N-terminal end of the CH2 domain of chimeric human IgG1 anti-HLA-DR is necessary for C1q, Fc gamma RI and Fc gamma RIII binding," Immunology 86 :319-324, 1995.

Morrison et al., "Structural determinants of IgG structure," Immunologist 2 :119-124, 1994.

Munn et al., "Phagocytosis of tumor cells by human monocytes cultured in recombinant macrophage colony-stimulating factor," J Exp Med. 172(1):231-7, 1990.

Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.

Nakamura et al., Fc.gamma. receptor IIB-deficient mice develop Goodpasture's Syndrome upon immunization with Type IV collagen: a novel murine model for Autoimmune Glomerular Basement Membrane Disease. J. Exp. Med. Mar. 6, 2000;191(5):899-905.

Neuberger et al., "Recombinant antibodies possessing novel effector functions," Nature 312 :604-608, 1984.

Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

Noren, C.J. et al. "A General Method for Site-Specific Incorporation of Unnatural Amino Acids into Proteins," Science 244:182-188, 1989.

Norris et al., A naturally occurring mutation in Fc.gamma.RIIA: A Q to K.sup.127 change confers unique IgG binding properties to the R.sup.131 allelic form of the receptor. Blood. Jan. 15, 1998;91(2):656-662.

Nose and Leanderson, "Substitution of asparagine324 with aspartic acid in the Fc portion of mouse antibodies reduces their capacity for C1q binding," Eur J Immunol 19 :2179-81, 1989.

Okazaki et al., "Fucose depletion from human IgG1 oligosaccharide enhances binding enthalpy and association rate between IgG1 and FcgammaRIIIa," J Mol Biol 336 :1239-1249, 2004.

Orfao and Ruiz-Arguelles, "General concepts about cell sorting techniques," Clinical Biochem. 29:5-9, 1996.

Ott, V.L. et al. "FcgammaRIIB as a potential molecular target for intravenous gamma globulin therapy," J. Allergy Clin Immunol. Oct. 2001:S95-S98.

Ott et al., Downstream of Kinase, p62.sup.dok, Is a mediator of Fc.gamma.RIIB inhibition of Fc.epsilon.RI signaling. J. of Immunol. 2002;168:4430-9.

Panka et al. (1988) Variable region framework differences result in decreased or increased affinity of variant anti-digoxin antibodies. Proc. Natl. Acad. Sci. USA 85:30803084.

Pardridge et al., Blood-brain barrier drug targeting: The future of brain drug development. Molecular Interventions. 2003, 3;2:90-105. See particularly pp. 91-96.

Park YS, Tumor-directed targeting of liposomes. Biosci Rep. Apr. 2002;22(2):267-81.

Park et al., Immunoliposomes for cancer treatment. Adv Pharmacol. 1997;40:399-435.

Partridge et al., "The use of anti-IgG monoclonal antibodies in mapping the monocyte receptor site on IgG," Mol Immunol. 23(12):1365-72, 1986.

Paul, William E, (1993) "Fundamental Microbiology, 3 Ed." pf. 242, 292-296.

Pereira et al. (1998) Cardiolipin Binding a light Chain from Lupus-prone Mice; Biochem. 37:1460-1437.

Perussia "Human Natural Killer Cell Protocols" in *Methods Molecular Biology*. vol. 121 (Campbell et al. eds.) Humana Press Inc., Totowa, NJ. 179-92, 2000.

Pettersen et al. (1999) "CD47 Signals T Cell Death," J. Immunol. 162(12):7031-7040.

Pluckthun, A. et al. (1997) "New protein engineering approaches to multivalent and bispecific antibody fragments," Immunotechnology 3(2):83-105.

Polson, A.G. et al. (Epub Mar. 20, 2007) "Antibody-Drug Conjugates Targeted to CD79 for the Treatment of Non-Hodgkin Lymphoma," Blood. 110(2):616-623.

Press et al. (1988) "Ricin A-chain containing immunotoxins directed against different epitopes on the CD2 molecule differ in their ability to kill normal and malignant T cells," J. Immunol. 141(12):4410-4417.

Presta, L.G. et al. (2005) "Selection, Design and Engineering of Therapeutic Antibodies," J. Allergy Clin. Immunol. 116(4):731-736.

Presta LG, "Engineering antibodies for therapy," Curr Pharm Biotechnol. Sep. 2002;3(3):237-56.

Pricop et al., "Differential modulation of stimulatory and inhibitory Fc.gamma. receptors on human monocytes by Th1 and Th2 cytokines," J Immunol. Jan. 1, 2001;166(1):531-7.

Pulford et al., 1995 "M6.5: The immunocytochemical distribution of CD16, CD32, and CD64 antigens." Leukocyte Typing V: White cell differentiation antigens 817-821 (Schlossman, Boumsell, Gilks, Harlan, Kishomoto, eds.) pp. 817-821.

Pulford et al., A new monoclonal antibody (KB61) recognizing a novel antigen which is selectively expressed on a subpopulation of human B lymphocytes. Immunology. Jan. 1986;57(1):71-6.

Qin et al., Fc.gamma. receptor IIB on follicular dendritic cells regulates the B cell recall response. J Immunol. 2000;164:6268-6275.

Radaev and Sun, "Recognition of immunoglobulins by Fcgamma receptors," Molecular Immunology 38 :1073-1083, 2001.

Rankin, et al., "CD32B, the human inhibitory Fc-γ receptor IIB, as a target for monoclonal antibody therapy of B-cell lymphoma", Blood, American Society of Hematology, vol. 108, No. 7, pp. 2384-2391, Oct. 1, 2006.

Ravetch and Bolland, "IgG Fc receptors," Annu Rev Immunol 19:275-90, 2001.

Ravetch and Clynes, "Divergent roles for Fc receptors and complement in vivo," Annu Rev Immunol 16:421-432, 1998.

Ravetch and Kinet, "Fc receptors," Annu Rev Immunol 9:457-492, 1991.

(56) References Cited

OTHER PUBLICATIONS

Ravetech and Lanier, "Immune inhibitory receptors," Science 290:84-89, 2000.
Ravetch et al., Fc receptors: rubor redux. Cell. Aug. 26, 1994;78(4):553-60.
Redpath et al., "The influence of the hinge region length in binding of human IgG to human Fcgamma receptors," Hum Immunol 59 :720-727, 1998.
Reali et al., IgEs targeted on tumor cells: therapeutic activity and potential in the design of tumor vaccines. Cancer Res. 2001;61(14): 5517-22.
Reff et al., "Depletion of B cells in vivo by a chimeric mouse human monoclonal antibody to CD20," Blood 83:435-445, 1994.
Reff et al., "A review of modifications to recombinant antibodies: attempt to increase efficacy in oncology applications," Critical Reviews in Oncology/Hematology 40: 25-35; 2001.
Riechmann et al., "Reshaping human antibodies for therapy," Nature. 332(6162):323-7, 1988.
Riemer et al. (Epub Jan. 8, 2005) "Matching of trastuzumab (Herceptin) epitope mimics onto the surface of Her-2/neu—a new method of epitope definition.," Mol Immunol. 42(9):1121-1124.
Routledge et al., The effect of aglycosylation on the immunogenicity of a humanized therapeutic CD3 monoclonal antibody. Transplantation. Oct. 27, 1995;60(8):847-53.
Rudikoff et al. (1982) "Single amino acid substitution altering antigen-binding specificity" Proc. Natl. Acad. Sci. USA 79:1979-1983.
Samsom et al. (2005) Fc gamma RIIB regulates nasal and oral tolerance: a role for dendritic cells Immunol. 174:5279-5287.
Samuelsson et al., Anti-inflammatory activity of IVIG mediated through the inhibitory Fc receptor. Science. Jan. 19, 2001; 291:484-486.
Sarkar et al., Negative signaling via Fc.gamma.RIIB1 in B cells blocks phospholipase C.sub..gamma.2 tyrosine phosphorylation but not Syk or Lyn activation. J Biol Chem. Aug. 16, 1996;271(33):20182-6.
Sarmay et al., "The effect of synthetic peptides corresponding to Fc sequences in human IgG1 on various steps in the B cell activation pathway," Eur J Immunol 18 :289-294, 1988.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sautes-Fridman et al., "Fc gamma receptors: a magic link with the outside world," ASHI Quarterley, 4th Quarter:148-151, 2003.
Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in *Escherichia coli*," Bio/Technology 11:1138-1143, 2000.
Scholl et al., Is colony-stimulating factor-1 a key mediator of breast cancer invasion and metastasis? Mol Carcinog. 7(4):207-11.
Schuna et al., 2000, "New Drugs for the treatment of rheumatoid arthritis." Am J. Health Syst. Phar, 57:225-237.
Seaver (1994) "Monoclonal Antibodies in Industry: More Difficult than Originally Thought," Genetic Engineering News 14(14):10, 21.
Sensel et al., "Amino acid differences in the N-terminus of C(H)2 influence the relative abilities of IgG2 and IgG3 to activate complement," Molecular Immunology 34:1019-1029, 1997.
Shields et al., Lack of fucose on human IgG1 N-linked oligosaccharide improves binding to human Fc.gamma. RIII and antibody-dependent cellular toxicity. J Biol Chem. Jul. 26, 2002;277(30):26733-40.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Yeast polypeptide fusion surface display levels predict thermal stability and soluble secretion efficiency," J Mol Biol 292:949-956, 1999.
Shusta et al., "Increasing the secretory capacity of *Saccharomyces cerevisiae* for production of single-chain antibody fragments," Nature Biotechnology 16:773-777, 1998.
Shusta et al., "Directed evolution of a stable scaffold for T-cell receptor engineering," Nature Biotechnology 18:754-759, 2000.
Siberil, S. et al. (2006) "Molecular Aspects of Human FcgammaR Interactions with IgG: Functional and Therapeutic Consequences," Immunol. Lett. 106:111-118 (2006).
Skolnick et al. (2000) From Genes to Protein Structure and Function: Novel Aspects of Computational Approaches in the Genomic Era, Trends in Biotechnology 18:34-39.
Smith and Morrison, "Recombinant polymeric IgG: an approach to engineering more potent antibodies," Bio/Technology 12:683-688, 1994.
Sondermann and Oosthuizen, "The structure of Fc receptor/Ig complexes: considerations on stoichiometry and potential inhibitors," Immunology Letters, 82:51-56, 2002.
Sondermann et al., "Molecular basis for immune complex recognition: a comparison of Fc-receptor structures," J. Mol. Biol. 309:737-749, 2001.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "The 3.2-A crystal structure of the human IgG1 Fc fragment-Fc gammaRIII complex," Nature 406:267-273, 2000.
Stancovski et al. (1991) "Mechanistic aspects of the opposing effects of monoclonal antibodies to the ERBB2 receptor on tumor growth," Proc Natl Acad Sci U S A. 88(19):8691-8695.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Strohmeier et al., "Role of the Fc gamma R subclasses Fc gamma RII and Fc gamma RIII in the activation of human neutrophils by low and high valency immune complexes," J Leukocyte Biol 58:415-422, 1995.
Su et al., Expression profile of Fc.gamma.RIIB on leukocytes and its dysregulation in systemic lupus erythematosus. J. Immunol. 178:3272-3280, 2007.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "FcR gamma chain deletion results in pleiotrophic effector cell defects," Cell 76 :519-529, 1994.
Takai et al., "Augmented humoral and anaphylactic responses in Fc gamma RII-deficient mice," Nature 379:346-349, 1996.
Takai, "Roles of Fc receptors in autoimmunity," Nature Reviews 2:580-592, 2002.
Tam et al., A bispecific antibody against human IgE and human Fc.gamma.RII that inhibits antigen-induced histamine release by human mast cells and basophils. Allergy 2004;59:772-780.
Tamm et al., "The IgG binding site of human FcγRIIIB receptor involves CC' and FG loops of the membrane-proximal domain," J Biol Chem 271:3659-3666, 1996.

(56) References Cited

OTHER PUBLICATIONS

Tao and Morrison, Studies of aglycosylated chimeric mouse-human IgG. Role of carbohydrate in the structure and effector functions mediated by the human IgG constant region. J Immunol. Oct. 15, 1989;143(8):2595-601.

Tao et al., "The differential ability of human IgG1 and IgG4 to activate complement is determined by the COOH-terminal sequence of the CH2 domain," J Exp Med 173:1025-1028, 1991.

Tao et al., "Structural features of human immunoglobulin G that determine isotype-specific differences in complement activation," J Exp Med 178:661-667, 1993.

Todorovska et al., Design and application of diabodies, triabodies and tetrabodies for cancer targeting. J Immunol Methods. Feb. 1, 2001;248(1-2):47-66.

Tridandapandi et al., "Regulated Expression and Inhibitory Function of FcgammaRIIB in Human Monocytic Cells," Journal of Biological Chemistry 277(7): 5082-5089, 2002.

Umana et al., Engineered glycoforms of an antineuroblastoma IgG1 with optimized antibody-dependent cellular cytotoxic activity. Nat Biotechnol. Feb. 1999;17(2):176-80.

Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.

Van Antwerp and Wittrup, "Fine affinity discrimination by yeast surface display and flow cytometry," Biotechnol Prog 16:31-37, 2000.

Van den Beuken et al. (2001) Building novel binding ligands to B7.1 and B7.2 based on human antibody single variable light chain domains; J. Molec. Biol. 310:591-601.

Van De Winkel et al., 1995, "CD32 cluster workshop report." Leukocyte Typing V: White Cell differentiation antigens 823-825 (Schlossman, Boumsell, Gilks, Harlan, Kishomoto, eds.).

Van Nguyen et al., Colony stimulating factor-1 is required to recruit macrophages into the mammary gland to facilitate mammary ductal outgrowth. Dev Biol. 2002;247(1):11-25.

Van Sorge et al., "FcgammaR polymorphisms: Implications for function, disease susceptibility and immunotherapy," Tissue Antigens 61:189-202, 2003.

Vely et al., 1997, "A new set of monoclonal antibodies against human Fc gamma RII (CD32) and Fc gamma RIII (CD16): characterization and use in various assays." Hybridoma 16(6):519-28.

Veri, M.C. et al. (2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.

Vingerhoeds et al., Immunoliposomes in vivo. Immunomethods. Jun. 1994;4(3):259-72.

Vidarte, "Serine 132 is the C3 covalent attachment point on the CH1 domain of human IgG1," J Biol Chem 276:38217-38233, 2001.

Vitetta, E.S. et al. (2006) "Immunology. Cnsidering Therapeutic Antibodies," Science 313:308-309.

Vuist et al. (1990) "Two distinct mechanisms of antitumor activity mediated by the combination of interleukin 2 and monoclonal antibodies," Canc. Res. 50:5767-5772.

Wallick et al., Glycosylation of a VH residue of a monoclonal antibody against {acute over (.alpha.)} (1.fwdarw.6) dextran increases its affinity for antigen. J Exp Med. Sep. 1, 1988;168(3):1099-109.

Ward et al. (1989) Building Activities of a repertoire of single immunoglobulin variable domains secreted from *Escherichia coli*, Nature 341:544-546 (1989).

Ward and Ghetie, "The effector functions of immunoglobulins: implications for therapy," Therapeutic Immunology 2:77-94, 1995.

Warmerdam et al., Molecular basis for a polymorphism of human Fc gamma receptor II (CD32). J Exp Med. Jul. 1, 1990;172(1):19-25.

Warren, HS et al.(1999) "NK cells and apoptosis," Immunol. Cell Biol. 77(1):64-75.

Weng and Levy, "Two immunoglobulin G fragment C receptor polymorphisms independently predict response to rituximab in patients with follicular lymphoma," J Clin Oncol 21:3940-3947, 2003.

Wheeler, "Preventive Vaccines for Cervical Cancer," Salud Publica d Mexico, 1997, vol. 39, pp. 1-9.

Wiener, E. et al. "Differences between the activities of human monoclonal IgG1 and IgG3 anti-D antibodies of the Rh blood group system in their abilities to mediate effector functions of monocytes," Immunol. 65:159-163 (1988).

Weinrich, V. et al. "Epitope Mapping of New Monoclonal Antibodies Recognizing Distinct Human FCRII (CD32) Isoforms," Hybridoma 15(2):109-116.

Wing et al., "Mechanism of first-dose cytokine-release syndrome by CAMPATH 1-H: Involvement ofCD16 (FcγRIII) and CD11a/CD18 (LFA-1) on NK cells," J Clin Invest 98 :2819-2826, 1996.

Wingren et al., "Comparison of surface properties of human IgA, IgE, IgG and IgM antibodies with identical and different specificities," Scand J Immunol 44:430-436, 1996.

Wittrup, "The single cell as a microplate well," Nat Biotechnol 18:1039-1040, 2000.

Witttrup, "Protein engineering by cell-surface display," Curr, Opin. Biotechnol. 12:395-399, 2001.

Woof et al., "Localisation of the monocyte-binding region on human immunoglobulin G," Mol Immunol 23 :319-330, 1986.

Wright and Morrison, Effect of glycosylation on antibody function: implications for genetic engineering. Trends Biotechnol. Jan. 1997;15(1):26-32.

Wu et al., "A novel polymorphism of FcγRIIIa (CD16) alters receptor function and predisposes to autoimmune disease," J Clin Invst 100 :1059-1070, 1997.

Wu et al., "Humanization of a Murine Monoclonal Antibody by Simultaneous Optimization of Framework and CDR Residues," Journal of Molecular Biology, 1999, vol. 294, pp. 151-162.

Xu et al., Fc.gamma.Rs Modulate Cytotoxicity of Anti-Fas Antibodies: Implications for Agonistic Antibody Based Therapeutics. J Immunol. 2003;171:562-68.

Xu et al. (1993) "Antibody-induced growth inhibition is mediated through immunochemically and functionally distinct epitopes on the extracellular domain of the c-erbB-2 (HER-2/neu) gene product p185," Int. J. Cancer. 53(3):401-8.

Xu et al., "Residue at position 331 in the IgG1 and IgG4 CH2 domains contributes to their differential ability to bind and activate complement," J Biol Chem 269 :3469-3474, 1994.

Yeung and Wittrup, "Quantitative screening of yeast surface-displayed polypeptide libraries by magnetic bead capture," Biotechnol Prog 18:212-220, 2002.

Zeidler et al., "The Fc-region of a new class of intact bispecific antibody mediates activation of accessory cells and NK cells and induces direct phagocytosis of tumour cells," British J Cancer 83:261-266, 2000.

Zola et al., 2000, "CD32 (FcgammaRII)." J Biol Regul Homeost Agents 14(4):311-6.

Zuckier et al., "Chimeric human-mouse IgG antibodies with shuffled constant region exons demonstrate that multiple domains contribute to in vivo half-life," Cancer Res 58 :3905-3908, 1998.

Extended Search Report EP 05857521.8 (WO 06/088494) (2009) (6 pages).

International Search Report; PCT/US04/000643 (WO04/063351) (2004) (4 pages).

International Preliminary Report on Patentability PCT/US04/000643 (WO04/063351) (2007)(5 pages).

International Search Report; PCT/US05/024645 (WO06/088494) (2007) (3 pages).

International Preliminary Report on Patentability PCT/US05/024645(WO06/088494) (2007) (5 pages).

International Search Report; PCT/US06/031201 (WO07/021841) (2008) (2 pages).

International Preliminary Report on Patentability PCT/US06/031201(WO07/021841) (2008)(8 pages).

International Search Report; PCT/US07/086793 (WO08/140603) (2008) (5 pages).

(56) References Cited

OTHER PUBLICATIONS

International Preliminary Report on Patentability PCT/US07/086793 (WO08/140603) (2008)(9 pages).
European Search Report (EP 05778285) Apr. 14, 2008 (2 pages).
Singapore Search Report SG 200607186-4 Nov. 5, 2008 (2 pages).
International Search Report; PCT/US05/12798 (WO05/115452) (2005) (2 pages).
International Preliminary Report on Patentability PCT/US05/12798 (WO05/115452) (2005)(5 pages).
International Search Report; PCT/US07/72153 (WO08/019199) (2008) (4 pages).
International Preliminary Report on Patentability PCT/US07/72153 (WO08/019199) (2008)(11 pages).
Extended Search Report EP 05854332.2 (PCT/US2005/045586) (2009) (4 pages).
Extended Search Report EP 07758130.4 (PCT/US2007/063548) (2009) (6 pages).
International Search Report and Written Opinion PCT/US09/38171 (WO 2009/151717) (13 pages).
Extended Search Report EP 07799049 (PCT/US2007/072151) (2010) (7 pages).
Extended Search Report EP 07812341.1 (PCT/US2007/72153) (2009) (9 pages).
Extended Search Report EP 07873826.7 (PCT/US2007/069767) (2009) 8 pages).
International Search Report; PCT/US09/38201 (WO09/123894) (2009) (11 pages).
International Search Report; PCT/US07/069767 (WO08/105886) (2008) (4pages).
International Preliminary Report on Patentability PCT/US07/069767 (WO08/105886) (2008)(7 pages).
Holliger, P. (1993) "Diabodies: Small bivalent and bispecific antibody fragments," Proc. Natl. Acad. Sci. (U.S.A.) 90(14):6444-6448.
Wu et al. (2001) "Multimerization of a chimeric anti-DC20 Single-Chain Fv-Fc fusion protein is mediated through variable domain exchange," Protein Engineering 14(2): 1025-1033.
Sleister et al., "Subtractive Immunization; A tool for the generation of discriminatory antibodies to proteins of similar sequence," Journal of Immunological Methods 261: 213-220, (2002).

FIG. 1A-C

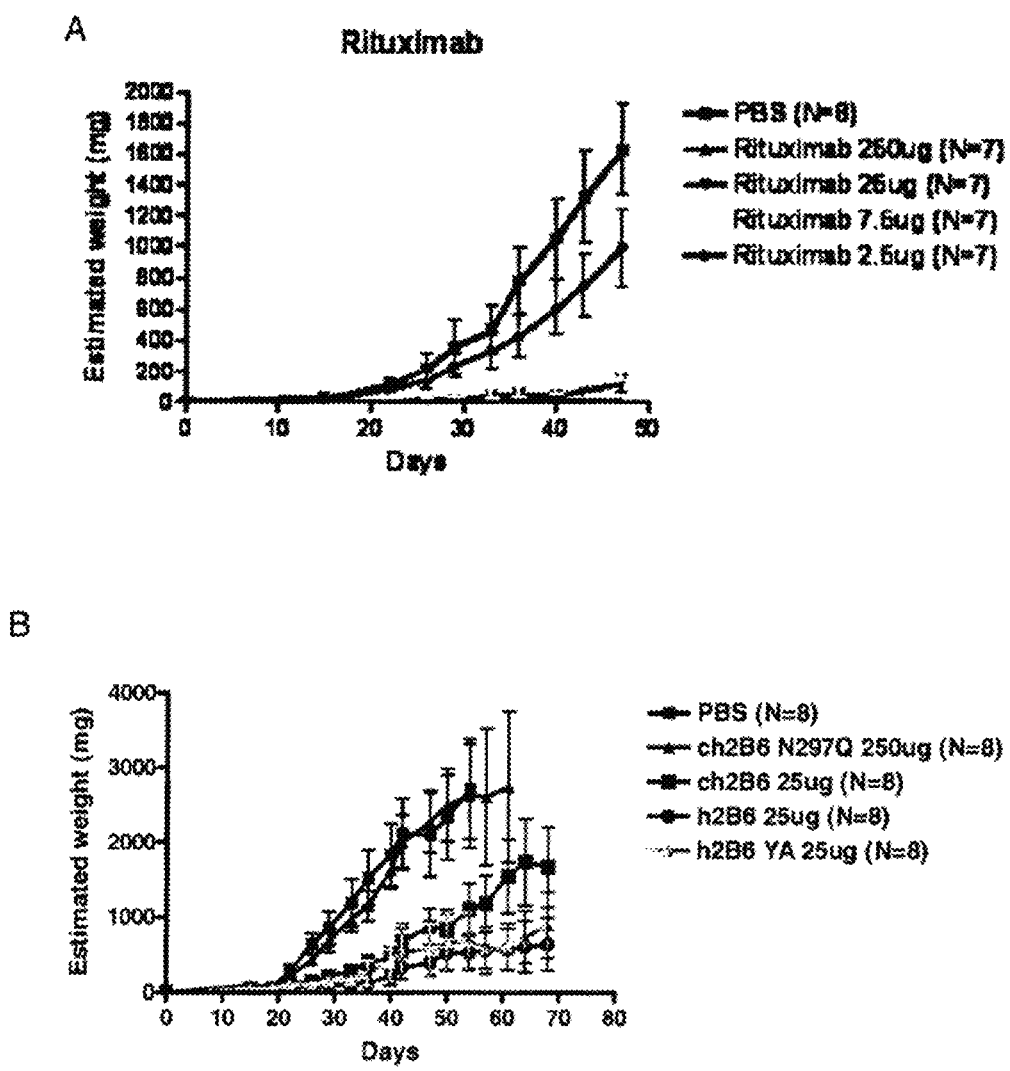
FIGS. 3A-B

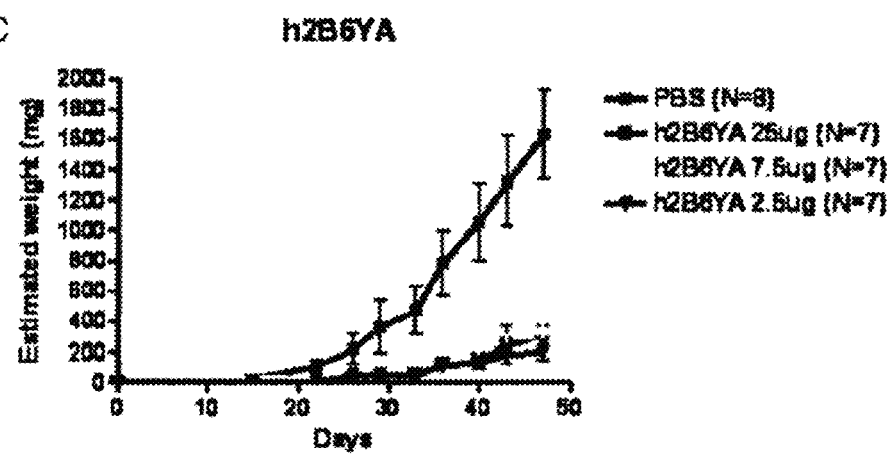
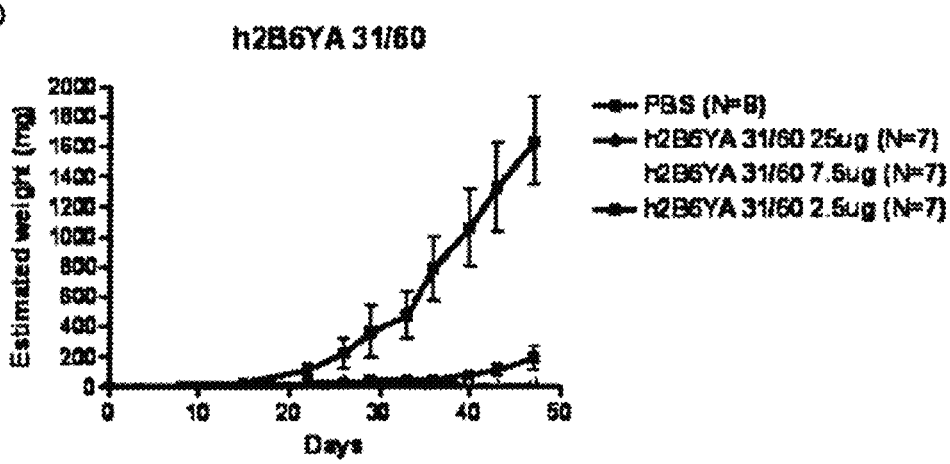
FIGS. 3C-D

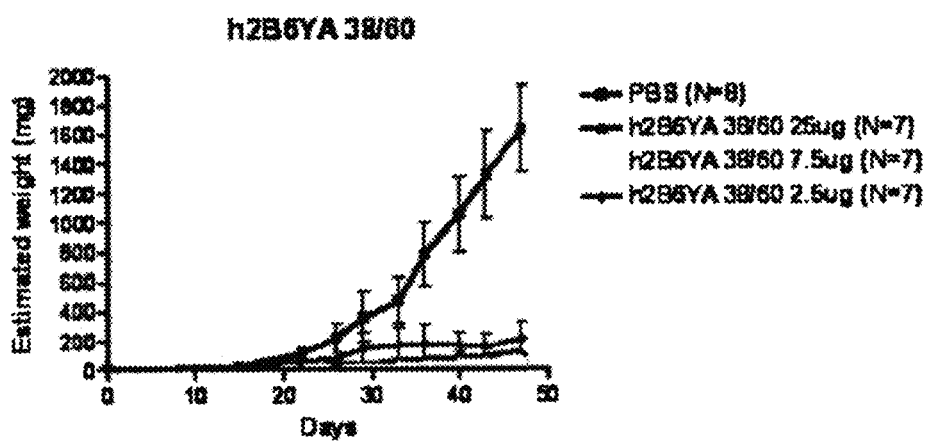
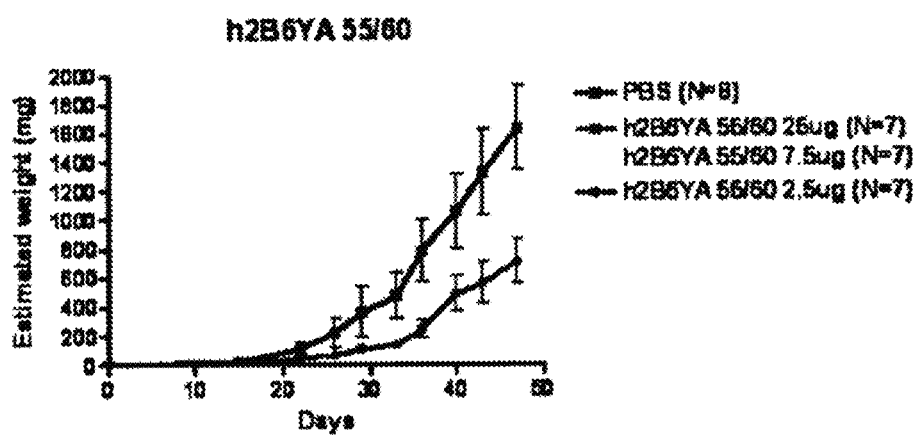
FIGS. 3E-F

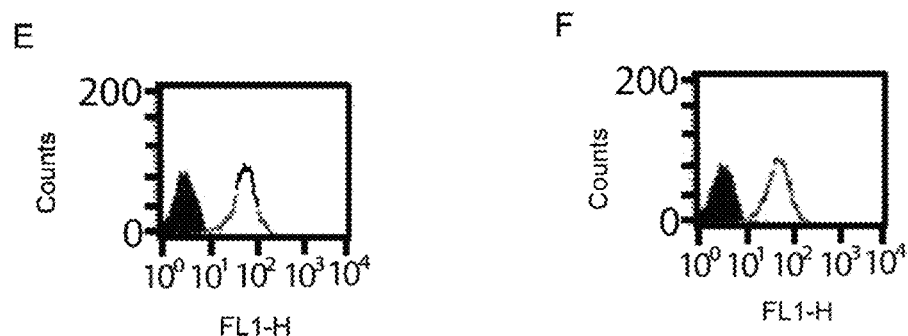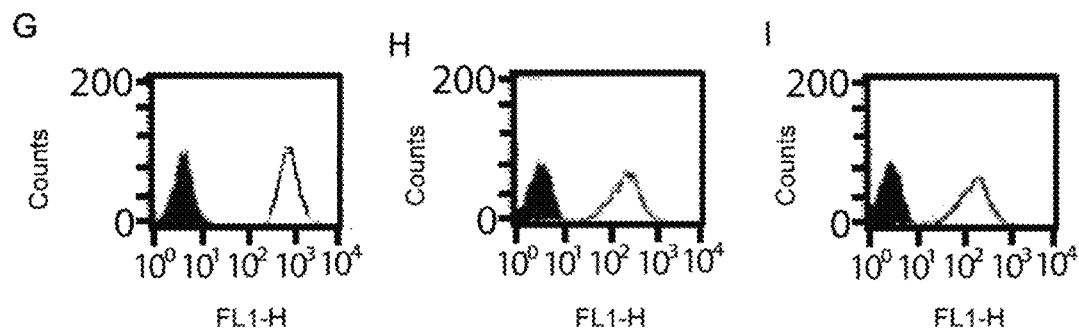
FIGS 4E-4I

Tonsils

Anti CD32B, 40X

Anti CD20, 40X

Normal Lymph Node

Anti-CD32B, 4X    Anti-CD20, 4X

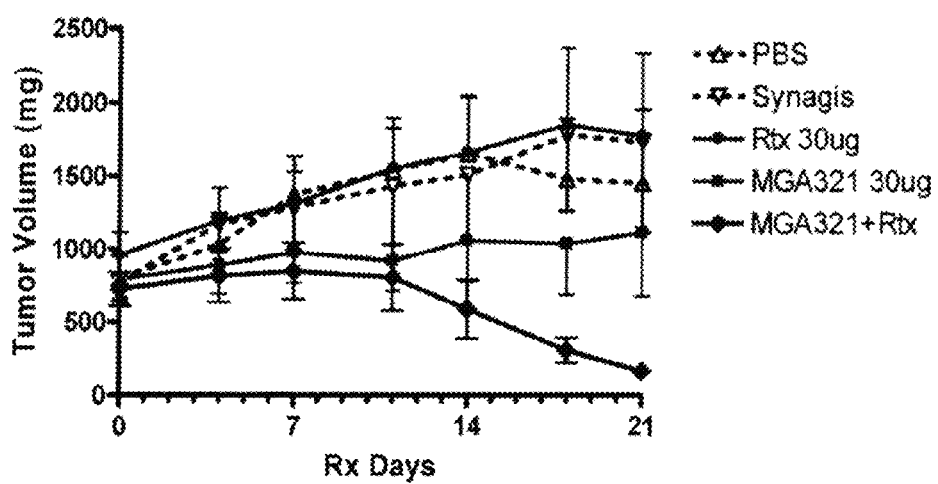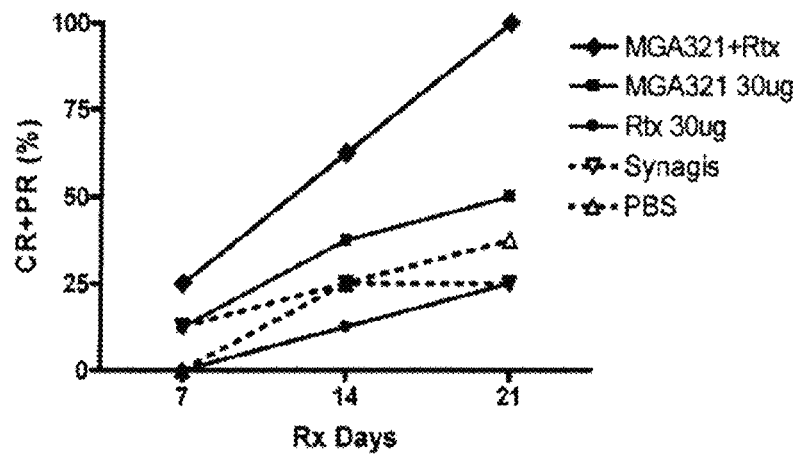
FIGS. 9A-B

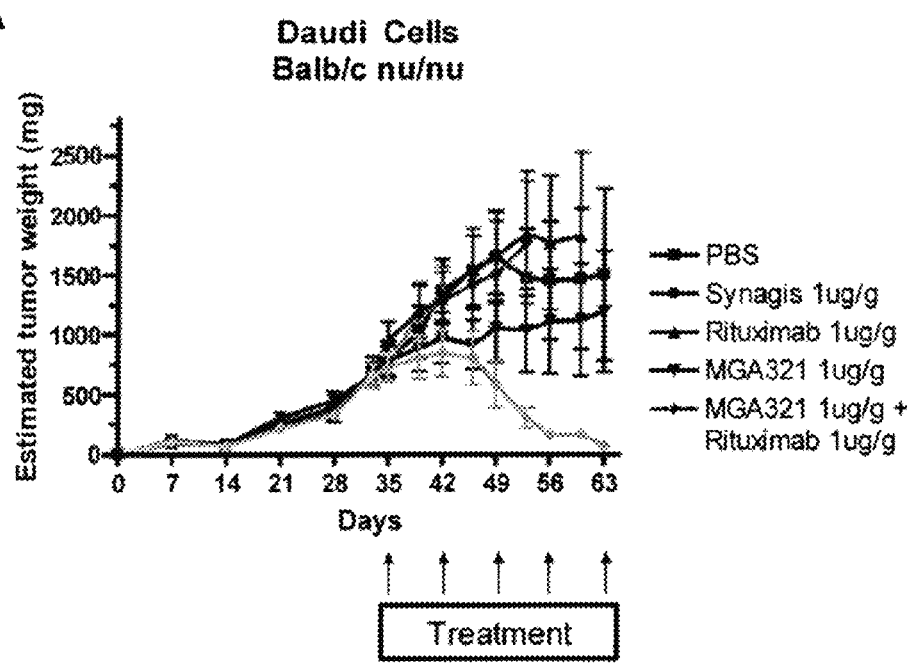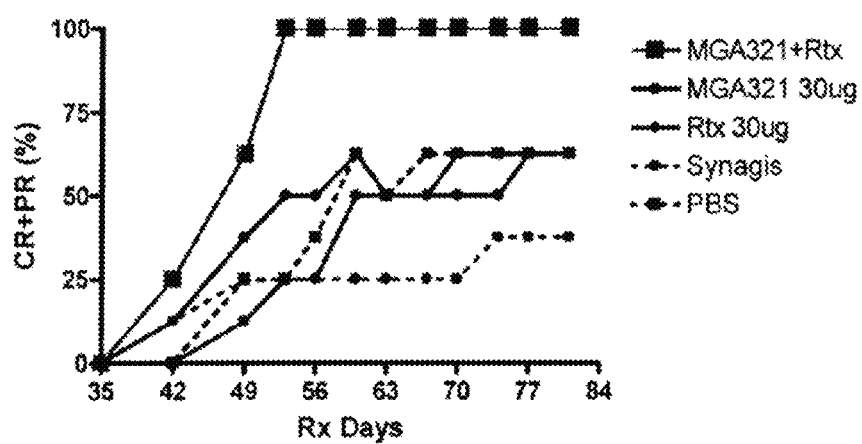
FIGS. 10A-B

8B5.3.4 VL nucleotide/amino acid sequence

```
gac att cag atg aca cag tct cca tcc tcc cta ctt gcg gcg ctg gga    48
Asp Ile Gln Met Thr Gln Ser Pro Ser Ser Leu Leu Ala Ala Leu Gly
 1               5                  10                  15

┌──────────────── CDR1 ────────
gaa aga gtc agt ctc act tgt cgg gca agt cag gaa att agt ggt tac    96
Glu Arg Val Ser Leu Thr Cys Arg Ala Ser Gln Glu Ile Ser Gly Tyr
            20                  25                  30

─────────┐
tta agc tgg ctt cag cag aaa cca gat gga act att aaa cgc ctg atc   144
Leu Ser Trp Leu Gln Gln Lys Pro Asp Gly Thr Ile Lys Arg Leu Ile
        35                  40                  45

┌─────── CDR2 ──────────┐
tac gcc gca tcc act tta gat tct ggt gtc cca aaa agg ttc agt ggc   192
Tyr Ala Ala Ser Thr Leu Asp Ser Gly Val Pro Lys Arg Phe Ser Gly
        50                  55                  60 agt gag tct ggg tca gat tat tct ctc acc atc agc agt ctt gag tct   240
Ser Glu Ser Gly Ser Asp Tyr Ser Leu Thr Ile Ser Ser Leu Glu Ser
 65                  70                  75                  80

┌──────────── CDR3 ─────────
gaa gat ttt gca gac tat tac tgt cta caa tat ttt agt tat ccg ctc   288
Glu Asp Phe Ala Asp Tyr Tyr Cys Leu Gln Tyr Phe Ser Tyr Pro Leu
                85                  90                  95

──────┐
acg ttc ggt gct ggg acc aag ctg gag ctg aaa                       321
Thr Phe Gly Ala Gly Thr Lys Leu Glu Leu Lys
            100                 105
```

FIG. 11

8B5.3.4 VH nucleotide/amino acid sequence

```
gaa gtg aag ctt gag gag tct gga gga ggc ttg gtg caa cct gga gga    48
Glu Val Lys Leu Glu Glu Ser Gly Gly Gly Leu Val Gln Pro Gly Gly
 1               5                  10                  15 tcc atg aaa ctc tct tgt gaa gcc tct gga ttc act ttt agt gac gcc    96
Ser Met Lys Leu Ser Cys Glu Ala Ser Gly Phe Thr Phe Ser Asp Ala
            20                  25                  30
```
*CDR1*
```
tgg atg gac tgg gtc cgt cag tct cca gag aag ggg ctt gag tgg gtt   144
Trp Met Asp Trp Val Arg Gln Ser Pro Glu Lys Gly Leu Glu Trp Val
        35                  40                  45
```
*CDR2*
```
gct gaa att aga aac aaa gct aaa aat cat gca aca tac tat gct gag   192
Ala Glu Ile Arg Asn Lys Ala Lys Asn His Ala Thr Tyr Tyr Ala Glu
        50                  55                  60 tct gtg ata ggg agg ttc acc atc tca aga gat gat tcc aaa agt agt   240
Ser Val Ile Gly Arg Phe Thr Ile Ser Arg Asp Asp Ser Lys Ser Ser
 65                  70                  75                  80 gtc tac ctg caa atg aac agc tta aga gct gaa gac act ggc att tat   288
Val Tyr Leu Gln Met Asn Ser Leu Arg Ala Glu Asp Thr Gly Ile Tyr
            85                  90                  95
```
*CDR3*
```
tac tgt ggg gct ctg ggc ctt gac tac tgg ggc caa ggc acc act ctc   336
Tyr Cys Gly Ala Leu Gly Leu Asp Tyr Trp Gly Gln Gly Thr Thr Leu
            100                 105                 110 aca gtc tcc tcg                                                    348
Thr Val Ser Ser
115
```

FIG. 12

SEQUENCE LISTING

<160> NUMBER OF SEQ ID NOS: 74

<210> SEQ ID NO 1
<211> LENGTH: 5
<212> TYPE: PRT
<213> ORGANISM: artificial
<220> FEATURE:
<223> OTHER INFORMATION: 2B6 Heavy Chain Variable Region CDR1

<400> SEQUENCE: 1

```
Asn Tyr Trp Ile His
1               5

<210> SEQ ID NO 2
<211> LENGTH: 16
<212> TYPE: PRT
<213> ORGANISM: artificial
<220> FEATURE:
<223> OTHER INFORMATION: 2B6 Heavy Chain Variable Region CDR2

<400> SEQUENCE: 2

Val Ile Asp Pro Ser Asp Thr Tyr Pro Asn Tyr Asn Lys Lys Phe Lys
1               5                   10                  15

<210> SEQ ID NO 3
<211> LENGTH: 12
<212> TYPE: PRT
<213> ORGANISM: artificial
<220> FEATURE:
<223> OTHER INFORMATION: 2B6 Heavy Chain Variable Region CDR3

<400> SEQUENCE: 3

Asn Gly Asp Ser Asp Tyr Tyr Ser Gly Met Asp Tyr
1               5                   10

<210> SEQ ID NO 4
<211> LENGTH: 30
<212> TYPE: PRT
<213> ORGANISM: artificial
<220> FEATURE:
<223> OTHER INFORMATION: Framework Sequence 1 from Human Germline VH1-18
      and JH6

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 5
<211> LENGTH: 14
<212> TYPE: PRT
<213> ORGANISM: artificial
<220> FEATURE:
<223> OTHER INFORMATION: Framework Sequence 2 From Human Germline VH1-18
      and JH6

<400> SEQUENCE: 5

Trp Val Arg Gln Ala Pro Gly Gln Gly Leu Glu Trp Met Gly
1               5                   10

<210> SEQ ID NO 6
<211> LENGTH: 32
<212> TYPE: PRT
<213> ORGANISM: artificial
<220> FEATURE:
<223> OTHER INFORMATION: Framework Sequence 3 From Human Germline VH1-18
      and JH6

<400> SEQUENCE: 6

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30
```

```
<210> SEQ ID NO 7
<211> LENGTH: 11
<212> TYPE: PRT
<213> ORGANISM: artificial
<220> FEATURE:
<223> OTHER INFORMATION: Framework Sequence 4 From Human Germline VH1-18
      and JH6

<400> SEQUENCE: 7

Trp Gly Gln Gly Thr Thr Val Thr Val Ser Ser
1               5                   10

<210> SEQ ID NO 8
<211> LENGTH: 11
<212> TYPE: PRT
<213> ORGANISM: artificial
<220> FEATURE:
<223> OTHER INFORMATION: 2B6 light chain variable region CDR1

<400> SEQUENCE: 8

Arg Thr Ser Gln Ser Ile Gly Thr Asn Ile His
1               5                   10

<210> SEQ ID NO 9
<211> LENGTH: 7
<212> TYPE: PRT
<213> ORGANISM: artificial
<220> FEATURE:
<223> OTHER INFORMATION: 2B6 light chain variable region CDR2

<400> SEQUENCE: 9

Asn Val Ser Glu Ser Ile Ser
1               5

<210> SEQ ID NO 10
<211> LENGTH: 7
<212> TYPE: PRT
<213> ORGANISM: artificial
<220> FEATURE:
<223> OTHER INFORMATION: 2B6 Light Chain Variable Region CDR2

<400> SEQUENCE: 10

Tyr Val Ser Glu Ser Ile Ser
1               5

<210> SEQ ID NO 11
<211> LENGTH: 7
<212> TYPE: PRT
<213> ORGANISM: artificial
<220> FEATURE:
<223> OTHER INFORMATION: 2B6 Light Chain Variable Region CDR2

<400> SEQUENCE: 11

Tyr Ala Ser Glu Ser Ile Ser
1               5

<210> SEQ ID NO 12
<211> LENGTH: 9
<212> TYPE: PRT
<213> ORGANISM: artificial
<220> FEATURE:
<223> OTHER INFORMATION: 2B6 Light Chain Variable Region CDR3

<400> SEQUENCE: 12

Gln Gln Ser Asn Thr Trp Pro Phe Thr
1               5
```

```
<210> SEQ ID NO 13
<211> LENGTH: 23
<212> TYPE: PRT
<213> ORGANISM: artificial
<220> FEATURE:
<223> OTHER INFORMATION: Framework Sequence 1 From Human Germline VK-A26
      and JK4

<400> SEQUENCE: 13

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 14
<211> LENGTH: 15
<212> TYPE: PRT
<213> ORGANISM: artificial
<220> FEATURE:
<223> OTHER INFORMATION: Framework Sequence 2 From Human Germline VK-A26
      and JK4

<400> SEQUENCE: 14

Trp Tyr Gln Gln Lys Pro Asp Gln Ser Pro Lys Leu Leu Ile Lys
1               5                   10                  15

<210> SEQ ID NO 15
<211> LENGTH: 32
<212> TYPE: PRT
<213> ORGANISM: artificial
<220> FEATURE:
<223> OTHER INFORMATION: Framework Sequence 3 From Human Germline VK-A26
      and JK4

<400> SEQUENCE: 15

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 16
<211> LENGTH: 10
<212> TYPE: PRT
<213> ORGANISM: artificial
<220> FEATURE:
<223> OTHER INFORMATION: Framework Sequence 4 From Human Germline VK-A26
      and JK4

<400> SEQUENCE: 16

Phe Gly Gly Gly Thr Lys Val Glu Ile Lys
1               5                   10

<210> SEQ ID NO 17
<211> LENGTH: 321
<212> TYPE: DNA
<213> ORGANISM: artificial
<220> FEATURE:
<223> OTHER INFORMATION: Humanized 2B6 Light Chain Variable Region
      (Hu2B6VL-1)

<400> SEQUENCE: 17
gaaattgtgc tgactcagtc tccagacttt cagtctgtga ctccaaagga gaaagtcacc      60
atcacctgca ggaccagtca gagcattggc acaaacatac actggtacca gcagaaacca     120
gatcagtctc caaagctcct catcaagaat gtttctgagt ctatctctgg agtcccatcg     180
aggttcagtg gcagtggatc tgggacagat ttcacccctca ccatcaatag cctggaagct     240
```

```
gaagatgctg caacgtatta ctgtcaacaa agtaatacct ggccgttcac gttcggcgga    300
gggaccaagg tggagatcaa a                                              321
```

<210> SEQ ID NO 18
<211> LENGTH: 107
<212> TYPE: PRT
<213> ORGANISM: artificial
<220> FEATURE:
<223> OTHER INFORMATION: Humanized 2B6 Light Chain Variable Region
      (Hu2B6VL-1)

<400> SEQUENCE: 18

```
Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Asn Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105
```

<210> SEQ ID NO 19
<211> LENGTH: 321
<212> TYPE: DNA
<213> ORGANISM: artificial
<220> FEATURE:
<223> OTHER INFORMATION: Humanized 2B6 Light Chain Variable Region
      (Hu2B6VL-2)

<400> SEQUENCE: 19

```
gaaattgtgc tgactcagtc tccagacttt cagtctgtga ctccaaagga gaaagtcacc    60
atcacctgca ggaccagtca gagcattggc acaaacatac actggtacca gcagaaacca   120
gatcagtctc caaagctcct catcaagtat gtttctgagt ctatctctgg agtcccatcg   180
aggttcagtg gcagtggatc tgggacagat ttcaccctca ccatcaatag cctggaagct   240
gaagatgctg caacgtatta ctgtcaacaa agtaatacct ggccgttcac gttcggcgga   300
gggaccaagg tggagatcaa a                                              321
```

<210> SEQ ID NO 20
<211> LENGTH: 107
<212> TYPE: PRT
<213> ORGANISM: artificial
<220> FEATURE:
<223> OTHER INFORMATION: Humanized 2B6 Light Chain Variable Region
      (Hu2B6VL-2)

<400> SEQUENCE: 20

```
Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45
```

```
Lys Tyr Val Ser Glu Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105
```

<210> SEQ ID NO 21
<211> LENGTH: 321
<212> TYPE: DNA
<213> ORGANISM: artificial
<220> FEATURE:
<223> OTHER INFORMATION: Humanized 2B6 Light Chain Variable Region
      (Hu2B6VL-3)

<400> SEQUENCE: 21

```
gaaattgtgc tgactcagtc tccagacttt cagtctgtga ctccaaagga gaaagtcacc    60
atcacctgca ggaccagtca gagcattggc acaaacatac actggtacca gcagaaacca   120
gatcagtctc caaagctcct catcaagtat gcttctgagt ctatctctgg agtcccatcg   180
aggttcagtg gcagtggatc tgggacagat ttcaccctca ccatcaatag cctggaagct   240
gaagatgctg caacgtatta ctgtcaacaa agtaatacct ggccgttcac gttcggcgga   300
gggaccaagg tggagatcaa a                                             321
```

<210> SEQ ID NO 22
<211> LENGTH: 107
<212> TYPE: PRT
<213> ORGANISM: artificial
<220> FEATURE:
<223> OTHER INFORMATION: Humanized 2B6 Light Chain Variable Region
      (Hu2B6VL-3)

<400> SEQUENCE: 22

```
Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105
```

<210> SEQ ID NO 23
<211> LENGTH: 363
<212> TYPE: DNA
<213> ORGANISM: artificial
<220> FEATURE:
<223> OTHER INFORMATION: Humanized 2B6 Heavy Chain Variable Region
      (Hu2B6VH-1)

<400> SEQUENCE: 23

```
caggttcagc tggtgcagtc tggagctgag gtgaagaagc tggggcctc agtgaaggtc        60 tcctgcaagg cttctggtta cacctttacc aactactgga tacactgggt gcgacaggcc      120
cctggacaag ggcttgagtg gatgggagtg attgatcctt ctgatactta tccaaattac      180
aataaaaagt tcaagggcag agtcaccatg accacagaca catccacgag cacagcctac      240
atggagctga ggagcctgag atctgacgac acggccgtgt attactgtgc gagaaacggt      300
gattccgatt attactctgg tatggactac tggggcaag ggaccacggt caccgtctcc       360
tca                                                                    363
```

```
<210> SEQ ID NO 24
<211> LENGTH: 121
<212> TYPE: PRT
<213> ORGANISM: artificial
<220> FEATURE:
<223> OTHER INFORMATION: Humanized 2B6 Heavy Chain Variable Region
      (Hu2B6VH-1)

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Val Ile Asp Pro Ser Asp Thr Tyr Pro Asn Tyr Asn Lys Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120
```

```
<210> SEQ ID NO 25
<211> LENGTH: 321
<212> TYPE: DNA
<213> ORGANISM: Mus sp.

<400> SEQUENCE: 25
gacatcttgc tgactcagtc tccagccatc ctgtctgtga gtccaggaga gagagtcagt       60
ttttcctgca ggaccagtca gagcattggc acaaacatac actggtatca gcaaagaaca      120
aatggttttc caaggcttct cataaagaat gtttctgagt ctatctctgg gatcccttcc      180
aggtttagtg gcagtggatc agggacagat tttattctta gcatcaacag tgtggagtct      240
gaagatattg cagattatta ttgtcaacaa agtaatacct ggccgttcac gttcggaggg      300
gggaccaagc tggaaataaa a                                                321
```

```
<210> SEQ ID NO 26
<211> LENGTH: 107
<212> TYPE: PRT
<213> ORGANISM: Mus sp.

<400> SEQUENCE: 26

Asp Ile Leu Leu Thr Gln Ser Pro Ala Ile Leu Ser Val Ser Pro Gly
1               5                   10                  15
```

-continued

Glu Arg Val Ser Phe Ser Cys Arg Thr Ser Gln Ser Ile Gly Thr Asn
            20                  25                  30

Ile His Trp Tyr Gln Gln Arg Thr Asn Gly Phe Pro Arg Leu Leu Ile
        35                  40                  45

Lys Asn Val Ser Glu Ser Ile Ser Gly Ile Pro Ser Arg Phe Ser Gly
50                  55                  60

Ser Gly Ser Gly Thr Asp Phe Ile Leu Ser Ile Asn Ser Val Glu Ser
65                  70                  75                  80

Glu Asp Ile Ala Asp Tyr Tyr Cys Gln Gln Ser Asn Thr Trp Pro Phe
                85                  90                  95

Thr Phe Gly Gly Gly Thr Lys Leu Glu Ile Lys
            100                 105

<210> SEQ ID NO 27
<211> LENGTH: 363
<212> TYPE: DNA
<213> ORGANISM: Mus sp.

<400> SEQUENCE: 27
caggtccaat tgcagcagcc tgtgactgag ctggtgaggc cgggggcttc agtgatgttg      60
tcctgcaagg cttctgacta ccccttcacc aactactgga tacactgggt aaagcagagg     120
cctggacaag gcctggagtg gatcggagtg attgatcctt ctgatactta tccaaattac     180
aataaaaagt tcaagggcaa ggccacattg actgtagtcg tatcctccag cacagcctac     240
atgcagctca gcagcctgac atctgacgat tctgcggtct attactgtgc aagaaacggt     300
gattccgatt attactctgg tatggactac tggggtcaag aacctcagt caccgtctcc      360 tca                                                                   363

<210> SEQ ID NO 28
<211> LENGTH: 121
<212> TYPE: PRT
<213> ORGANISM: Mus sp.

<400> SEQUENCE: 28

Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
50                  55                  60

Lys Gly Lys Ala Thr Leu Thr Val Val Val Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Ser Val Thr Val Ser Ser
        115                 120

<210> SEQ ID NO 29
<211> LENGTH: 5
<212> TYPE: PRT
<213> ORGANISM: artificial
<220> FEATURE:

<223> OTHER INFORMATION: 3H7 Heavy Chain Variable Region CDR1

<400> SEQUENCE: 29

Asp Ala Trp Met Asp
1               5

<210> SEQ ID NO 30
<211> LENGTH: 19
<212> TYPE: PRT
<213> ORGANISM: artificial
<220> FEATURE:
<223> OTHER INFORMATION: 3H7 Heavy Chain Variable Region CDR2

<400> SEQUENCE: 30

Glu Ile Arg Asn Lys Ala Asn Asn Leu Ala Thr Tyr Tyr Ala Glu Ser
1               5                   10                  15

Val Lys Gly

<210> SEQ ID NO 31
<211> LENGTH: 6
<212> TYPE: PRT
<213> ORGANISM: artificial
<220> FEATURE:
<223> OTHER INFORMATION: 3H7 Heavy Chain Variable Region CDR3

<400> SEQUENCE: 31

Tyr Ser Pro Phe Ala Tyr
1               5

<210> SEQ ID NO 32
<211> LENGTH: 30
<212> TYPE: PRT
<213> ORGANISM: artificial
<220> FEATURE:
<223> OTHER INFORMATION: 3H7 Heavy Chain Variable Region (FW1)

<400> SEQUENCE: 32

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser
                20                  25                  30

<210> SEQ ID NO 33
<211> LENGTH: 14
<212> TYPE: PRT
<213> ORGANISM: artificial
<220> FEATURE:
<223> OTHER INFORMATION: 3H7 Heavy Chain Variable Region (FW2)

<400> SEQUENCE: 33

Trp Val Arg Gln Gly Pro Glu Lys Gly Leu Glu Trp Val Ala
1               5                   10

<210> SEQ ID NO 34
<211> LENGTH: 30
<212> TYPE: PRT
<213> ORGANISM: artificial
<220> FEATURE:
<223> OTHER INFORMATION: 3H7 Heavy Chain Variable Region (FW3)

<400> SEQUENCE: 34

Arg Phe Thr Ile Pro Arg Asp Asp Ser Lys Ser Ser Val Tyr Leu His
1               5                   10                  15

Met Asn Ser Leu Arg Ala Glu Asp Thr Gly Ile Tyr Tyr Cys
                20                  25                  30

<210> SEQ ID NO 35
<211> LENGTH: 11
<212> TYPE: PRT
<213> ORGANISM: artificial
<220> FEATURE:
<223> OTHER INFORMATION: 3H7 Heavy Chain Variable Region (FW4)

<400> SEQUENCE: 35

Trp Gly Gln Gly Thr Leu Val Thr Val Ser Ala
1               5                   10

<210> SEQ ID NO 36
<211> LENGTH: 345
<212> TYPE: DNA
<213> ORGANISM: Mus sp.

<400> SEQUENCE: 36
gaagtgaagt ttgaggagtc tggaggaggc ttggtgcaac ctggaggatc catgaaactc     60
tcttgtgctg cctctggatt cacttttagt gacgcctgga tggactgggt ccgccagggt    120
ccagagaagg ggcttgagtg ggttgctgaa attagaaaca agctaataa tcttgcaaca    180 tactatgctg agtctgtgaa agggaggttc accatcccaa gagatgattc caaaagtagt    240
gtctacctgc acatgaacag cttaagagct gaagacactg gcatttatta ctgttatagt    300
ccctttgctt actggggcca agggactctg gtcactgtct ctgca                    345

<210> SEQ ID NO 37
<211> LENGTH: 115
<212> TYPE: PRT
<213> ORGANISM: Mus sp.

<400> SEQUENCE: 37

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Gly Pro Glu Lys Gly Leu Glu Trp Val
        35                  40                  45

Ala Glu Ile Arg Asn Lys Ala Asn Asn Leu Ala Thr Tyr Tyr Ala Glu
    50                  55                  60

Ser Val Lys Gly Arg Phe Thr Ile Pro Arg Asp Asp Ser Lys Ser Ser
65                  70                  75                  80

Val Tyr Leu His Met Asn Ser Leu Arg Ala Glu Asp Thr Gly Ile Tyr
                85                  90                  95

Tyr Cys Tyr Ser Pro Phe Ala Tyr Trp Gly Gln Gly Thr Leu Val Thr
            100                 105                 110

Val Ser Ala
        115

<210> SEQ ID NO 38
<211> LENGTH: 11
<212> TYPE: PRT
<213> ORGANISM: artificial
<220> FEATURE:
<223> OTHER INFORMATION: 3H7 Light Chain Variable Region CDR1

<400> SEQUENCE: 38

Arg Ala Ser Gln Glu Ile Ser Gly Tyr Leu Ser
1               5                   10

<210> SEQ ID NO 39
<211> LENGTH: 7
<212> TYPE: PRT
<213> ORGANISM: artificial
<220> FEATURE:
<223> OTHER INFORMATION: 3H7 Light Chain Variable Region CDR2

<400> SEQUENCE: 39

Ala Ala Ser Thr Leu Asp Ser
1               5

<210> SEQ ID NO 40
<211> LENGTH: 9
<212> TYPE: PRT
<213> ORGANISM: artificial
<220> FEATURE:
<223> OTHER INFORMATION: 3H7 Light Chain Variable Region CDR3

<400> SEQUENCE: 40

Leu Gln Tyr Val Ser Tyr Pro Tyr Thr
1               5

<210> SEQ ID NO 41
<211> LENGTH: 23
<212> TYPE: PRT
<213> ORGANISM: artificial
<220> FEATURE:
<223> OTHER INFORMATION: 3H7 Light Chain Variable Region (FW1)

<400> SEQUENCE: 41

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 42
<211> LENGTH: 15
<212> TYPE: PRT
<213> ORGANISM: artificial
<220> FEATURE:
<223> OTHER INFORMATION: 3H7 Light Chain Variable Region (FW2)

<400> SEQUENCE: 42

Trp Leu Gln Gln Lys Pro Asp Gly Thr Ile Arg Arg Leu Ile Tyr
1               5                   10                  15

<210> SEQ ID NO 43
<211> LENGTH: 32
<212> TYPE: PRT
<213> ORGANISM: artificial
<220> FEATURE:
<223> OTHER INFORMATION: 3H7 Light Chain Variable Region (FW3)

<400> SEQUENCE: 43

Gly Val Pro Lys Arg Phe Ser Gly Ser Trp Ser Gly Ser Asp Tyr Ser
1               5                   10                  15

Leu Thr Ile Ser Ser Leu Glu Ser Glu Asp Phe Ala Asp Tyr Tyr Cys
            20                  25                  30

<210> SEQ ID NO 44
<211> LENGTH: 10
<212> TYPE: PRT
<213> ORGANISM: artificial
<220> FEATURE:
<223> OTHER INFORMATION: 3H7 Light Chain Variable Region (FW4)

<400> SEQUENCE: 44

Phe Gly Gly Gly Thr Lys Leu Glu Ile Lys
1               5                   10

<210> SEQ ID NO 45
<211> LENGTH: 321
<212> TYPE: DNA
<213> ORGANISM: Mus sp.

<400> SEQUENCE: 45
gacatccaga tgacccagtc tccatcctcc ttatctgcct ctctgggaga aagagtcagt      60
ctcacttgtc gggcaagtca ggaaattagt ggttacttaa gctggcttca gcagaaacca     120
gatggaacta tttagacgcct gatctacgcc gcatccactt tagattctgg tgtcccaaaa   180
aggttcagtg gcagttggtc tgggtcagat tattctctca ccatcagcag ccttgagtct    240
gaagattttg cagactatta ctgtctacaa tatgttagtt atccgtatac gttcggaggg    300
gggaccaagc tggaaataaa a                                              321

<210> SEQ ID NO 46
<211> LENGTH: 107
<212> TYPE: PRT
<213> ORGANISM: Mus sp.

<400> SEQUENCE: 46

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Arg Arg Leu Ile
        35                  40                  45

Tyr Ala Ala Ser Thr Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Tyr
                85                  90                  95

Thr Phe Gly Gly Gly Thr Lys Leu Glu Ile Lys
            100                 105

<210> SEQ ID NO 47
<211> LENGTH: 22
<212> TYPE: DNA
<213> ORGANISM: artificial
<220> FEATURE:
<223> OTHER INFORMATION: Primer-SJ15R

<400> SEQUENCE: 47
ggtcactgtc actggctcag gg                                             22

<210> SEQ ID NO 48
<211> LENGTH: 28
<212> TYPE: DNA
<213> ORGANISM: artificial
<220> FEATURE:
<223> OTHER INFORMATION: Primer-SJ16R

<400> SEQUENCE: 48
aggcggatcc aggggccagt ggatagac                                       28

-continued

```
<210> SEQ ID NO 49
<211> LENGTH: 26
<212> TYPE: DNA
<213> ORGANISM: artificial
<220> FEATURE:
<223> OTHER INFORMATION: Primer-SJ17R

<400> SEQUENCE: 49
gcacacgact gaggcacctc cagatg                                          26

<210> SEQ ID NO 50
<211> LENGTH: 34
<212> TYPE: DNA
<213> ORGANISM: artificial
<220> FEATURE:
<223> OTHER INFORMATION: Primer-SJ18R

<400> SEQUENCE: 50
cggcggatcc gatggataca gttggtgcag catc                                 34

<210> SEQ ID NO 51
<211> LENGTH: 9
<212> TYPE: PRT
<213> ORGANISM: artificial
<220> FEATURE:
<223> OTHER INFORMATION: Partial Sequence of FcgammaRIIB/Fc huIgG2
      fusion protein

<400> SEQUENCE: 51

Lys Lys Phe Ser Arg Ser Asp Pro Asn
1               5

<210> SEQ ID NO 52
<211> LENGTH: 9
<212> TYPE: PRT
<213> ORGANISM: artificial
<220> FEATURE:
<223> OTHER INFORMATION: Partial Sequence of FcgammaRIIB/hu IgG2 fusion
      protein

<400> SEQUENCE: 52

Gln Lys Phe Ser Arg Leu Asp Pro Asn
1               5

<210> SEQ ID NO 53
<211> LENGTH: 9
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 53

Gln Lys Phe Ser Arg Leu Asp Pro Thr
1               5

<210> SEQ ID NO 54
<211> LENGTH: 9
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 54

Lys Lys Phe Ser Arg Leu Asp Pro Thr
1               5
```

<210> SEQ ID NO 55
<211> LENGTH: 9
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 55

Gln Lys Phe Ser His Leu Asp Pro Thr
1               5

<210> SEQ ID NO 56
<211> LENGTH: 9
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 56

Lys Lys Phe Ser His Leu Asp Pro Thr
1               5

<210> SEQ ID NO 57
<211> LENGTH: 5
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 57

Ala Pro Ser Ser Ser
1               5

<210> SEQ ID NO 58
<211> LENGTH: 8
<212> TYPE: PRT
<213> ORGANISM: artificial
<220> FEATURE:
<223> OTHER INFORMATION: Partial Sequence for FcgammaRIIB/hu IgG2 Fc
      fusion protein

<400> SEQUENCE: 58

Val Pro Ser Met Gly Ser Ser Ser
1               5

<210> SEQ ID NO 59
<211> LENGTH: 363
<212> TYPE: DNA
<213> ORGANISM: artificial
<220> FEATURE:
<223> OTHER INFORMATION: Humanized 2B6 Heavy Chain Variable Region
      (Hu2B6VH-A)

<400> SEQUENCE: 59
caggttcagc tggtgcagtc tggagctgag gtgaagaagc ctggggcctc agtgaaggtc      60
tcctgcaagg cttctggtta cacctttacc aactactgga tacactgggt gcgacaggcc     120
cctggacaag gcttgagtg gattggagtg attgatcctt ctgatactta tccaaattac     180
aataaaaagt tcaagggcag agtcaccatg accgtagtcg tatccacgag cacagcctac     240
atggagctga ggagcctgag atctgacgac acggccgtgt attactgtgc gagaaacggt     300
gattccgatt attactctgg tatggactac tggggggcaag ggaccacggt caccgtctcc     360

```
tca                                                                  363

<210> SEQ ID NO 60
<211> LENGTH: 121
<212> TYPE: PRT
<213> ORGANISM: artificial
<220> FEATURE:
<223> OTHER INFORMATION: Humanized 2B6 Heavy Chain Variable Region
      (Hu2B6VH-A)

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120

<210> SEQ ID NO 61
<211> LENGTH: 321
<212> TYPE: DNA
<213> ORGANISM: artificial
<220> FEATURE:
<223> OTHER INFORMATION: Humanized 2B6 Light Chain Variable Region
      (Hu2B6VL-5)

<400> SEQUENCE: 61
gaaattgtgc tgactcagtc tccagacttt cagtctgtga ctccaaagga gaaagtcacc      60
ttcacctgca ggaccagtca gagcattggc acaaacatac actggtacca gcagaaacca     120
gatcagtctc caaagctcct catcaaggag gtttctgagt ctatctctgg agtcccatcg     180
aggttcagtg gcagtggatc tgggacagat ttcaccctca ccatcaatag cctggaagct     240
gaagatgctg caacgtatta ctgtcaacaa agtaatacct ggccgttcac gttcggcgga     300
gggaccaagg tggagatcaa a                                               321

<210> SEQ ID NO 62
<211> LENGTH: 107
<212> TYPE: PRT
<213> ORGANISM: artificial
<220> FEATURE:
<223> OTHER INFORMATION: Humanized 2B6 Light Chain Variable Region
      (Hu2B6VL-5)

<400> SEQUENCE: 62

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45
```

```
Lys Glu Val Ser Glu Ser Ile Ser Gly Val Pro Ser Arg Phe Ser Gly
     50                  55                  60

Ser Gly Ser Gly Thr Asp Phe Thr Leu Thr Ile Asn Ser Leu Glu Ala
 65              70                  75                  80

Glu Asp Ala Ala Thr Tyr Tyr Cys Gln Gln Ser Asn Thr Trp Pro Phe
                 85                  90                  95

Thr Phe Gly Gly Gly Thr Lys Val Glu Ile Lys
            100                 105

<210> SEQ ID NO 63
<211> LENGTH: 1356
<212> TYPE: DNA
<213> ORGANISM: artificial
<220> FEATURE:
<223> OTHER INFORMATION: Humanized 2B6 Heavy Chain

<400> SEQUENCE: 63
```

| | | | |
|---|---|---|---|
| caggttcagc tggtgcagtc tggagctgag gtgaagaagc tggggcctc agtgaaggtc | 60 |
| tcctgcaagg cttctggtta cacctttacc aactactgga tacactgggt gcgacaggcc | 120 |
| cctggacaag gcttgagtg gattggagtg attgatcctt ctgatactta tccaaattac | 180 |
| aataaaaagt tcaagggcag agtcaccatg accgtagtcg tatccacgag cacagcctac | 240 |
| atggagctga ggagcctgag atctgacgac acggccgtgt attactgtgc gagaaacggt | 300 |
| gattccgatt attactctgg tatggactac tgggggcaag ggaccacggt caccgtctcc | 360 |
| tcagcctcca ccaagggccc atcggtcttc cccctggcac cctcctccaa gagcacctct | 420 |
| gggggcacag cggccctggg ctgcctggtc aaggactact ccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt accccccaaaa cccaaggaca cctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgccgga ggagcagtac | 900 |
| aacagcacgc tccgtgtggt cagcatcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctctc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaatga | 1356 |

```
<210> SEQ ID NO 64
<211> LENGTH: 451
<212> TYPE: PRT
<213> ORGANISM: artificial
<220> FEATURE:
<223> OTHER INFORMATION: Humanized 2B6 Heavy Chain

<400> SEQUENCE: 64
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Leu Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Leu
290                 295                 300

Arg Val Val Ser Ile Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Tyr Lys Thr Thr Pro Leu
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
```

```
                420            425            430
His Glu Ala Leu His Asn His Tyr Thr Gln Lys Ser Leu Ser Leu Ser
        435                440                445

Pro Gly Lys
    450

<210> SEQ ID NO 65
<211> LENGTH: 645
<212> TYPE: DNA
<213> ORGANISM: artificial
<220> FEATURE:
<223> OTHER INFORMATION: Humanized 2B6 Light Chain

<400> SEQUENCE: 65
gaaattgtgc tgactcagtc tccagacttt cagtctgtga ctccaaagga gaaagtcacc      60
ttcacctgca ggaccagtca gagcattggc acaaacatac actggtacca gcagaaacca     120
gatcagtctc caaagctcct catcaaggag gtttctgagt ctatctctgg agtcccatcg     180
aggttcagtg gcagtggatc tgggacagat ttcaccctca ccatcaatag cctggaagct     240
gaagatgctg caacgtatta ctgtcaacaa agtaatacct ggccgttcac gttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gttag                    645

<210> SEQ ID NO 66
<211> LENGTH: 214
<212> TYPE: PRT
<213> ORGANISM: artificial
<220> FEATURE:
<223> OTHER INFORMATION: Humanized 2B6 Light Chain

<400> SEQUENCE: 66

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 67
<211> LENGTH: 363
<212> TYPE: DNA
<213> ORGANISM: artificial
<220> FEATURE:
<223> OTHER INFORMATION: Humanized 2B6 Heavy Chain Variable Region
      (Hu2B6VH-3)

<400> SEQUENCE: 67
caggttcagc tggtgcagtc tggagctgag gtgaagaagc ctggggcctc agtgaaggtc      60
tcctgcaagg cttctggtta cacctttacc aactactgga tacactgggt gcgacaggcc    120
cctggacaag gcttgagtg gattggagtg attgatcctt ctgatactta tccaaattac     180
aataaaaagt tcaagggcag agtcaccatg accgtagaca catccacgag cacagcctac    240
atggagctga ggagcctgag atctgacgac acggccgtgt attactgtgc gagaaacggt    300
gattccgatt attactctgg tatggactac tggggcaag ggaccacggt caccgtctcc     360
tca                                                                   363

<210> SEQ ID NO 68
<211> LENGTH: 121
<212> TYPE: PRT
<213> ORGANISM: artificial
<220> FEATURE:
<223> OTHER INFORMATION: Humanized 2B6 Heavy Chain Variable Region
      (Hu2B6VH-3)

<400> SEQUENCE: 68

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Ile His Trp Val Arg Gln Ala Pro Gly Gln Gly Leu Glu Trp Ile
        35                  40                  45
Gly Val Ile Asp Pro Ser Asp Thr Tyr Pro Asn Tyr Asn Lys Lys Phe
    50                  55                  60
Lys Gly Arg Val Thr Met Thr Val Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asn Gly Asp Ser Asp Tyr Tyr Ser Gly Met Asp Tyr Trp Gly
            100                 105                 110
Gln Gly Thr Thr Val Thr Val Ser Ser
        115                 120

<210> SEQ ID NO 69
<211> LENGTH: 1356
<212> TYPE: DNA
<213> ORGANISM: artificial
<220> FEATURE:
```

<223> OTHER INFORMATION: Humanized 2B6 Heavy Chain (Hu2B6HC-3a)

<400> SEQUENCE: 69

```
caggttcagc tggtgcagtc tggagctgag gtgaagaagc tgggggcctc agtgaaggtc      60
tcctgcaagg cttctggtta cacctttacc aactactgga tacactgggt gcgacaggcc     120
cctggacaag ggcttgagtg gattggagtg attgatcctt ctgatactta tccaaattac     180
aataaaaagt tcaagggcag agtcaccatg accgtagaca catccacgag cacagcctac     240
atggagctga ggagcctgag atctgacgac acggccgtgt attactgtgc gagaaacggt     300
gattccgatt attactctgg tatggactac tgggggcaag gaccacggt caccgtctcc      360
tcagcctcca ccaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt accccccaaa cccaaggaca cctcatgat ctccccggacc      780
cctgaggtca catgcgtggt ggtggacgtg agccacgaag accctgaggt caagttcaac     840
tggtacgtgg acggcgtgga ggtgcataat gccaagacaa agccgccgga ggagcagtac     900
aacagcacgc tccgtgtggt cagcatcctc accgtcctgc accaggactg gctgaatggc     960
aaggagtaca agtgcaaggt ctccaacaaa gccctcccag cccccatcga gaaaaccatc    1020
tccaaagcca agggcagcc ccgagaacca caggtgtaca ccctgccccc atcccgggat      1080
gagctgacca gaaccaggt cagcctgacc tgcctggtca aaggcttcta tcccagcgac      1140
atcgccgtgg agtgggagag caatgggcag ccggagaaca actacaagac cacgcctctc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356
```

<210> SEQ ID NO 70
<211> LENGTH: 451
<212> TYPE: PRT
<213> ORGANISM: artificial
<220> FEATURE:
<223> OTHER INFORMATION: Humanized 2B6 Heavy Chain (Hu2B6HC-3a)

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
```

100                 105                 110
Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Leu
290                 295                 300

Arg Val Val Ser Ile Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Leu
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 71
<211> LENGTH: 116
<212> TYPE: PRT
<213> ORGANISM: artificial
<220> FEATURE:
<223> OTHER INFORMATION: Antibody 8B5.3.4 Heavy Chain Variable Sequence

<400> SEQUENCE: 71

Glu Val Lys Leu Glu Glu Ser Gly Gly Gly Leu Val Gln Pro Gly Gly

```
              1               5                  10                 15
Ser Met Lys Leu Ser Cys Glu Ala Ser Gly Phe Thr Phe Ser Asp Ala
                  20                  25                  30

Trp Met Asp Trp Val Arg Gln Ser Pro Glu Lys Gly Leu Glu Trp Val
            35                  40                  45

Ala Glu Ile Arg Asn Lys Ala Lys Asn His Ala Thr Tyr Tyr Ala Glu
        50                  55                  60

Ser Val Ile Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Gly Ala Leu Gly Leu Asp Tyr Trp Gly Gln Gly Thr Thr Leu
            100                 105                 110

Thr Val Ser Ser
            115

<210> SEQ ID NO 72
<211> LENGTH: 107
<212> TYPE: PRT
<213> ORGANISM: artificial
<220> FEATURE:
<223> OTHER INFORMATION: Antibody 8B5.3.4 Light Chain Variable Region

<400> SEQUENCE: 72

Asp Ile Gln Met Thr Gln Ser Pro Ser Ser Leu Leu Ala Ala Leu Gly
1               5                  10                  15

Glu Arg Val Ser Leu Thr Cys Arg Ala Ser Gln Glu Ile Ser Gly Tyr
                20                  25                  30

Leu Ser Trp Leu Gln Gln Lys Pro Asp Gly Thr Ile Lys Arg Leu Ile
            35                  40                  45

Tyr Ala Ala Ser Thr Leu Asp Ser Gly Val Pro Lys Arg Phe Ser Gly
        50                  55                  60

Ser Glu Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Phe Ser Tyr Pro Leu
                85                  90                  95

Thr Phe Gly Ala Gly Thr Lys Leu Glu Leu Lys
            100                 105

<210> SEQ ID NO 73
<211> LENGTH: 348
<212> TYPE: DNA
<213> ORGANISM: artificial
<220> FEATURE:
<223> OTHER INFORMATION: Antibody 8B5.3.4 Heavy Chain Variable Region

<400> SEQUENCE: 73
gaagtgaagc ttgaggagtc tggaggaggc ttggtgcaac ctggaggatc catgaaactc      60
tcttgtgaag cctctggatt cactttttagt gacgcctgga tggactgggt ccgtcagtct    120
ccagagaagg ggcttgagtg ggttgctgaa attagaaaca agctaaaaaa tcatgcaaca    180
tactatgctg agtctgtgat agggaggttc accatctcaa gagatgattc aaaaagtagt    240
gtctacctgc aaatgaacag cttaagagct gaagacactg gcatttatta ctgtggggct    300
ctgggccttg actactgggg ccaaggcacc actctcacag tctcctcg              348

<210> SEQ ID NO 74
<211> LENGTH: 321
```

```
<212> TYPE: DNA
<213> ORGANISM: artificial
<220> FEATURE:
<223> OTHER INFORMATION: Antibody 8B5.3.4 Light Chain Variable Region

<400> SEQUENCE: 74
gacattcaga tgacacagtc tccatcctcc ctacttgcgg cgctgggaga aagagtcagt         60
ctcacttgtc gggcaagtca ggaaattagt ggttacttaa gctggcttca gcagaaacca        120
gatggaacta ttaaacgcct gatctacgcc gcatccactt tagattctgg tgtcccaaaa        180
aggttcagtg gcagtgagtc tgggtcagat tattctctca ccatcagcag tcttgagtct        240
gaagattttg cagactatta ctgtctacaa tattttagtt atccgctcac gttcggtgct        300
gggaccaagc tggagctgaa a                                                  321
```

COMBINATION OF FCγRIIB-SPECIFIC ANTIBODIES AND CD20-SPECIFIC ANTIBODIES AND METHODS OF USE THEREOF

CROSS-REFERENCE TO RELATED APPLICATIONS

This application is a divisional of U.S. patent application Ser. No. 12/342,305, filed Dec. 23, 2008, which application is a continuation-in-part of and claims priority to United States Patent Application Ser. No. PCT/US07/72151, filed Jun. 26, 2007, which application claims priority to U.S. Patent Application Ser. No. 60/816,772, filed on Jun. 26, 2006, which applications are herein incorporated by reference in their entireties.

BACKGROUND OF THE INVENTION

Field of the Invention

The present invention relates to methods of treatment, prevention, management or amelioration of one or more symptoms of diseases or disorders associated with CD20 expression that encompass administration of a combination of: (A) one or more antibodies that specifically bind FcγRIIB, particularly human FcγRIIB, with greater affinity than said antibodies bind FcγRIIA, and (B) one or more antibodies that specifically bind to CD20. Such methods include methods of treating, preventing, managing or ameliorating one or more symptoms of a B cell related disease or disorder or an inflammatory disorder. The invention also provides pharmaceutical compositions comprising an anti-FcγRIIB antibody and an anti-CD20 antibody.

Description of Related Art

I. Fc Receptors and their Roles in the Immune System

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the a chain of the Fc receptor. Fc receptors are defined by their specificity for immunoglobulin subtypes. Fc receptors for IgG are referred to as FcγR, for IgE as FcεR, and for IgA as FcαR. Different accessory cells bear Fc receptors for antibodies of different isotype, and the isotype of the antibody determines which accessory cells will be engaged in a given response (reviewed by Ravetch J. V. et al. (1991) "Fc Receptors," Annu. Rev. Immunol. 9: 457-92; Gerber et al. (2001) "Stimulatory And Inhibitory Signals Originating From The Macrophage Fcgamma Receptors," Microbes and Infection, 3: 131-139; Billadeau et al. (2002), "ITAMs Versus ITIMs: Striking A Balance During Cell Regulation," The Journal of Clinical Investigation, 2(109): 161-168; Ravetch J. V. et al. (2000) "Immune Inhibitory Receptors," Science, 290: 84-89; Ravetch et al. (2001) "IgG Fc Receptors," Annu. Rev. Immunol. 19:275-290; Ravetch (1994) "Fc Receptors: Rubor Redux," Cell, 78(4): 553-560). The different Fc receptors, the cells that express them, and their isotype specificity is summarized in Table 1 (adapted from IMMUNOBIOLOGY: THE IMMUNE SYSTEM IN HEALTH AND DISEASE, 4$^{th}$ ed. 1999, Elsevier Science Ltd/Garland Publishing, New York).

A. Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology between the three family members suggest they arose from a common progenitor perhaps by gene duplication. This invention specifically focuses on FcγRII(CD32).

B. FcγRII (CD32)

FcγRII proteins are 40 KDa integral membrane glycoproteins which bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRIIA (CD32A) and FcγRIIB (CD32B) create two functionally heterogenous responses to receptor ligation. The fundamental difference is that the A isoform initiates intracellular signaling leading to cell activation such as phagocytosis and respiratory burst, whereas the B isoform initiates inhibitory signals, e.g., inhibiting B cell activation.

C. Signaling Through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI$_3$K). Cellular activation leads to release of proinflammatory mediators.

TABLE 1

Receptors for the Fc Regions of Immunoglobulin Isotypes

| Receptor | Binding | Cell Type | Effect of Ligation |
| --- | --- | --- | --- |
| FcγRI (CD64) | IgG1 $10^8$ M$^{-1}$ | Macrophages, Neutrophils, Eosinophils, Dendritic cells | Uptake Stimulation Activation of respiratory burst Induction of killing |
| FcγRII-A (CD32) | IgG1 $2 \times 10^6$ M$^{-1}$ | Macrophages, Neutrophils, Eosinophils, Dendritic cells, Platelets, Langerhan cells | Uptake Granule release |
| FcγRII-B2 (CD32) | IgG1 $2 \times 10^6$ M$^{-1}$ | Macrophages, Neutrophils, Eosinophils | Uptake Inhibition of Stimulation |
| FcγRII-BI (CD32) | IgG1 $2 \times 10^6$ M$^{-1}$ | B cells, Mast cells | No uptake Inhibition of Stimulation |
| FcγRIII (CD16) | IgG1 $5 \times 10^5$ M$^{-1}$ | NK cells, Eosinophil macrophages, Neutrophils, Mast Cells | Induction of Killing |
| FcεRI | IgG1 $10^{10}$ M$^{-1}$ | Mast cells, Eosinophil Basophils | Secretion of granules |
| FcαRI (CD89) | IgG1, IgA2 $10^7$ M$^{-1}$ | Macrophages, Neutropils Eosinophils | Uptake Induction of killing |

II. Therapeutic Use of Anti-CD20 Antibodies

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When colligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular Ca$^{++}$. Thus, crosslinking of FcγRIIB dampens the activating response to FcγR ligation and inhibits cellular responsiveness. B cell activation, B cell proliferation and antibody secretion is thus aborted.

T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. The CD20 molecule is a hydrophobic transmembrane protein with a molecular weight of approximately 35 kD located on pre-B and mature B lymphocytes (Valentine et al. (1989) "*Phosphorylation of the CD20 Phosphoprotein In Resting B Lymphocytes. Regulation By Protein Kinase C*," J. Biol. Chem. 264:11282-11287; and Einfield et al. (1988) "*Molecular Cloning Of The Human B cell CD20 Receptor Predicts A Hydrophobic Protein With Multiple Transmembrane Domains*," EMBO J. 7:711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) "*Expression of Human B Cell-Associated Antigens On Leukemias And Lymphomas: A Model Of Human B Cell Differentiation*," Blood 63:1424-1433), but is not found on hematopoietic stem cells, pro-B cells, normal plasma cells, or other normal tissues (Tedder et al. (1985) "*The B Cell Surface Molecule B1 Is Functionally Linked With B Cell Activation And Differentiation*," J. Immunol. 135:973-979). Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, i.e., those B cells whose unabated proliferation can lead to B cell lymphoma. Thus, the CD20 surface antigen has the potential of serving as a candidate for "targeting" of B cell lymphomas.

The use of antibodies to the CD20 antigen as diagnostic and/or therapeutic agents for B cell lymphoma has previously been reported. CD20 is a useful marker or target for B cell lymphomas as this antigen is expressed at very high densities on the surface of malignant B cells, i.e., B cells wherein unabated proliferation can lead to B cell lymphomas. The CD20 antigen is appealing for targeted therapy, because it does not shed, modulate, or internalize.

The United States Food and Drug Administration (FDA) has approved a chimeric CD20-specific monoclonal antibody (rituximab) for lymphoma therapy. Initial clinical experience with CD20-targeted immunotherapy suggests that malignant B cells may have a limited capacity to down regulate CD20 expression. These attributes make CD20 an attractive target for genetically engineered, redirected T cells.

III. Diseases of Relevance

A. Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, BASIC PATHOLOGY, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime. A cure for cancer has yet to be found. Current treatment options, such as surgery, chemotherapy and radiation treatment, are often times either ineffective or present serious side effects.

B. B Cell Malignancies

B cell malignancies, including, but not limited to, B cell lymphomas and leukemias, are neoplastic diseases with significant incidence in the United States. There are approximately 55,000 new lymphoma cases of per year in the U.S. (1998 data), with an estimated 25,000 deaths per year. This represents 4% of cancer incidence and 4% of all cancer-related deaths in the U.S. population. The revised European-American classification of lymphoid neoplasms (1994 REAL classification, modified 1999) grouped lymphomas based on their origin as either B cell lineage lymphoma, T cell lineage lymphoma, or Hodgkin's lymphoma. Lymphoma of the B cell lineage is the most common type of non-Hodgkin's lymphoma (NHL) diagnosed in the U.S. (Williams, HEMATOLOGY $6^{th}$ ed. (Beutler et al. Ed.), McGraw Hill 2001). Chronic lymphocytic leukemia (CLL) is a neoplastic disease characterized by the accumulation of small, mature-appearing lymphocytes in the blood, marrow, and lymphoid tissues. CLL has an incidence of 2.7 cases per 100,000 in the U.S. The risk increases progressively with age, particularly in men. It accounts for 0.8% of all cancers and is the most common adult leukemia, responsible for 30% of all leukemias. In nearly all cases (>98%) the diseased cells belong to the B lymphocyte lineage. A non-leukemic variant, small lymphocytic lymphoma, constitutes 5-10% of all lymphomas, has histological, morphological and immunological features indistinguishable from that of involved lymph nodes in patients with B-CLL (Williams, 2001).

The natural history of chronic lymphocytic leukemia falls into several phases. In the early phase, chronic lymphocytic leukemia is an indolent disease, characterized by the accumulation of small, mature, functionally-incompetent malignant B cells having a lengthened life span. Eventually, the doubling time of the malignant B cells decreases and patients become increasingly symptomatic. While treatment with chemotherapeutic agents can provide symptomatic relief, the overall survival of the patients is only minimally extended. The late stages of chronic lymphocytic leukemia are characterized by significant anemia and/or thrombocytopenia. At this point, the median survival is less than two years (Foon et al. (1990) "*Chronic Lymphocytic Leukemia: New Insights into Biology and Therapy*," Annals Int. Medicine 113:525-539). Due to the very low rate of cellular proliferation, chronic lymphocytic leukemia is resistant to treatment with chemotherapeutic agents.

C. Cancer Therapy

Currently, cancer therapy may involve surgery, chemotherapy, hormonal therapy and/or radiation treatment to eradicate neoplastic cells in a patient (See, for example, Stockdale, 1998, "*Principles of Cancer Patient Management*", in SCIENTIFIC AMERICAN: MEDICINE, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., GOODMAN AND GILMAN'S: THE PHARMACOLOGICAL BASIS OF THERAPEUTICS, Eighth Ed. (Pergamom Press, New York, 1990)). These agents, which include alkylating agents, such as nitrosourea, anti-metabolites, such as methotrexate and hydroxyurea, and other agents, such as etoposides, camptothecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "*Principles of Cancer Patient Management*", in SCIENTIFIC AMERICAN: MEDICINE, vol. 3, Rubenstein and Federman, eds., Chapter 12, Section IV). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

B cell malignancy is generally treated with single agent chemotherapy, combination chemotherapy and/or radiation therapy. These treatments can reduce morbidity and/or improve survival, albeit they carry significant side effects. The response of B cell malignancies to various forms of treatment is mixed. For example, in cases in which adequate clinical staging of non-Hodgkin's lymphoma is possible, field radiation therapy can provide satisfactory treatment.

Certain patients, however, fail to respond and disease recurrence with resistance to treatment ensues with time, particularly with the most aggressive variants of the disease. About one-half of the patients die from the disease (Devesa et al. (1987) "*Cancer Incidence And Mortality Trends Among Whites In The United States, 1947-84*," J. Nat'l Cancer Inst. 79:701-770).

Though B cell lymphoma is generally responsive to chemotherapy or radiation therapy, these treatments carry significant side effects and do not work all the time. Moreover, a large percentage of patients remain at significant risk for disease relapse (Glass et al. (1997) "*The National Cancer Data Base Report On Non-Hodgkin's Lymphoma*," Cancer 80:2311-2320). Investigational therapies for the treatment of refractory B cell neoplasia include autologous and allogeneic bone marrow or stem cell transplantation and gene therapies.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Recently, immunotherapy using monoclonal antibodies to target B cell specific antigens has been introduced in the treatment of B cell neoplasia. The use of monoclonal antibodies to direct radionuclides, toxins, or other therapeutic agents offers the possibility that such agents can be delivered selectively to tumor sites, thus limiting toxicity to normal tissues.

Major efforts have been directed at harnessing the specificity of the immune response, for example, hybridoma technology has enabled the development of tumor selective monoclonal antibodies (See Green et al. (2000) "*Monoclonal Antibody Therapy For Solid Tumors*," Cancer Treat Rev., 26: 269-286; Weiner L M (1999) "*Monoclonal Antibody Therapy Of Cancer*," Semin Oncol. 26(suppl. 14):43-51), and in the past few years, the Food and Drug Administration has approved the first MAbs for cancer therapy: RITUXAN® (rituximab, anti-CD20) for non-Hodgkin's Lymphoma (NHL), CamPath® (alemtuzumab, anti-CD52) for B cell chronic lymphocytic leukemia (B-CLL) and Herceptin® [Trastuzumab, anti-(c-erb-2/HER-2)] for metastatic breast cancer (S. A. Eccles (2001) "*Monoclonal Antibodies Targeting Cancer: 'Magic Bullets' Or Just The Trigger?*" Breast Cancer Res., 3: 86-90). NHL and B-CLL are two of the most common forms of B cell neoplasia.

One of the most successful examples of immunotherapy using monoclonal antibodies to target B cell specific antigens is the use of a chimerized anti-CD20 monoclonal antibody, rituximab, in treating follicular lymphoma.

The chimeric anti-CD20 mAb, rituximab, is an effective treatment for low-grade or follicular B cell NHLs. However, not all NHL patients are amenable to treatment with currently available anti-CD20 antibodies, and rituximab has a response rate of about 50%. In phase I studies, rituximab induced a rapid depletion of $CD20^+$ normal and lymphoma cells. Phase II trials with low-grade or follicular lymphoma showed a 50% response rate, whereas intermediate- to high-grade lymphomas showed a lower response rate. The reason for the heterogeneity of the response of different histologies and different patients is not clear. In addition to its anti-tumor effect, rituximab also induces rapid and profound depletion of $CD20^+$ normal B cells in the peripheral blood and bone marrow. The depletion of normal B cells persisted long after the rituximab treatment, which can last for 6 months, followed by a slow recovery.

Use of these antibodies has some clinical efficacy, but not without side effects. The mechanism of how, e.g., rituximab kills the tumor cells in patients is not fully understood. Recent studies have suggested an important role for Antibody-Dependent Cellular Cytotoxicity (ADCC). The potency of antibody effector function, e.g., ADCC, is an obstacle to such treatment. Furthermore, with RITUXAN® and CamPath®, at least half the patients fail to respond and a fraction of responders may be refractory to subsequent treatments.

Thus, there is a need for alternative therapies with improved clinical efficacy for cancer, particularly, B cell malignancies, especially for patients that are refractory for standard cancer treatments and new immunotherapies such as RITUXAN®.

D. Inflammatory and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T cell stimulation, cytokine secretion, synovial cell activation, and joint destruction. The disease has a major impact on both the individual and society, causing significant pain, impaired function and disability, as well as costing millions of dollars in healthcare expenses and lost wages. (See, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

SUMMARY OF THE INVENTION

The present invention relates to methods of treatment, prevention, management or amelioration of one or more symptoms of diseases or disorders associated with CD20 expression that encompass administration of a combination of (a) one or more antibodies that specifically bind FcγRIIB, particularly human FcγRIIB, with greater affinity than said antibodies bind FcγRIIA, and (b) one or more antibodies that specifically bind to CD20. Such methods include methods of treating, preventing, managing or ameliorating one or more symptoms of a B cell related disease or disorder or an inflammatory and/or autoimmune disorder. The invention also provides pharmaceutical compositions comprising an anti-FcγRIIB antibody and an anti-CD20 antibody. The invention is based on the inventors' surprising finding that the combination of an anti-FcγRIIB antibody and an anti-CD20 antibody has an additive and/or synergistic effect.

In one aspect, the invention provides compositions comprising a combination of (A) a FcγRIIB-specific antibody, an analog, derivative or an antigen-binding fragment thereof (e.g., one or more complementarity determining regions ("CDRs") of a FcγRIIB-specific antibody), and (B) a CD20-specific antibody, an analog, derivative or an antigen-binding fragment thereof (e.g., one or more CDRs of a CD20-specific antibody). In certain embodiments, the composition is a pharmaceutical compositions comprising a combination of (A) a FcγRIIB-specific antibody, an analog, derivative or an antigen-binding fragment thereof (e.g., one or more CDRs of a FcγRIIB-specific antibody) and (B) a CD20-specific antibody, an analog, derivative or an antigen-binding fragment thereof (e.g., one or more CDRs of a CD20-specific antibody), and (C) a pharmaceutically acceptable carrier.

In a second aspect, the invention encompasses the use or administration of a combination of (A) a FcγRIIB-specific antibody, an analog, derivative or an antigen-binding fragment thereof (e.g., one or more CDRs of a FcγRIIB-specific antibody), and (B) a CD20-specific antibody, an analog, derivative or an antigen-binding fragment thereof (e.g., one or more CDRs of a CD20-specific antibody) in the prevention, treatment, management or amelioration of a disease, such as cancer, in particular, a B cell malignancy, or one or more symptoms thereof. In certain embodiments, a method of preventing, managing, treating or ameliorating a B cell malignancy is provided, wherein the method comprises administering to a subject a composition comprising a combination of (A) a FcγRIIB-specific antibody, an analog, derivative or an antigen-binding fragment thereof (e.g., one or more CDRs of a FcγRIIB-specific antibody) and (B) a CD20-specific antibody, an analog, derivative or an antigen-binding fragment thereof (e.g., one or more CDRs of a CD20-specific antibody), wherein the composition optionally further comprises a pharmaceutically acceptable carrier. In certain embodiments, the B cell malignancy is a tumor of B cell origin. In some embodiments, the B cell malignancy, or symptom thereof, is prevented, treated, managed or ameliorated and is selected from lymphomas, chronic lymphocytic leukemias, acute lymphoblastic leukemias, multiple myeloma, Hodgkin's and non-Hodgkin's disease, diffuse large B cell lymphoma, follicular lymphoma with areas of diffuse large B cell lymphoma, small lymphocytic lymphoma, mantle cell lymphoma, and diffuse small cleaved cell lymphoma or combinations thereof. In certain embodiments, the B cell malignancy is a lymphoma, such as non-Hodgkin's Lymphoma (NHL) or B cell chronic lymphocytic leukemia (B-CLL).

In a third aspect, the invention encompasses the use or administration of a combination of (A) a FcγRIIB-specific antibody, an analog, derivative or an antigen-binding fragment thereof (e.g., one or more CDRs of a FcγRIIB-specific antibody), and (B) a CD20-specific antibody, an analog, derivative or an antigen-binding fragment thereof (e.g., one or more CDRs of a CD20-specific antibody) in the prevention, treatment, management or amelioration of a disease, such as an inflammatory disease, in particular, an autoimmune disease, or one or more symptoms thereof. In one embodiment, the invention provides a method of treating an inflammatory disorder in a patient in need thereof, said method comprising administering to said patient a therapeutically effective amount of one or more FcγRIIB-specific antibodies, or an antigen-binding fragment thereof, in combination with one or more CD20-specific antibodies, or an antigen-binding fragment thereof, of the invention. The invention also provides a method of treating an inflammatory disorder in a patient in need thereof, said method further comprising administering to said patient a therapeutically effective amount of one or more anti-inflammatory agents, and/or one or more immunomodulatory agents. In certain embodiments, a method of preventing, managing, treating or ameliorating a inflammatory disease is provided, wherein the method comprises administering to a subject a composition comprising a combination of (A) a FcγRIIB-specific antibody, an analog, derivative or an antigen-binding fragment thereof (e.g., one or more CDRs of a FcγRIIB-specific antibody) and (B) a CD20-specific antibody, an analog, derivative or an antigen-binding fragment thereof (e.g., one or more CDRs of a CD20-specific antibody), wherein the composition optionally further comprises a pharmaceutically acceptable carrier. In certain embodiments, the inflammatory disease is an autoimmune disease, such as Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis or combinations thereof. In specific embodiments, the autoimmune disease is rheumatoid arthritis.

Virtually any FcγRIIB-specific antibody, analog, derivative or antigen-binding fragment thereof (e.g., one or more CDRs of a FcγRIIB-specific antibody) can be used in the compositions and methods of the invention in combination with virtually any CD20-specific antibody, analog, derivative or antigen-binding fragment thereof (e.g., one or more CDRs of a FcγRIIB-specific antibody).

In certain embodiments, the compositions and methods of the invention comprise an isolated antibody (such as a monoclonal antibody) or a fragment thereof that specifically binds FcγRIIB, particularly human FcγRIIB, more particularly native human FcγRIIB, with a greater affinity than said antibody or a fragment thereof binds FcγRIIA, particularly human FcγRIIA, more particularly native human FcγRIIA. Representative antibodies are disclosed in U.S. Pat. No. 7,425,620; U.S. Publication Nos. 2004-0185045; 2005-0260213; and 2006-0013810, which are all herein expressly incorporated by reference in their entireties.

Preferably certain FcγRIIB antibodies used in combination with CD20 antibodies in the compositions and methods of the invention bind the extracellular domain of native human FcγRIIB. In some embodiments, the antibody or a fragment thereof binds FcγRIIB with at least 2 times greater affinity than said antibody or a fragment thereof binds FcγRIIA. In other embodiments, the antibody or a fragment thereof binds FcγRIIB with at least 4 times, at least 6 times, at least 8 times, at least 10 times, at least 100 times, at least 1000 times, at least $10^4$, at least $10^5$, at least $10^6$, at least $10^7$, or at least $10^8$ times greater affinity than said antibody or a fragment thereof binds FcγRIIA. In a preferred embodiment, said antibody or a fragment thereof binds FcγRIIB with 100 times, 1000 times, $10^4$ times, $10^5$ times, $10^6$ times, $10^7$ times, or $10^8$ times greater affinity than said antibody or a fragment thereof binds FcγRIIA. Preferably, these binding affinities are determined with the monomeric IgG, and not the aggregated IgG, and binding is via the variable domain (e.g., Fab fragments of the antibodies have binding characteristic similar to the full immunoglobulin molecule). The invention relates to compositions and methods comprising an isolated antibody or a fragment thereof that specifically binds FcγRIIB with a greater affinity than said antibody or a fragment thereof binds FcγRIIA, as determined by any standard method known in the art for assessing specificities, in combination with an anti-CD20 antibody.

In certain embodiments of the invention, the anti-FcγRIIB and/or anti-CD20 antibodies are monoclonal antibodies, synthetic antibodies, recombinantly produced antibodies, multispecific antibodies, human antibodies, chimeric antibodies, camelized antibodies, single-chain Fvs (scFv), single chain antibodies, Fab fragments, F(ab') fragments, disulfide-linked Fvs (sdFv), intrabodies, or epitope-binding fragments of any of the above. Preferably, the antibodies of the invention are monoclonal antibodies, and more preferably, humanized or human antibodies.

In one specific preferred embodiment, antibodies used in the combination therapies of the invention bind to the extracellular domain of human FcγRIIB, particularly native human FcγRIIB. In another specific embodiment, the antibodies specifically or selectively recognize one or more epitopes of FcγRIIB, particularly native human FcγRIIB. Another embodiment of the invention encompasses the use of phage display technology to increase the affinity of the antibodies for FcγRIIB. Any screening method known in the art can be used to identify mutant antibodies with increased avidity for FcγRIIB (e.g., ELISA). In another specific embodiment, antibodies are screened using antibody screening assays well known in the art (e.g., BIACORE assays) to identify antibodies with $K_{off}$ rate less than $3 \times 10^{-3}$ $s^{-1}$.

Hybridomas producing antibodies 2B6, 3H7, and 8B5.3.4 have been deposited with the American Type Culture Collection (10801 University Blvd., Manassas, Va. 20110-2209)

on Aug. 13, 2002 (2B6 and 3H7) and May 23, 2006 (8B5.3.4) under the provisions of the Budapest Treaty on the International Recognition of the Deposit of Microorganisms for the Purposes of Patent Procedures, and assigned accession numbers PTA-4591 (for hybridoma producing 2B6), PTA-4592 (for hybridoma producing 3H7), and PTA-7610 (for hybridoma producing 8B5.3.4) respectively, and are incorporated herein by reference.

In a preferred embodiment, the invention provides antibody combinations comprising a monoclonal antibody produced by clone 2B6, 3H7, or 8B5.3.4 having ATCC accession numbers PTA-4591, PTA-4592 and PTA-7610, respectively, or chimeric, humanized or other engineered versions thereof. In another preferred embodiment, the invention provides a monoclonal antibody produced by clone 1D5, 2E1, 2H9, 2D11, and 1F2 having ATCC accession numbers, PTA-5958, PTA-5961, PTA-5962, PTA-5960, and PTA-5959, respectively, or chimeric, humanized or other engineered versions thereof. In another embodiment, the invention provides an isolated antibody or a fragment thereof that competes for binding with the monoclonal antibody produced by clone 2B6, 3H7, or 8B5.3.4 and binds FcγRIIB, preferably native human FcγRIIB with a greater affinity than said antibody or a fragment thereof binds FcγRIIA, preferably native human FcγRIIA and/or binds to the same epitope of FcγRIIB as the monoclonal antibody produced from clone 2B6, 3H7, or 8B5.3.4 and binds FcγRIIB with a greater affinity than said antibody or a fragment thereof binds FcγRIIA. Furthermore, the invention provides hybridoma cell line 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively.

In one particular embodiment, an engineered version of the FcγRIIB-specific antibody and/or the anti-CD20 antibody comprises one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof. Examples of FcγRIIB-specific antibodies, including FcγRIIB-specific antibodies comprising Fc region mutations, that can be used in the compositions and methods of the invention can be found in U.S. Application Publication No. 2005-0260213, which is herein incorporated by reference. Examples of CD20-specific antibodies, including FcγRIIB-specific antibodies comprising Fc region mutations, that can be used in the compositions and methods of the invention can be found in U.S. patent application Ser. No. 11/271,140 by Stavenhagen, which is herein incorporated by reference. Preferably, an antibody comprises an Fc region having a leucine at position 243, a proline at position 292, a leucine at position 300, an isoleucine at position 305, and a leucine at position 396.

In a preferred embodiment, a humanized 2B6 comprises a heavy chain variable domain having the amino acid sequence of:

```
                                    (SEQ ID NO: 24)
QVQLVQSGAE VKKPGASVKV SCKASGYTFT

NYWIHWVRQA PGQGLEWMGV IDPSDTYPNY

NKKFKGRVTM TTDTSTSTAY MELRSLRSDD

TAVYYCARNG DSDYYSGMDY WGQGTTVTVS S;
``` a heavy chain variable domain having the amino acid sequence of:

```
                                    (SEQ ID NO: 28)
QVQLQQPVTE LVRPGASVML SCKASDYPFT

NYWIHWVKQR PGQGLEWIGV IDPSDTYPNY

NKKFKGKATL TVVVSSSTAY MQLSSLTSDD

SAVYYCARNG DSDYYSGMDY WGQGTSVTVS S;
``` a heavy chain variable domain having the amino acid sequence of:

```
                                    (SEQ ID NO: 60)
QVQLVQSGAE VKKPGASVKV SCKASGYTFT

NYWIHWVRQA PGQGLEWIGV IDPSDTYPNY

NKKFKGRVTM TVVVSTSTAY MELRSLRSDD

TAVYYCARNG DSDYYSGMDY WGQGTTVTVS S;
``` or a heavy chain variable domain having the amino acid sequence of:

```
                                    (SEQ ID NO: 68)
QVQLVQSGAE VKKPGASVKV SCKASGYTFT

NYWIHWVRQA PGQGLEWIGV IDPSDTYPNY

NKKFKGRVTM TVDTSTSTAY MELRSLRSDD

TAVYYCARNG DSDYYSGMDY WGQGTTVTVS S;
and
``` a light chain variable domain having the amino acid sequence of:

```
                                    (SEQ ID NO: 18)
EIVLTQSPDF QSVTPKEKVT ITCRTSQSIG TNIHWYQQKP

DQSPKLLIKN VSESISGVPS RFSGSGSGTD FTLTINSLEA

EDAATYYCQQ SNTWPFTFGG GTKVEIK;
``` a light chain variable domain having the amino acid sequence of:

```
                                    (SEQ ID NO: 20)
EIVLTQSPDF QSVTPKEKVT ITCRTSQSIG TNIHWYQQKP

DQSPKLLIKY VSESISGVPS RFSGSGSGTD FTLTINSLEA

EDAATYYCQQ SNTWPFTFGG GTKVEIK;
``` a light chain variable domain having the amino acid sequence of:

```
                                    (SEQ ID NO: 22)
EIVLTQSPDF QSVTPKEKVT ITCRTSQSIG TNIHWYQQKP

DQSPKLLIKY ASESISGVPS RFSGSGSGTD FTLTINSLEA

EDAATYYCQQ SNTWPFTFGG GTKVEIK;
``` a light chain variable domain having the amino acid sequence of:

```
                                               (SEQ ID NO: 26)
DILLTQSPAI LSVSPGERVS FSCRTSQSIG TNIHWYQQRT

NGFPRLLIKN VSESISGIPS RFSGSGSGTD FILSINSVES

EDIADYYCQQ SNTWPFTFGG GTKLEIK;
or
``` a light chain variable domain having the amino acid sequence of:

```
                                               (SEQ ID NO: 62)
EIVLTQSPDF QSVTPKEKVT FTCRTSQSIG TNIHWYQQKP

DQSPKLLIKE VSESISGVPS RFSGSGSGTD FTLTINSLEA

EDAATYYCQQ SNTWPFTFGG GTKVEIK.
```

In another preferred embodiment, the Fc domain of the heavy chain of the humanized 2B6, humanized 3H7 or humanized 8B5.3.4 antibody is engineered to comprise at least one amino acid substitution at position 240, 243, 247, 255, 270, 292, 300, 316, 370, 392, 396, 416, 419, or 421 with another amino acid at that position. In a more preferred embodiment, the Fc domain of the heavy chain of the humanized 2B6 has a leucine at position 247, a lysine at position 421 and a glutamic acid at position 270; a threonine at position 392, a leucine at position 396, and a glutamic acid at position 270; or a glutamic acid at position 270, an aspartic acid at position 316, and a glycine at position 416. In certain embodiments of the invention, the antibody is not a monoclonal antibody produced by clone 2B6, 3H7, or 8B5.3.4, or chimeric, humanized or other engineered versions thereof.

In certain embodiments of the invention, humanized 2B6 antibodies are provided, said humanized 2B6 antibodies comprising a heavy chain variable domain having the amino acid sequence of SEQ ID NOS:24, 28, 60 or SEQ ID NO:68 and a light chain variable domain having the amino acid sequence of SEQ ID NOS:18, 20, 22, 26 or SEQ ID NO:62, wherein the Fc domain of the heavy chain of the humanized 2B6 has a leucine at position 247, a lysine at position 421 and a glutamic acid at position 270; or a glutamic acid at position 270, an aspartic acid at position 316, and a glycine at position 416. In certain embodiments, the a FcγRIIB-specific antibody, analog, derivative or antigen-binding fragment thereof (e.g., one or more CDRs of a FcγRIIB-specific antibody) has a modified Fc domain with a leucine at position 243, a proline at position 292, a leucine at position 300, an isoleucine position 305 and a leucine at position 396.

In one specific embodiment, the invention provides a humanized 3H7 antibody, wherein the VH region consists of the FR segments from a human germline VH segment (SEQ ID NO:32, SEQ ID NO:33, SEQ ID NO:34, AND SEQ ID NO:35), and the CDR regions of the 3H7 VH (SEQ ID NO:29, SEQ ID NO:30, AND SEQ ID NO:31), having the amino acid sequence of:

```
                                               (SEQ ID NO: 37)
EVKFEESGGGLVQPGGSMKLSCAASGFTFSDAWMDWVRQ

GPEKGLEWVAEIRNKANNLATYYAESVKGRFTIPRDDSKSS

VYLHMNSLRAEDTGIYYCYSPFAYWGQGTLVTVSA;
```

In another specific embodiment, the humanized 3H7 antibody further comprises a VL region, which consists of the FR segments of the human germline VL segment (SEQ ID NO:41, SEQ ID NO:42, SEQ ID NO:43, and SEQ ID NO:44), and the CDR regions of 3H7VL (SEQ ID NO:38, SEQ ID NO:39, and SEQ ID NO:40), having an amino acid sequence of:

```
                                               (SEQ ID NO: 46)
DIQMTQSPSS LSASLGERVS LTCRASQEIS GYLSWLQQKP

DGTIRRLIYA ASTLDSGVPK RFSGSWSGSD YSLTISSLES

EDFADYYCLQ YVSYPYTFGG GTKLEIK.
```

In certain embodiments of the invention, humanized 2B6 antibodies are provided, said humanized 2B6 antibodies comprising a heavy chain variable domain having the amino acid sequence of SEQ ID NO:37, and a light chain variable domain having the amino acid sequence of SEQ ID NO:46, wherein the Fc domain of the heavy chain of the humanized 3H7 has a leucine at position 247, a lysine at position 421 and a glutamic acid at position 270; or a glutamic acid at position 270, an aspartic acid at position 316, and a glycine at position 416. In certain embodiments, the a FcγRIIB-specific antibody, analog, derivative or antigen-binding fragment thereof (e.g., one or more CDRs of a FcγRIIB-specific antibody) has a modified Fc domain with a leucine at position 243, a proline at position 292, a leucine at position 300, an isoleucine position 305 and a leucine at position 396.

In one specific embodiment, (A) a FcγRIIB antibody, such as a 2B6 (see, e.g., U.S. application Ser. No. 11/754,015, filed May 25, 2007), which is herein incorporated by reference in its entirety), 3H7, 8B5.3.4 (see, e.g., U.S. application Ser. No. 11/768,852, filed Jun. 26, 2007), which is herein incorporated by reference in its entirety), 1D5, 2E1, 2H9, 2D11, or 1F2 antibody, or analogs, derivatives, variants or antigen-binding fragments thereof of any of the above-referenced antibodies (e.g., one or more CDRs of a CD20-specific antibody), including chimeric, humanized or other engineered versions thereof, fully human versions thereof, and/or Fc variants thereof, is used in combination with (B) a CD20-specific antibody, such as 2B8 (rituximab, commercial name RITUXAN®; IDEC/Genentech; Roche/Zettyaku; Xoma) (U.S. Pat. Nos. 5,736,137 and 7,151,164, each of which is incorporated herein by reference in its entirety), 2H7 (see Liu et al. (1987) "*Production Of A Mouse-Human Chimeric Monoclonal Antibody To CD20 With Potent Fc-Dependent Biologic Activity*," J. Immunol. 139: 3521-3526; Clark et al. (1985) "*Role Of The Bp35 Cell Surface Polypeptide In Human B-Cell Activation*," Proc. Natl. Acad. Sci. USA 82:1766-1770; U.S. Pat. No. 5,500,400; U.S. Application Publication Nos. 2006-0024300 and 2006-0034835, each of which is incorporated herein by reference in its entirety), 1F5 (Clark et al. (1985) "*Role Of The Bp35 Cell Surface Polypeptide In Human B-Cell Activation*," Proc. Natl. Acad. Sci. USA 82:1766-1770; Press et al. (1987) "*Monoclonal Antibody 1F5 (anti-CD20) Serotherapy Of Human B cell Lymphomas*," Blood 69:584-591, each of which is incorporated herein by reference in its entirety), B1 (Nadler et al. (1981) "*A Unique Cell Surface Antigen Identifying Lymphoid Malignancies Of B Cell Origin*," J. Clin. Invest. 67:134-140, which is incorporated herein by reference in its entirety), ibritumomab (commercial name ZEVALIN™ (IDEC/Schering AG)), or tositumomab (commercial name BEXXAR®, Glaxo-SmithKline; Corixa); a CD20 antibody as described in U.S. Application Publication Nos. 2005-0025764, WO 05/000901, WO 04/035607, or WO 05/103081), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof, to prevent, treat, manage or ameliorate a CD20-associated disease or disorder, or one or more symptoms thereof.

In certain embodiments, (A) a FcγRIIB antibody, such as a 2B6 (see, e.g., U.S. application Ser. No. 11/754,015, filed May 25, 2007), which is herein incorporated by reference in its entirety), 3H7, 8B5.3.4 (see, e.g., U.S. application Ser. No. 11/768,852, filed Jun. 26, 2007), which is herein incorporated by reference in its entirety), 1D5, 2E1, 2H9, 2D11, or 1F2 antibody, or analogs, derivatives, variants or antigen-binding fragments thereof of any of the above-referenced antibodies (e.g., one or more CDRs of a CD20-specific antibody), including chimeric, humanized or other engineered versions thereof, fully human versions thereof, and/or Fc variants thereof, is used in combination with (B) a CD20-specific antibody, such as 2B8 (rituximab, commercial name RITUXAN®; IDEC/Genentech; Roche/Zettyaku; Xoma) (U.S. Pat. Nos. 5,736,137 and 7,151,164, each of which is incorporated herein by reference in its entirety), 2H7 (see Liu et al. (1987) "*Production Of A Mouse-Human Chimeric Monoclonal Antibody To CD20 With Potent Fc-Dependent Biologic Activity*," J. Immunol. 139: 3521-3526; Clark et al. (1985) "*Role Of The Bp35 Cell Surface Polypeptide In Human B-Cell Activation*," Proc. Natl. Acad. Sci. USA 82:1766-1770; U.S. Pat. No. 5,500,400; U.S. Application Publication Nos. 2006-0024300 and 2006-0034835, each of which is incorporated herein by reference in its entirety), 1F5 (Clark et al. (1985) "*Role Of The Bp35 Cell Surface Polypeptide In Human B-Cell Activation*," Proc. Natl. Acad. Sci. USA 82:1766-1770; Press et al. (1987) "*Monoclonal Antibody 1F5 (anti-CD20) Serotherapy Of Human B cell Lymphomas*," Blood 69:584-591, each of which is incorporated herein by reference in its entirety), B1 (Nadler et al. (1981) "*A Unique Cell Surface Antigen Identifying Lymphoid Malignancies Of B Cell Origin*," J. Clin. Invest. 67:134-140, which is incorporated herein by reference in its entirety), ibritumomab (commercial name ZEVALIN™ (IDEC/Schering AG)), or tositumomab (commercial name BEXXAR®, Glaxo-SmithKline; Corixa); a CD20 antibody as described in U.S. Application Publication Nos. 2005-0025764, WO 05/000901, WO 04/035607, or WO 05/103081), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof, to prevent, treat, manage or ameliorate a B cell malignancy, or one or more symptoms thereof. In certain embodiments, the B cell malignancy is a lymphoma, such as NHL or B-CLL.

In some embodiments, (A) a FcγRIIB antibody, such as a 2B6 (see, e.g., U.S. application Ser. No. 11/754,015, filed May 25, 2007), which is herein incorporated by reference in its entirety), 3H7, 8B5.3.4 (see, e.g., U.S. application Ser. No. 11/768,852, filed Jun. 26, 2007), which is herein incorporated by reference in its entirety), 1D5, 2E1, 2H9, 2D11, or 1F2 antibody, or analogs, derivatives, variants or antigen-binding fragments thereof of any of the above-referenced antibodies (e.g., one or more CDRs of a CD20-specific antibody), including chimeric, humanized or other engineered versions thereof, fully human versions thereof, and/or Fc variants thereof, is used in combination with (B) a CD20-specific antibody, such as 2B8 (rituximab, commercial name RITUXAN®; IDEC/Genentech; Roche/Zettyaku; Xoma) (U.S. Pat. Nos. 5,736,137 and 7,151,164, each of which is incorporated herein by reference in its entirety), 2H7 (see Liu et al. (1987) "*Production Of A Mouse-Human Chimeric Monoclonal Antibody To CD20 With Potent Fc-Dependent Biologic Activity*," J. Immunol. 139: 3521-3526; Clark et al. (1985) "*Role Of The Bp35 Cell Surface Polypeptide In Human B-Cell Activation*," Proc. Natl. Acad. Sci. USA 82:1766-1770; U.S. Pat. No. 5,500,400; U.S. Application Publication Nos. 2006-0024300 and 2006-0034835, each of which is incorporated herein by reference in its entirety), 1F5 (Clark et al. (1985) "*Role Of The Bp35 Cell Surface Polypeptide In Human B-Cell Activation*," Proc. Natl. Acad. Sci. USA 82:1766-1770; Press et al. (1987) "*Monoclonal Antibody 1F5 (anti-CD20) Serotherapy Of Human B cell Lymphomas*," Blood 69:584-591, each of which is incorporated herein by reference in its entirety), B1 (Nadler et al. (1981) "*A Unique Cell Surface Antigen Identifying Lymphoid Malignancies Of B Cell Origin*," J. Clin. Invest. 67:134-140, which is incorporated herein by reference in its entirety), ibritumomab (commercial name ZEVALIN™ (IDEC/Schering AG)), or tositumomab (commercial name BEXXAR®, Glaxo-SmithKline; Corixa); a CD20 antibody as described in U.S. Application Publication Nos. 2005-0025764, WO 05/000901, WO 04/035607, or WO 05/103081), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof, to prevent, treat, manage or ameliorate an inflammatory disorder (such as an autoimmune disease), or one or more symptoms thereof. In certain embodiments, the inflammatory disorder is Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

The invention also encompasses FcγRIIB-specific antibodies and/or CD20-specific antibodies of the invention (such as those FcγRIIB and CD20 antibodies referenced above), polynucleotides that encode the FcγRIIB-specific antibodies and/or CD20-specific antibodies of the invention, as well as compositions, vectors, host cells comprising the polynucleotides thereof, and combinations thereof to expressible levels of the FcγRIIB-specific antibodies and/or CD20 antibodies in the combinations and methods of the invention.

In one embodiment, the invention provides an isolated nucleic acid sequence encoding a heavy chain or a light chain of an antibody or a fragment thereof that specifically binds FcγRIIB with greater affinity than said antibody or a fragment thereof binds FcγRIIA. The invention also relates to a vector comprising said nucleic acid. The invention further provides a vector comprising a first nucleic acid molecule encoding a heavy chain and a second nucleic acid molecule encoding a light chain, said heavy chain and light chain being of an antibody or a fragment thereof that specifically binds FcγRIIB with greater affinity than said antibody or a fragment thereof binds FcγRIIA. In one specific embodiment, said vector is an expression vector. The invention further provides host cells containing the vectors of or polynucleotides encoding the antibodies of the invention. Preferably, the invention encompasses polynucleotides encoding heavy and light chains of the antibodies produced by the deposited hybridoma clones, 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, or portions thereof, e.g., CDRs, variable domains, etc., and humanized versions thereof.

The invention also provides a method of treating cancer in a patient having a cancer characterized by CD20, said method comprising administering to said patient a therapeutically effective amount of (A) an antibody or a fragment thereof that specifically binds FcγRIIB with greater affinity than said antibody or a fragment thereof binds FcγRIIA, and (B) an antibody or a fragment thereof that specifically binds CD20. The invention also provides a method of treating cancer in a patient having a cancer characterized by CD20, said method comprising administering to said patient a therapeutically effective amount of (A) an antibody or a fragment thereof that specifically binds FcγRIIB, particularly native human FcγRIIB with greater affinity than said antibody or a fragment thereof binds FcγRIIA, preferably native human FcγRIIA, and the constant domain of which further has an increased affinity for one or more Fc activation receptors, when the antibody is monomeric, such as FcγRIIIA, and (B) a CD20-specific antibody, an analog, derivative or an antigen-binding fragment thereof (e.g., one or more CDRs of a CD20-specific antibody). In one particular embodiment, said Fc activation receptor is FcγRIIIA In particular embodiments, the FcγRIIB antibody or fragment thereof is administered at a dose such that the antibody does not detectably bind to neutrophils.

In another preferred embodiment of the invention, the antibodies of the invention are useful for prevention or treatment of B cell malignancies, particularly non-Hodgkin's lymphoma or chronic lymphocytic leukemia. Accordingly, the present invention provides methods of treating, managing, preventing, or ameliorating a B cell malignancy by administering, either alone or in combination with one or more other therapeutics, (A) antibodies that specifically bind FcγRIIB, and, preferably, do not specifically bind FcγRIIA, as well as derivatives, analogs and antigen binding fragments of such antibodies, either alone or in combination with (B) a CD20-specific antibody, an analog, derivative or an antigen-binding fragment thereof (e.g., one or more CDRs of a CD20-specific antibody). In particular embodiments, the cancer of the subject is refractory to one or more standard or experimental therapies, particularly, to RITUXAN® treatment alone. The methods of the invention may be used for the treatment, management, prevention, or amelioration of B cell diseases, such as, B cell chronic lymphocytic leukemia (B-CLL), non-Hodgkin's lymphoma, diffuse large B cell lymphoma, follicular lymphoma with areas of diffuse large B cell lymphoma, small lymphocytic lymphoma, mantle cell lymphoma, and diffuse small cleaved cell lymphoma.

In another preferred embodiment of the invention, the anti-FcγRIIB and anti-CD20 antibodies are useful for prevention or treatment of inflammatory disorders, particularly rheumatoid arthritis. Accordingly, the present invention provides methods of treating, managing, preventing, or ameliorating an inflammatory disorder, such as an autoimmune disorder, or a symptom thereof by administering, either alone or in combination with one or more other therapeutics, (A) antibodies that specifically bind FcγRIIB, and, preferably, do not specifically bind FcγRIIA, as well as derivatives, analogs and antigen binding fragments of such antibodies, either alone or in combination with (B) a CD20-specific antibody, an analog, derivative or an antigen-binding fragment thereof (e.g., one or more CDRs of a CD20-specific antibody). In certain embodiments, the methods of the invention can be used for the treatment, management, prevention, or amelioration of an autoimmune disease, or a symptom thereof, wherein the autoimmune disease is Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis or ulcerative colitis.

In another embodiment, the invention provides for the use of a FcγRIIB-specific antibody conjugated to a therapeutic agent or drug, in combination with a CD20-specific antibody that may or may not be conjugated to a same or different therapeutic agent or drug. Examples of therapeutic agents which may be conjugated to an anti-FcγRIIB and/or anti-CD20 antibody or an antigen-binding fragment thereof include, but are not limited to, cytokines, toxins, radioactive elements, and antimetabolites.

In one embodiment, the invention provides for the administration of an FcγRIIB-specific antibody and an anti-CD20 antibody in combination with a standard or experimental treatment regimen for B cell malignancies (e.g., chemotherapy, radioimmunotherapy, or radiotherapy). Such combination therapy may enhance the efficacy of standard or experimental treatment. Examples of therapeutic agents that are particularly useful in combination with a FcγRIIB-specific antibody or an antigen-binding fragment thereof, and a CD20 specific antibody or an antigen binding fragment thereof, for the prevention, treatment, management, or amelioration of B cell malignancies, include, but are not limited to interferon-alpha and anti-cancer agents. Chemotherapeutic agents that can be used in combination with a FcγRIIB-specific antibody or an antigen-binding fragment thereof, and a CD20 specific antibody or an antigen binding fragment thereof, include, but are not limited to alkylating agents, antimetabolites, natural products, and hormones. The combination therapies of the invention enable lower dosages of combinations of an anti-FcγRIIB antibody or an antigen-binding fragment thereof, and a CD20 specific antibody or an antigen binding fragment thereof, and/or less frequent administration of anti-FcγRIIB antibody or an antigen-binding fragment thereof, and a CD20 specific antibody or an antigen binding fragment thereof, to a subject with a B cell malignancy, to achieve a therapeutic or prophylactic effect. Such doses and frequency of administration of the combinations of FcγRIIB and CD20 antibodies are decreased as compared to the doses and frequency of administration of either single antibody alone.

In another embodiment, the use of a combined therapy of an anti-FcγRIIB and an anti-CD20 antibody, or antigen-binding fragments thereof, prolongs the survival of a subject diagnosed with a B cell malignancy.

The invention further provides a pharmaceutical composition comprising (A) a therapeutically effective amount of the antibody or a fragment thereof that specifically binds FcγRIIB with greater affinity than said antibody or a fragment thereof binds FcγRIIA; (B) a CD20-specific antibody, or an antigen-binding fragment thereof; and (c) a pharmaceutically acceptable carrier.

In certain embodiments of the invention, pharmaceutical compositions are provided for use in accordance with the methods of the invention, said pharmaceutical compositions comprising (A) an anti-FcγRIIB antibody or an antigen-binding fragment thereof, (B) a CD20-specific antibody, an analog, derivative or an antigen-binding fragment thereof (e.g., one or more CDRs of a CD20-specific antibody), and (C) a pharmaceutically acceptable carrier, said antibodies provided in an amount effective to prevent, treat, manage, or ameliorate a B cell malignancy, an inflammatory disease, or one or more symptoms thereof. The invention also provides pharmaceutical compositions for use in accordance with the methods of the invention, said pharmaceutical compositions comprising an anti-FcγRIIB antibody or an antigen-binding fragment thereof, an anti-CD20 antibody, or antigen-binding fragment thereof, and a prophylactic or therapeutic agent, and a pharmaceutically acceptable carrier.

BRIEF DESCRIPTION OF THE DRAWINGS

FIG. 1A. Cells were co-stained with anti-CD20-FITC antibody and mouse IgG1 isotype control. FIG. 1B. Cells were co-stained with anti-CD20-FITC antibody and 3H7 antibody. C. Cells were co-stained with anti-CD20-FITC antibody and 2B6 antibody.

FIGS. 3A-3G: Effect of RITUXAN® and 2B6 variants on tumor growth in mice. FIG. 3A: Rituximab. FIG. 3B: ch2B6, ch2B6 N297Q, h2B6, and h2B6 YA. FIG. 3C: h2B6YA. FIG. 3D: h2B6YA 31/60. FIG. 3E: h2B6YA 38/60. FIG. 3F: h2B6YA 55/60. FIG. 3G. h2B6YA 71.

FIGS. 4A-4I: Ex vivo staining of Daudi for CD20 and CD32B. Daudi tumors were collected from mice treated with h2B6 (FIGS. 4B, 4E, 4H) or h2B6YA (FIGS. 4C, 4F, 4I). CD20 (FIGS. 4G, 4H, 4I) and CD32B (FIGS. 4D, 4E, 4F) expression was compared with those of Daudi cells expanded in vitro (FIGS. 4A, 4D, 4G).

FIG. 6A: Anti-CD32B antibody; 40× magnification. FIG. 6B: Anti-CD20 antibody; 40× magnification.

FIG. 7A: H-E staining; 10× magnification. A portion of a crypt (small arrow) and lymphatic nodules with germinal centers (long arrow) was seen. FIG. 7B: Anti-CD32B; 40× magnification. Positive cells in the follicles surrounding germinal centers. FIG. 7C: Anti-CD20; 40× magnification. Lymphatic follicles showed germinal center cells reacting with anti-CD20.

FIG. 8A: H-E staining; 4× magnification. Some lymphatic follicles with germinal centers were seen. FIG. 8B: Anti-CD32B; 4× magnification. Germinal centers were circumscribed by a ring of positive cells for CD32B. FIG. 8C: Anti-CD20; 4× magnification. Cells in the germinal centers reacted with anti-CD20.

FIGS. 9A-9B: Effect of a higher dose combined therapy comprising an anti-FcγRIIB antibody and anti-CD20 antibody on tumor growth in mice. FIG. 9A: Tumor volume in a xenograft B-lymphoma model after treatment with 30 ng/g body weight of FcγRIIB Ab alone, CD20 Ab alone, or a combination of FcγRIIB Ab+CD20 Ab. The FcγRIIB Ab+CD20 Ab combination was synergistic and reduced the tumor volume more dramatically than either antibody alone. FIG. 9B: The % of responders (complete responders (CR)+ partial responders (PR)) over the course of the study. A synergistic combination of FcγRIIB Ab+CD20 Ab resulted in 100% (complete (CR)+partial (PR)) responders by day 21.

FIGS. 10A-10B: Effect of a lower dose combined therapy comprising an anti-FCγRIIB antibody and anti-CD20 antibody on tumor growth in mice. FIG. 10A: Tumor volume in a xenograft B-lymphoma model after treatment with 1 µg/g body weight of CD20 Ab alone, FcγRIIB Ab alone, or a combination of FcγRIIB Ab+CD20 Ab. The FcγRIIB Ab+CD20 Ab combination was synergistic and reduced the tumor volume more dramatically than either antibody alone. FIG. 10B: The % of responders over the course of the study. A synergistic combination of FcγRIIB Ab+CD20 Ab resulted in 100% (complete (CR)+partial (PR)) responders by day 49.

FIG. 11: Depiction of the 8B5.3.4 VL nucleotide and amino acid sequence (SEQ ID NO:74 and SEQ ID NO:72, respectively).

FIG. 12: Depiction of the of the 8B5.3.4 VH nucleotide and amino acid sequence (SEQ ID NO:73 and SEQ ID NO:71, respectively).

DETAILED DESCRIPTION OF THE INVENTION

Definitions

Figure 1:
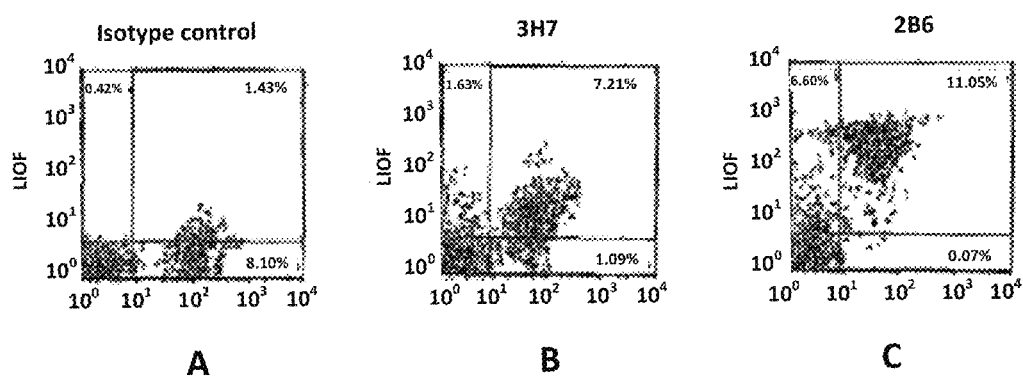
FIGS. 1A-1C: Monoclonal anti FcγRIIB antibodies and CD20 co-stain of human B lymphocytes. Cells from human blood ("buffy coat") were stained with anti-CD20-FITC conjugated antibody, to select the B lymphocytes population, as well as 3H7 and 2B6. The bound anti-FcγRIIB antibodies were detected with a goat anti-mouse-PE conjugated antibody.

As used herein, the term "specifically binds to FcγRIIB" and analogous terms refer to antibodies or fragments thereof (or any other FcγRIIB binding molecules) that specifically bind to FcγRIIB or a fragment thereof and do not specifically bind to other Fc receptors, in particular to FcγRIIA. Further it is understood to one skilled in the art, that an antibody that specifically binds to FcγRIIB, may bind through the variable domain or the constant domain of the antibody but that the anti-FcγRIIB antibodies of the invention benefit FcγRIIB through the variable domain. If the antibody that specifically binds to FcγRIIB binds through its variable domain, it is understood to one skilled in the art that it is not aggregated, i.e., is monomeric. An antibody that specifically binds to FcγRIIB may bind to other peptides or polypeptides with lower affinity as determined by, e.g., immunoassays, BIAcore, or other assays known in the art. Preferably, antibodies or fragments that specifically bind to FcγRIIB or a fragment thereof do not cross-react with other antigens. Antibodies or fragments that specifically bind to FcγRIIB can be identified, for example, by immunoassays, BIAcore, or other techniques known to those of skill in the art. An antibody or a fragment thereof binds specifically to a FcγRIIB when it binds to FcγRIIB with higher affinity than to any cross-reactive antigen as determined using experimental techniques, such as western blots, radioimmunoassays (RIA) and enzyme-linked immunosorbent assays (ELISAs). See, e.g., Paul, ed. (1989) FUNDAMENTAL IMMUNOLOGY 2$^{nd}$ Edition, Raven Press, New York at pages 332-336 for a discussion regarding antibody specificity.

As used herein, the term "native FcγRIIB" refers to FcγRIIB which is endogenously expressed and present on the surface of a cell. In some embodiments, "native FcγRIIB" encompasses a protein that is recombinantly expressed in a mammalian cell. Preferably, the native FcγRIIB is not expressed in a bacterial cell, i.e., *E. coli*. Most preferably the native FcγRIIB is not denatured as would be the case in Western blot analysis, i.e., it is in its biologically active conformation.

As used herein, the term "native FcγRIIA" refers to FcγRIIA which is endogenously expressed and present on the surface of a cell. In some embodiments, "native FcγRIIA" encompasses a protein that is recombinantly expressed in a mammalian cell. Preferably, the native FcγRIIA is not expressed in a bacterial cell, i.e., *E. coli*. Most preferably the native FcγRIIA is not denatured as would be the case in Western blot analysis, i.e., it is in its biologically active conformation.

As used herein, "administer" or "administration" refers to the act of injecting or otherwise physically delivering a substance as it exists outside the body (e.g., an antibody of the invention) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or symptoms thereof, are being treated, administration of the substance typically occurs after the onset of the disease or symptoms thereof. When a disease, or symptoms thereof, are being prevented, administration of the substance typically occurs before the onset of the disease or symptoms thereof.

As used herein, the term "analog" in the context of proteinaceous agents (e.g., proteins, polypeptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (A) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (B) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (C) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a polypeptide can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin et al. (1990) "*Methods For Assessing The Statistical Significance Of Molecular Sequence Features By Using General Scoring Schemes,*" Proc. Natl. Acad. Sci. U.S.A. 87:2264-2268, modified as in Karlin et al. (1993) "*Applications And Statistics For Multiple High-Scoring Segments In Molecular Sequences,*" Proc. Natl. Acad. Sci. U.S.A. 90:5873-5877. Such an algorithm is incorporated into the NBLAST and XBLAST programs of Altschul et al. (1990) "*Basic Local Alignment Search Tool,*" J. Mol. Biol. 215:403-410. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score=50, wordlength=3 to obtain amino acid sequences homologous to a protein molecule of the present invention. To obtain gapped alignments for comparison purposes, Gapped BLAST can be utilized as described in Altschul et al. (1997) "*Gapped BLAST and PSI-BLAST: A New Generation Of Protein Database Search Programs,*" Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous agent refers to a second organic or inorganic molecule which possess a similar or identical function as a first organic or inorganic molecule and is structurally similar to the first organic or inorganic molecule.

As used herein, the terms "antagonist" and "antagonists" refer to any protein, polypeptide, peptide, antibody, antibody fragment, large molecule, or small molecule (less than 10 kD) that blocks, inhibits, reduces or neutralizes a function, activity and/or expression of another molecule, such as that of FcγRIIB. In various embodiments, an antagonist reduces a function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

Throughout the numbering of residues in an IgG heavy chain is that of the EU index as in Kabat et al., SEQUENCES OF PROTEINS OF IMMUNOLOGICAL INTEREST, $5^{th}$ Ed. Public Health Service NIH, MD (1991), which is incorporated herein by reference. The "EU index as in Kabat" refers to the numbering of the human IgG1 EU antibody.

As used herein, the terms "B cell malignancies" and "B cell malignancy" refer to any B cell lymphoproliferative disorder. B cell malignancies include tumors of B cell origin. B cell malignancies include, but are not limited to, lymphomas, chronic lymphocytic leukemias, acute lymphoblastic leukemias, multiple myeloma, Hodgkin's and non-Hodgkin's disease, diffuse large B cell lymphoma, follicular lymphoma with areas of diffuse large B cell lymphoma, small lymphocytic lymphoma, mantle cell lymphoma, and diffuse small cleaved cell lymphoma.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen.

As used herein, the term "combination" or "combination of the invention" refer to compositions and/or other therapies comprising (A) an antibody, or antigen binding fragment thereof that immunospecifically binds to a CD20 polypeptide, and (B) an antibody, or antigen binding fragment thereof that immunospecifically binds to a FcγRIIB polypeptide. Any CD20 antibody or fragment thereof and/or FcγRIIB antibody, or fragment thereof described herein may be used in the combinations of the invention. In certain embodiments, the CD20 antibody and FcγRIIB antibody are administered simultaneously. In other embodiments the CD20 antibody and FcγRIIB antibody are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

As used herein, the term "derivative" in the context of polypeptides or proteins, including antibodies, refers to a polypeptide or protein that comprises an amino acid sequence which has been altered by the introduction of amino acid residue substitutions, deletions or additions. The term "derivative" as used herein also refers to a polypeptide or protein which has been modified, i.e., by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

The term "derivative" as used herein in conjunction with Fc RIIB refers to a polypeptide that comprises an amino acid sequence of a Fc RIIB polypeptide, a fragment of a Fc RIIB polypeptide, an antibody that immunospecifically binds to a Fc RIIB polypeptide, or an antibody fragment that immunospecifically binds to a Fc RIIB polypeptide, that has been altered by the introduction of amino acid residue substitutions, deletions or additions (i.e., mutations). In some embodiments, an antibody derivative or fragment thereof comprises amino acid residue substitutions, deletions or additions in one or more CDRs. The antibody derivative may have substantially the same binding, better binding, or worse binding when compared to a non-derivative antibody. In specific embodiments, one, two, three, four, or five amino acid residues of the CDR have been substituted, deleted or added (i.e., mutated). The term "derivative" as used herein in conjunction with Fc RIIB also refers to a Fc RIIB polypeptide, a fragment of a Fc RIIB polypeptide, an antibody that immunospecifically binds to a Fc RIIB polypeptide, or an antibody fragment that immunospecifically binds to a FcγRIIB polypeptide which has been modified, i.e., by the covalent attachment of any type of molecule to the polypeptide. For example, but not by way of limitation, a Fc RIIB polypeptide, a fragment of a Fc RIIB polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of a Fc RIIB polypeptide, a fragment of a Fc RIIB polypeptide, an antibody, or antibody fragment may be modified by chemical modifications using techniques known to those of skill in the art, including, but not limited to, specific chemical cleavage, acetylation, formulation, metabolic synthesis of tunicamycin, etc. Further, a derivative of a Fc RIIB polypeptide, a fragment of a Fc RIIB polypeptide, an antibody, or antibody fragment may contain one or more non-classical amino acids. In one embodiment, an antibody derivative possesses a similar or identical function as the parent antibody. In another embodiment, a derivative of an antibody, or antibody fragment has an altered activity when compared to an unaltered antibody. For example, a derivative antibody or fragment thereof can bind to its epitope more tightly or be more resistant to proteolysis.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "endogenous" in the context of a cellular protein refers to protein naturally occurring and/or expressed by the cell in the absence of recombinant manipulation; accordingly, the terms "endogenously expressed protein" or "endogenous protein" excludes cellular proteins expressed by means of recombinant technology.

As used herein, the term "epitope" refers to a region on an antigen molecule to which an antibody specifically binds.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide. Preferably, antibody fragments are epitope binding fragments.

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized", by the process of "humanization", because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that may be altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565, 332, 5,585,089, 5,766,886, and 6,407,213; and Padlan (1991) "*A Possible Procedure For Reducing The Immunogenicity Of Antibody Variable Domains While Preserving Their Ligand-Binding Properties*," Molecular Immunology 28(4/5):489-498; Studnicka et al. (1994) "*Human-Engineered Monoclonal Antibodies Retain Full Specific Binding Activity By Preserving Non-CDR Complementarity-Modulating Residues*," Protein Engineering 7:805-814; Roguska et al. (1994) "*Humanization Of Murine Monoclonal Antibodies Through Variable Domain Resurfacing*," Proc. Nat. Acad. Sci. 91:969-973; Tan et al. (2002) "'*Superhumanized*'

Antibodies: Reduction Of Immunogenic Potential By Complementarity-Determining Region Grafting With Human Germline Sequences: Application To An Anti-CD28," J. Immunol. 169:1119 1125; Caldas et al. (2000) "Design And Synthesis Of Germline-Based Hemi-Humanized Single-Chain Fv Against The CD18 Surface Antigen," Protein Eng. 13:353 360; Morea et al. (2000) "Antibody Modeling: Implications For Engineering And Design," Methods 20:267 279; Baca et al. (1997) "Antibody Humanization Using Monovalent Phage Display," J. Biol. Chem. 272:10678-10684; Baca et al. (1997) "Antibody Humanization Using Monovalent Phage Display," J. Biol. Chem. 272:10678-10684; Roguska et al. (1996) "A Comparison Of Two Murine Monoclonal Antibodies Humanized By CDR-Grafting And Variable Domain Resurfacing," Protein Eng. 9:895 904; Couto et al. (1995) "Designing Human Consensus Antibodies With Minimal Positional Templates," Cancer Res. 55 (23 Supp):5973s 5977s; Couto et al. (1995) "Anti-BA46 Monoclonal Antibody Mc3: Humanization Using A Novel Positional Consensus And In Vivo And In Vitro Characterization," Cancer Res. 55:1717 22; Sandhu (1994) "A Rapid Procedure For The Humanization Of Monoclonal Antibodies," Gene 150:409 410; Pedersen et al. (1994) "Comparison Of Surface Accessible Residues In Human And Murine Immunoglobulin Fv Domains. Implication For Humanization Of Murine Antibodies," J. Mol. Biol. 235:959 973; Jones et al. (1986) "Replacing The Complementarity-Determining Regions In A Human Antibody With Those From A Mouse," Nature 321:522-525; Riechmann et al. (1988) "Reshaping Human Antibodies For Therapy," Nature 332:323-327; and Presta (1992) "Antibody Engineering," Curr. Op. Biotech. 3:394-398.

As used herein, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., SEQUENCES OF PROTEINS OF IMMUNOLOGICAL INTEREST, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined.

As used herein, the term "immunomodulatory agent" and variations thereof including, but not limited to, immunomodulatory agents, refer to an agent that modulates a host's immune system. In certain embodiments, an immunomodulatory agent is an immunosuppressant agent. In certain other embodiments, an immunomodulatory agent is an immunostimulatory agent Immunomodulatory agents include, but are not limited to, small molecules, peptides, polypeptides, fusion proteins, antibodies, inorganic molecules, mimetic agents, and organic molecules.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the term "native FcγRIIB" refers to FcγRIIB which is endogenously expressed and present on the surface of a cell. In some embodiments, "native FcγRIIB" encompasses a protein that is recombinantly expressed in a mammalian cell. Preferably, the native FcγRIIB is not expressed in a bacterial cell, i.e., E. coli. Most preferably the native FcγRIIB is not denatured, i.e., it is in its biologically active conformation.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "prevent", "preventing" and "prevention" refer to the prevention of the occurrence and/or recurrence or onset of one or more symptoms of a disorder in a subject resulting from the administration of a prophylactic or therapeutic agent.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of a B cell related disease or disorder, or the occurrence of such in a patient, including but not limited to those predisposed to such a B cell related disease or disorder.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art, see, e.g., the Physicians' Desk Reference ($56^{th}$ ed., 2002), which is incorporated herein by reference in its entirety.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of sFv see Pluckthun in THE PHARMACOLOGY OF MONOCLONAL ANTIBODIES, vol. 113, Rosenburg and Moore eds. Springer-Verlag, New York, pp. 269-315 (1994). In specific embodiments, scFvs include bi-specific scFvs and humanized scFvs.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, a "therapeutically effective amount" refers to that amount of the therapeutic agent sufficient to treat or manage a disease or disorder such as a B cell associated disease or disorder. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease.

The term "synergistic" as used herein refers to a combination of therapies (e.g., use of an FcγRIIB antibody and an anti-CD20 antibody) which is more effective than the additive effects of any two or more single therapies. For example, a synergistic effect of a combination of antibodies permits the use of lower dosages of one or more of the antibodies and/or less frequent administration of said antibodies to a subject. The ability to utilize lower dosages of antibodies and/or to administer said antibodies less frequently reduces the toxicity associated with the administration of said therapies to a subject without reducing the efficacy of said therapies in the prevention, management, treatment or amelioration of a given disease, such as a B cell malignancy. In addition, a synergistic effect can result in improved efficacy of therapies in the prevention, management, treatment or amelioration of a given disease, such as a B cell malignancy. Finally, synergistic effects of a combination of therapies may avoid or reduce adverse or unwanted side effects associated with the use of any single therapy.

As used herein, the terms "treat," "treating" and "treatment" refer to the eradication, reduction or amelioration of symptoms of a disease or disorder such as a B cell associated disease or disorder. In certain embodiments, such terms refer to the minimizing or delaying the spread of or worsening of disease by administering one or more therapeutic agents to a subject with such a disease. In other embodiments, such terms refer to elimination of disease causing cells.

As used herein, the term "in combination" refers to the use of more than one prophylactic and/or therapeutic agents, such as anti FcγRIIB antibodies and anti CD20 antibodies. The use of the term "in combination" does not restrict the order in which prophylactic and/or therapeutic agents are administered to a subject with a disorder, e.g., a B cell disorder. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

A. FcγRIIB-Specific and CD-20 Specific Antibodies

The present invention encompasses methods and compositions comprising combinations of antibodies, wherein a first antibody in the combination is an anti-CD20 antibody (preferably a monoclonal antibody) or an antigen binding fragment thereof, and wherein a second antibody in the combination is an antibody (preferably a monoclonal antibody) or fragment thereof that specifically binds FcγRIIB, preferably human FcγRIIB, more preferably native human FcγRIIB with a greater affinity than said second antibody or fragment thereof binds FcγRIIA, preferably human FcγRIIA, more preferably native human FcγRIIA. Representative FcγRIIB antibodies are disclosed in U.S. Pat. No. 7,425,620; U.S. Patent Application Nos. 2005-0260213; and 2006-0013810, herein expressly incorporated by reference in their entirety.

The present invention encompasses the administration of (A) a FcγRIIB-specific antibody, an analog, derivative or an antigen-binding fragment thereof (e.g., one or more CDRs of a FcγRIIB-specific antibody) and (B) a CD20 antibody, an analog derivative or an antigen binding fragment thereof (e.g., one or more CDRs of a CD20 antibody) in the prevention, treatment, management or amelioration of a diseases, such as cancer, in particular, a B cell malignancy, or one or more symptoms thereof. Preferably, the FcγRIIB antibodies of the combination bind the extracellular domain of native human FcγRIIB. In certain embodiments, the FcγRIIB antibodies or fragments thereof in the combination bind to FcγRIIB with an affinity greater than two-fold, four fold, 6 fold, 10 fold, 20 fold, 50 fold, 100 fold, 1000 fold, $10^4$ fold, $10^5$ fold, $10^6$ fold, $10^7$ fold, or $10^8$ fold than said antibodies or fragments thereof bind FcγRIIA. In yet other embodiments, the invention encompasses the use of combinations of CD20 antibodies and FcγRIIB antibodies, wherein the FcγRIIB antibodies bind exclusively to FcγRIIB and have no affinity for FcγRIIA using standard methods known in the art and disclosed herein. In a preferred embodiment, the CD20 and/or FcγRIIB antibodies are human or humanized.

In certain embodiments, the invention relates to a combination of a CD20 antibody and an isolated FcγRIIB antibody or a fragment thereof that specifically binds FcγRIIB with a greater affinity than said FcγRIIB antibody or fragment thereof binds FcγRIIA, wherein the constant domain of said FcγRIIB antibody further has an enhanced affinity for at least one or more Fc activation receptors. In yet another specific embodiment, said Fc activation receptor is FcγRIII.

In some embodiments, the FcγRIIB antibodies in the combination derivative or an antigen binding fragment thereof (e.g., one or more CDRs of a CD20 antibody) do not bind Fc activation receptors, e.g., FcγIIIA, FcγIIIB, etc. In one embodiment, the FcγRIIB-specific antibody in the combination is not the monoclonal antibody designated KB61, as disclosed in Pulford et al. (1986) "*A New Monoclonal Antibody* (KB61) *Recognizing A Novel Antigen Which Is*

*Selectively Expressed On A Subpopulation Of Human B Lymphocytes,*" Immunology 57:71-76 or the monoclonal antibody designated MAbII8D2 as disclosed in Weinrich et al. (1996) "*Epitope Mapping Of New Monoclonal Antibodies Recognizing Distinct Human FcRII (CD32) Isoforms,*" Hybridoma 15: 109-116. In a specific embodiment, a FcγRIIB-specific antibody in the combination does not bind to the same epitope and/or does not compete with binding with the monoclonal antibody KB61 or II8D2. In one embodiment, the FcγRIIB-specific antibody of the combination does not bind the amino acid sequence SDPNFSI corresponding to positions 135-141 of FcγRIIb2 isoform.

In one embodiment, the FcγRIIB antibody or a fragment thereof of the combinations of the invention blocks the IgG binding site of FcγRIIB and blocks the binding of aggregated labeled IgGs to FcγRIIB in, for example, a blocking ELISA assay. In one particular embodiment, said FcγRIIB antibody or a fragment thereof blocks the binding of aggregated labeled IgGs in an ELISA blocking assay by at least 50%, 60%, 70%, 80%, 90%, 95%, 99%, or 99.9%. In yet another particular embodiment, the FcγRIIB antibody or a fragment thereof of a combination of the invention completely blocks the binding of said aggregated labeled IgG in said ELISA assay.

In some embodiments, an FcγRIIB antibody or a fragment thereof of the combination of the invention blocks the IgG binding site of FcγRIIB and blocks the binding of aggregated labeled IgG to FcγRIIB, as determined by a double-staining FACS assay.

In one embodiment, the FcγRIIB antibodies in the combination modulate (i.e., agonize or antagonize) the activity of FcγRIIB. In some embodiments, the FcγRIIB antibodies of the combinations of the invention agonize at least one activity of FcγRIIB, i.e., elicit signaling. Although not intending to be bound by any mechanism of action, agonistic FcγRIIB antibodies of the combinations of the invention may mimic clustering of FcγRIIB leading to dampening of the activating response to FcγR ligation and inhibition of cellular responsiveness.

In a particular embodiment, the FcγRIIB antibodies of the combination with a CD20 antibody, or fragments thereof agonize at least one activity of FcγRIIB. In one embodiment of the invention, said activity is inhibition of B cell receptor-mediated signaling. In another embodiment, the agonistic FcγRIIB antibodies of the combination inhibit activation of B cells, B cell proliferation, antibody production, intracellular calcium influx of B cells, cell cycle progression, or activity of one or more downstream signaling molecules in the FcγRIIB signal transduction pathway. In yet another embodiment, the agonistic FcγRIIB antibodies of the combination enhance phosphorylation of FcγRIIB or SHIP recruitment. In a further embodiment of the invention, the FcγRIIB agonistic antibodies of the combination inhibit MAP kinase activity or Akt recruitment in the B cell receptor-mediated signaling pathway. In another embodiment, the FcγRIIB agonistic antibodies of the combination agonize FcγRIIB-mediated inhibition of FcεRI signaling.

In some embodiment, antibodies of the combinations of the invention inhibit FcεRI-induced mast cell activation. In one embodiment, the anti-FcγRIIB antibodies of the combinations of the invention inhibit FcγRIIA-mediated macrophage activation in monocytic cells. In other embodiments, the anti-FcγRIIB antibodies of the combinations of the invention inhibit B cell receptor mediated signaling.

In a particular embodiment, the FcγRIIB antibodies of the combinations of the invention inhibit FcεRI-induced mast cell activation, calcium mobilization, degranulation, cytokine production, or serotonin release. In another embodiment, the FcγRIIB agonistic antibodies of the combinations stimulate phosphorylation of FcγRIIB, stimulate recruitment of SHIP, stimulate SHIP phosphorylation and its association with Shc, or inhibit activation of MAP kinase family members (e.g., Erk1, Erk2, JNK, p38, etc.). In yet another embodiment, the FcγRIIB agonistic antibodies of the combination enhance tyrosine phosphorylation of p62dok and its association with SHIP and rasGAP. In another embodiment, the agonistic antibodies of the invention inhibit FcγR-mediated phagocytosis in monocytes or macrophages.

In another embodiment, the FcγRIIB antibodies of the combinations of the invention antagonize at least one activity of FcγRIIB, i.e., block signaling. For example, the FcγRIIB antibodies of the combinations of the invention block the binding of aggregated IgGs to FcγRIIB.

In some embodiments, the FcγRIIB antibodies of the combination with a CD20 antibody, or fragments thereof antagonize at least one activity of FcγRIIB. In one embodiment, said activity is activation of B cell receptor-mediated signaling. In a particular embodiment, the FcγRIIB antagonistic antibodies of the combination enhance B cell activity, B cell proliferation, antibody production, intracellular calcium influx, or activity of one or more downstream signaling molecules in the FcγRIIB signal transduction pathway. In yet another particular embodiment, the FcγRIIB antagonistic antibodies of the combination decrease phosphorylation of FcγRIIB or SHIP recruitment. In a further embodiment, the FcγRIIB antagonistic antibodies of the combination enhance MAP kinase activity or Akt recruitment in the B cell receptor mediated signaling pathway. In another embodiment, the antagonistic FcγRIIB antibodies of the combination antagonize FcγRIIB-mediated inhibition of FcεRI signaling. In a particular embodiment, the FcγRIIB antagonistic antibodies of the combination enhance FcεRI-induced mast cell activation, calcium mobilization, degranulation, cytokine production, or serotonin release. In another embodiment, the FcγRIIB antagonistic antibodies of the combination inhibit phosphorylation of FcγRIIB, inhibit recruitment of SHIP, inhibit SHIP phosphorylation and its association with Shc, enhance activation of MAP kinase family members (e.g., Erk1, Erk2, JNK, p38, etc.). In yet another embodiment, the FcγRIIB antagonistic antibodies of the combination inhibit tyrosine phosphorylation of p62dok and its association with SHIP and rasGAP. In another embodiment, the FcγRIIB antagonistic antibodies of the combination enhance FcγR-mediated phagocytosis in monocytes or macrophages. In another embodiment, the FcγRIIB antagonistic antibodies of the combination prevent phagocytosis, clearance of opsonized particles by splenic macrophages.

FcγRIIB and/or CD20 antibodies used in the combinations of the invention include, but are not limited to, monoclonal antibodies, synthetic antibodies, recombinantly produced antibodies, multispecific antibodies, human antibodies, humanized antibodies, chimeric antibodies, camelized antibodies, single-chain Fvs (scFv), single chain antibodies, Fab fragments, F(ab') fragments, disulfide-linked Fvs (sdFv), intrabodies, and epitope-binding fragments of any of the above, and each FcγRIIB or CD20 antibody may be independently selected as such. In particular, antibodies used in the combination compositions and methods of the present invention include immunoglobulin molecules and immunologically active portions of immunoglobulin molecules. For example, in some embodiments, the FcγRIIB antibody contains an antigen binding site that immunospecifically binds to FcγRIIB with greater affinity than said immunoglobulin molecule binds FcγRIIA. Antibody analogs may also include FcγRIIB-specific T cell receptors, for example, chimeric T cell receptors (see, e.g., U.S. Pat. No. 7,446,190), a single-chain T cell receptor linked to a single-chain antibody (see, e.g., U.S. Pat. No. 6,534,633), and protein scaffolds (see, e.g., U.S. Pat. No. 6,818,418).

The FcγRIIB and/or CD20 antibodies used in the compositions and methods of the invention can be from any animal origin including birds and mammals (e.g., human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The FcγRIIB and/or CD20 antibodies used in the compositions and methods of the present invention can be monospecific, bispecific, trispecific or of greater multispecificity. For example, FcγRIIB multispecific antibodies may immunospecifically bind to different epitopes of FcγRIIB or immunospecifically bind to both an epitope of FcγRIIB as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al. (1992) "*Formation Of A Bispecific Antibody By The Use Of Leucine Zippers*," J. Immunol. 148:1547-1553; Todorovska et al. (2001) "*Design And Application Of Diabodies, Triabodies And Tetrabodies For Cancer Targeting*," Journal of Immunological Methods, 248:47-66.

In particular embodiments, the antibodies of the invention are multi-specific with specificities for FcγRIIB and for CD20.

In one particular embodiment, an FcγRIIB antibody used in combination with a CD20 antibody is derived from a mouse monoclonal antibody produced by clone 2B6, 3H7, or 8B5.3.4, having ATCC accession numbers PTA-4591, PTA-4592, and PTA-7610, respectively. Hybridomas producing antibodies 2B6, 3H7, and 8B5.3.4 have been deposited with the American Type Culture Collection (10801 University Blvd., Manassas, Va. 20110-2209) on Aug. 13, 2002 (2B6 and 3H7) and May 23, 2006 (8B5.3.4) under the provisions of the Budapest Treaty on the International Recognition of the Deposit of Microorganisms for the Purposes of Patent Procedures, and assigned accession numbers PTA-4591 (for hybridoma producing 2B6), PTA-4592 (for hybridoma producing 3H7), and PTA-7610 (for hybridoma producing 8B5.3.4) respectively, and are incorporated herein by reference. In a specific embodiment, the combinations comprise a CD20 antibody and an FcγRIIB antibody with the heavy chain having the amino acid sequence of:

```
                                      (SEQ ID NO: 28)
QVQLQQPVTE LVRPGASVML SCKASDYPFT

NYWIHWVKQR PGQGLEWIGV IDPSDTYPNY

NKKFKGKATL TVVVSSSTAY MQLSSLTSDD

SAVYYCARNG DSDYYSGMDY WGQGTSVTVS S;
or
``` heavy chain having the amino acid sequence of:

```
                                      (SEQ ID NO: 70)
QVQLVQSGAE VKKPGASVKV SCKASGYTFT

NYWIHWVRQA PGQGLEWIGV IDPSDTYPNY

NKKFKGRVTM TVDTSTSTAY MELRSLRSDD

TAVYYCARNG DSDYYSGMDY WGQGTTVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPELLG

GPSVFLLPPK PKDTLMISRT PEVTCVVVDV SHEDPEVKFN

WYVDGVEVHN AKTKPPEEQY NSTLRVVSIL

TVLHQDWLNG KEYKCKVSNK ALPAPIEKTI

SKAKGQPREP QVYTLPPSRD ELTKNQVSLT CLVKGFYPSD

IAVEWESNGQ PENNYKTTPL VLDSDGSFFL YSKLTVDKSR

WQQGNVFSCS VMHEALHNHY TQKSLSLSPG K;
and
``` a light chain having the amino acid sequence of:

```
                                      (SEQ ID NO: 26)
DILLTQSPAI LSVSPGERVS FSCRTSQSIG TNIHWYQQRT

NGFPRLLIKN VSESISGIPS RFSGSGSGTD FILSINSVES

EDIADYYCQQ SNTWPFTFGG GTKLEIK;
or
``` a light chain having the amino acid sequence of:

```
                                      (SEQ ID NO: 66)
EIVLTQSPDF QSVTPKEKVT FTCRTSQSIG TNIHWYQQKP

DQSPKLLIKE VSESISGVPS RFSGSGSGTD FTLTINSLEA

EDAATYYCQQ SNTWPFTFGG GTKVEIKRTV AAPSVFIFPP

SDEQLKSGTA SVVCLLNNFY PREAKVQWKV

DNALQSGNSQ ESVTEQDSKD STYSLSSTLT LSKADYEKHK

VYACEVTHQG LSSPVTKSFN RGEC.
```

In a specific embodiment, the combinations comprise a CD20 antibody and an FcγRIIB antibody with the heavy chain having the amino acid sequence of SEQ ID NO:68 and the light chain having the amino acid sequence of SEQ ID NO:62. In one embodiment, the combinations comprise a CD20 antibody and an FcγRIIB antibody with the heavy chain having the amino acid sequence of:

```
                                      (SEQ ID NO: 71)
EVKLEESGGG LVQPGGSMKL SCEASGFTFS

DAWMDWVRQS PEKGLEWVAE IRNKAKNHAT

YYAESVIGRF TISRDDSKSS VYLQMNSLRA EDTGIYYCGA

LGLDYWGQGT TLTVSS
``` and the light chain having the amino acid sequence of:

(SEQ ID NO: 72)
DIQMTQSPSS LLAALGERVS LTCRASQEIS GYLSWLQQKP

DGTIKRLIYA ASTLDSGVPK RFSGSESGSD YSLTISSLES

EDFADYYCLQ YFSYPLTFGA GTKLELK.

In a preferred embodiment, the FcγRIIB antibodies of the combination are human or have been humanized, preferably a humanized version of the antibody produced by clone 3H7, 2B6, or 8B5.3.4.

The invention also encompasses the use of other FcγRIIB antibodies in combination with a CD20 antibody, preferably monoclonal antibodies or fragments thereof that specifically bind Fc RIIB, preferably human Fc RIIB, more preferably native human Fc RIIB, that are derived from clones including but not limited to 1D5, 2E1, 2H9, 2D11, and 1F2 having ATCC Accession numbers, PTA-5958, PTA-5961, PTA-5962, PTA-5960, and PTA-5959, respectively. Hybridomas producing the above-identified clones were deposited under the provisions of the Budapest Treaty with the American Type Culture Collection (10801 University Blvd., Manassas, Va. 20110-2209) on May 7, 2004, and are incorporated herein by reference. In preferred embodiments, the antibodies described above are chimerized or humanized.

In a specific embodiment, an FcγRIIB antibody used in combination with a CD20 antibody in the compositions and methods of the present invention is an antibody or an antigen-binding fragment thereof (e.g., comprising one or more complementarily determining regions (CDRs), preferably all 6 CDRs) of the antibody produced by clone 2B6, 3H7, or 8B5.3.4 with ATCC accession numbers PTA-4591, PTA-4592, and PTA-7610, respectively (e.g., the heavy chain CDR3). In a specific embodiment, an FcγRIIB antibody used in combination with a CD20 antibody in the compositions and methods of the present invention is an antibody or an antigen-binding fragment thereof (e.g., comprising one or more complementarily determining regions (CDRs), preferably all 6 CDRs) of the antibody produced by clone 1D5, 2E1, 2H9, 2D11, and 1F2 having ATCC Accession numbers, PTA-5958, PTA-5961, PTA-5962, PTA-5960, and PTA-5959, respectively (e.g., the heavy chain CDR3). In another embodiment, an FcγRIIB antibody used in combination with a CD20 antibody in the compositions and methods of the present invention binds to the same epitope as the mouse monoclonal antibody produced from clone 2B6, 3H7, or 8B5.3.4 with ATCC accession numbers PTA-4591, PTA-4592, and PTA-7610, respectively and/or competes with the mouse monoclonal antibody produced from clone 2B6, 3H7, or 8B5.3.4 with ATCC accession numbers PTA-4591, PTA-4592, and PTA-7610, respectively as determined, e.g., in an ELISA assay or other appropriate competitive immunoassay, and also binds FcγRIIB with a greater affinity than said antibody or a fragment thereof binds FcγRIIA. In another embodiment, an FcγRIIB antibody used in combination with a CD20 antibody in the compositions and methods of the present invention binds to the same epitope as the mouse monoclonal antibody produced from clone 1D5, 2E1, 2H9, 2D11, and 1F2 having ATCC Accession numbers, PTA-5958, PTA-5961, PTA-5962, PTA-5960, and PTA-5959, respectively, as determined, e.g., in an ELISA assay or other appropriate competitive immunoassay, and also binds FcγRIIB with a greater affinity than said antibody or a fragment thereof binds FcγRIIA.

The present invention also encompasses combinations of a CD20 antibody and one or more FcγRIIB antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. The present invention further encompasses combinations of a CD20 antibody and one or more FcγRIIB antibodies or fragments thereof that specifically bind FcγRIIB with greater affinity than said antibody or fragment thereof binds FcγRIIA, said FcγRIIB antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. The determination of percent identity of two amino acid sequences can be determined by any method known to one skilled in the art, including BLAST protein searches.

The present invention also encompasses the use of combinations of a CD20 antibody and/or one or more FcγRIIB antibodies or antibody fragments that specifically bind FcγRIIB with greater affinity than said antibodies or fragments thereof binds FcγRIIA, wherein said FcγRIIB antibodies or antibody fragments are encoded by a nucleotide sequence that hybridizes to the nucleotide sequence of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, under stringent conditions. In a preferred embodiment, the invention provides combinations of a CD20 antibody and/or one or more FcγRIIB antibodies or fragments thereof that specifically bind FcγRIIB with greater affinity than said antibodies or fragments thereof bind FcγRIIA, said FcγRIIB antibodies or antibody fragments comprising a variable light chain and/or variable heavy chain encoded by a nucleotide sequence that hybridizes under stringent conditions to the nucleotide sequence of the variable light chain and/or variable heavy chain of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, under stringent conditions. In another preferred embodiment, the invention provides combinations of a CD antibody and/or one or more FcγRIIB antibodies or fragments thereof that specifically bind FcγRIIB with greater affinity than said antibodies or fragments thereof bind FcγRIIA, said FcγRIIB antibodies or antibody fragments comprising one or more CDRs encoded by a nucleotide sequence that hybridizes under stringent conditions to the nucleotide sequence of one or more CDRs of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 CURRENT PROTOCOLS IN MOLECULAR BIOLOGY, vol. 1, Green Publishing Associates, Inc. and John Wiley and Sons, Inc., NY at pages 6.3.1 to 6.3.6 and 2.10.3, incorporated herein by reference).

The methods and compositions of the invention also include combinations of one or more FcγRIIB antibodies or fragments thereof and one or more antibodies that specifically bind CD20. For example, the anti-CD20 antibody may be rituximab (2B8, commercial name RITUXAN® (IDEC/Genentech; Roche/Zettyaku; Xoma) (see International Patent Application Publication No. WO 02/096948 (heavy chain being SEQ ID NO:4 and light chain SEQ ID NO:6 of that publication and NCBI accession Nos. AX556949 and AX709550, which are deposits of plasmids encoding the heavy and light chains, respectively; U.S. Pat. Nos. 5,736,137 and 7,151,164, all of which are incorporated by reference herein in their entireties), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof. The anti-CD20 antibody may also be derived from the mouse-human chimeric anti-CD20 monoclonal antibody 2H7 (see Liu et al. (1987) "*Production Of A Mouse-Human Chimeric Monoclonal Antibody To CD20 With Potent Fc-Dependent Biologic Activity*," J. Immunol. 139: 3521-3526; Clark et al. (1985) "*Role Of The Bp35 Cell Surface Polypeptide In Human B-Cell Activation*," Proc. Natl. Acad. Sci. USA 82:1766-1770; U.S. Pat. No. 5,500,400; U.S. Application Publication Nos. 2006-0024300 and 2006-0034835, each of which is incorporated herein by reference in its entirety), 1F5 (Clark et al. (1985) "*Role Of The Bp35 Cell Surface Polypeptide In Human B-Cell Activation*," Proc. Natl. Acad. Sci. USA 82:1766-1770; Press et al. (1987) "*Monoclonal Antibody 1F5 (anti-CD20) Serotherapy Of Human B cell Lymphomas*," Blood 69:584-591, each of which is incorporated herein by reference in its entirety), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof. Other exemplary anti-CD20 antibodies that may be used in the combination therapies of the invention include, 1F5 (Clark et al. (1985) "*Role Of The Bp35 Cell Surface Polypeptide In Human B-Cell Activation*," Proc. Natl. Acad. Sci. USA 82:1766-1770; Press et al. (1987) "*Monoclonal Antibody 1F5 (anti-CD20) Serotherapy Of Human B cell Lymphomas*," Blood 69:584-591, each of which is incorporated herein by reference in its entirety), B1 (Nadler et al. (1981) "*A Unique Cell Surface Antigen Identifying Lymphoid Malignancies Of B Cell Origin*," J. Clin. Invest. 67:134-140, which is incorporated herein by reference in its entirety), ibritumomab (commercial name ZEVALIN™ (IDEC/Schering AG)), or tositumomab (commercial name BEXXAR®, Glaxo-SmithKline; Corixa); a CD20 antibody as described in U.S. Application Publication Nos. 2005-0025764, WO 05/000901, WO 04/035607, or WO 05/103081), or any analogs, derivatives, variants or antigen-binding fragments thereof of the above-referenced antibodies (e.g., one or more CDRs of a CD20-specific antibody), including chimeric, humanized or other engineered versions thereof, fully human versions thereof, and/or Fc variants thereof.

As those skilled in the art will appreciate, any one or more FcγRIIB antibodies disclosed herein may be used in combination with any one or more CD20 antibodies disclosed herein for the compositions and methods of the invention.

The constant domains of the FcγRIIB and/or CD20 antibodies may be selected with respect to the proposed function of the antibody, in particular with regard to the effector function which may be required. In some embodiments, the constant domains of the antibodies are human IgA, IgE, IgG or IgM domains.

The FcγRIIB and/or CD20 antibodies used in the compositions and methods of the invention include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Further, the FcγRIIB and/or CD20 antibodies of the invention can, in turn, be utilized to generate anti-idiotype antibodies using techniques well known to those skilled in the art. (See, e.g., Greenspan et al. (1989) "*Cooperative Binding Of Two Antibodies To Independent Antigens By An Fc-Dependent Mechanism*," FASEB J. 7:437-444; and Nissinoff (1991) "*Idiotypes: Concepts And Applications*," J. Immunol. 147:2429-2438). The invention provides methods employing the use of polynucleotides comprising a nucleotide sequence encoding an antibody of the invention or a fragment thereof.

The present invention encompasses FcγRIIB and/or CD20 single domain antibodies, including camelized single domain antibodies (See e.g., Muyldermans et al. (2001) "*Recognition Of Antigens By Single-Domain Antibody Fragments: The Superfluous Luxury Of Paired Domains*," Trends Biochem. Sci. 26:230-235; Nuttall et al. (2000) "*Immunoglobulin VH Domains And Beyond: Design And Selection Of Single-Domain Binding And Targeting Reagents*," Cur. Pharm. Biotech. 1:253-263; Reichmann et al. (1999) "*Single Domain Antibodies: Comparison Of Camel VH And Camelised Human VH Domains*," J. Immunol. Meth. 231:25-38; International Publication Nos. WO 94/04678 and WO 94/25591; U.S. Pat. No. 6,005,079; which are incorporated herein by reference in their entireties). In one embodiment, the present invention provides FcγRIIB and/or CD20 single domain antibodies comprising two VH domains with modifications such that single domain antibodies are formed.

The compositions and methods of the present invention also encompass the use of FcγRIIB and/or CD20 antibodies or fragments thereof in combination, wherein the FcγRIIB antibody and/or CD20 antibody have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the FcγRIIB and/or CD20 antibodies in the combinations of the invention, or fragments thereof, in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. FcγRIIB and/or CD20 antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The FcγRIIB and/or CD20 antibodies in the combinations of the invention may be engineered by methods described in Ward et al. to increase biological half-lives (See U.S. Pat. No. 6,277,375 B1). For example, FcγRIIB and/or CD20 antibodies in the combinations of the invention may be engineered in the Fc-hinge domain to have increased in vivo or serum half-lives.

FcγRIIB and/or CD20 antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The FcγRIIB and/or CD20 antibodies in the combinations of the invention can also be modified by the methods and coupling agents described by Davis et al. (See U.S. Pat. No. 4,179,337) in order to provide compositions that can be injected or otherwise administered into the mammalian circulatory system with substantially no immunogenic response.

The present invention also encompasses the use of FcγRIIB and/or CD20 antibodies or antibody fragments comprising the amino acid sequence of any of the FcγRIIB and/or CD20 antibodies, respectively, with mutations (e.g., one or more amino acid substitutions) in the framework or CDR regions. Preferably, mutations in these antibodies maintain or enhance the avidity and/or affinity of the antibodies for Fc RIIIB or CD20 to which they immunospecifically bind. Standard techniques known to those skilled in the art (e.g., immunoassays) can be used to assay the affinity of an antibody for a particular antigen.

The invention further encompasses methods of modifying an effector function of an FcγRIIB or CD20 antibody of the combination, wherein the method comprises modifying the carbohydrate content of the antibody using the methods disclosed herein or known in the art.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

For some uses, including in vivo use of FcγRIIB and/or CD20 antibodies in humans and in vitro detection assays, it may be preferable to use human, chimeric or humanized antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

B. Humanized Antibodies

In preferred embodiments, the FcγRIIB antibody is a humanized antibody, the CD20 antibody is a humanized antibody, or both the FcγRIIB antibody and CD20 antibody are humanized antibodies. A humanized antibody is an antibody, a variant or a fragment thereof which is capable of binding to a predetermined antigen and which comprises a framework region having substantially the amino acid sequence of a human immunoglobulin and a CDR having substantially the amino acid sequence of a non-human immunoglobulin. A humanized FcγRIIB specific antibody or humanized CD20-specific antibody may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized FcγRIIB and/or CD20 antibody also comprises at least a portion of an immunoglobulin constant region (Fc), typically that of a human immunoglobulin. The constant domains of the humanized antibodies may be selected with respect to the proposed function of the antibody, in particular the effector function which may be required. In some embodiments, the constant domains of the humanized antibodies are human IgA, IgE, IgG or IgM domains. In a specific embodiment, human IgG constant domains, especially of the IgG1 and IgG3 isotypes are used, when the humanized antibodies are intended for therapeutic uses and antibody effector functions are needed. In alternative embodiments, IgG2 and IgG4 isotypes are used when the humanized antibody is intended for therapeutic purposes and antibody effector function is not required. Humanized FcγRIIB specific antibodies that can be used in the combinations of the invention with an anti-CD20 antibody are disclosed in U.S. Application Publication No. 2006-0013810, published Jan. 19, 2006, which is incorporated herein by reference in its entirety.

In some embodiments, the antibody contains both the light chain as well as at least the variable domain of a heavy chain. In other embodiments, the antibody may further comprise one or more of the CH1, hinge, CH2, CH3, and CH4 regions of the heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. In some embodiments, the constant domain is a complement fixing constant domain where it is desired that the humanized antibody exhibit cytotoxic activity, and the class is typically IgG$_1$. In other embodiments, where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan (1991) "*A Possible Procedure For Reducing The Immunogenicity Of Antibody Variable Domains While Preserving Their Ligand-Binding Properties*," Molecular Immunology 28(4/5):489-498; Studnicka et al. (1994) "*Human-Engineered Monoclonal Antibodies Retain Full Specific Binding Activity By Preserving Non-CDR Complementarity-Modulating Residues*," Protein Engineering 7:805-814; and Roguska et al. (1994) "*Humanization Of Murine Monoclonal Antibodies Through Variable Domain Resurfacing*," Proc. Nat. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al. (2002) "*'Superhumanized' Antibodies: Reduction Of Immunogenic Potential By Complementarity-Determining Region Grafting With Human Germline Sequences: Application To An Anti-CD28*," J. Immunol. 169:1119 1125, Caldas et al. (2000) "*Design And Synthesis Of Germline-Based Hemi-Humanized Single-Chain Fv Against The CD18 Surface Antigen*," Protein Eng. 13:353 360, Morea et al. (2000) "*Antibody Modeling: Implications For Engineering And Design*," Methods 20:267 279; Baca et al. (1997) "*Antibody Humanization Using Monovalent Phage Display*," J. Biol. Chem. 272:10678-10684, Roguska et al. (1996) "*A Comparison Of Two Murine Monoclonal Antibodies Humanized By CDR-Grafting And Variable Domain Resurfacing*," Protein Eng. 9:895 904, Couto et al. (1995) "*Designing Human Consensus Antibodies With Minimal Positional Templates*," Cancer Res. 55 (23 Supp):5973s 5977s, Couto et al. (1995) "*Anti-BA46 Monoclonal Antibody Mc3: Humanization Using A Novel Positional Consensus And In Vivo And In Vitro Characterization*," Cancer Res. 55:1717 22, Sandhu (1994) "*A Rapid Procedure For The Humanization Of Monoclonal Antibodies*," Gene 150:409 410, Pedersen et al. (1994) "*Comparison Of Surface Accessible Residues In Human And Murine Immunoglobulin Fv Domains. Implication For Humanization Of Murine Antibodies*," J. Mol. Biol. 235:959 973, Jones et al. (1986) "*Replacing The Complementarity-Determining Regions In A Human Antibody With Those From A Mouse*," Nature 321: 522-525, Riechmann et al. (1988) "*Reshaping Human Antibodies For Therapy*," Nature 332:323-327, and Presta (1992) "*Antibody Engineering*," Curr. Op. Biotech. 3:394-398. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004-0049014 and 2003-0229208; U.S. Pat. Nos. 6,350,861; 6,180,370; 5,693, 762; 5,693,761; 5,585,089; and 5,530,101 and Riechmann et al. (1988) "*Reshaping Human Antibodies For Therapy*," Nature 332:323-327, all of which are incorporated herein by reference in their entireties.)

The present invention provides for the compositions and methods thereof, comprising a combination of a CD20 antibody and a Fc RIIB antibody. In certain embodiments, the Fc RIIB antibody is a humanized antibody molecule specific for Fc RIIB in which one or more regions of one or more CDRs of the heavy and/or light chain variable regions of a human antibody (the recipient antibody) have been substituted by analogous parts of one or more CDRs of a donor monoclonal antibody which specifically binds Fc RIIB, with a greater affinity than Fc RITA, e.g., a monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. In some embodiments, the CD20 antibody is a humanized antibody specific for CD20 in which one or more regions of one or more CDRs of the heavy and/or light chain of a human antibody (the recipient antibody) have been substituted by analogous pairs of one or more CDRs of a donor monoclonal antibody that specifically binds CD20, e.g., a monoclonal antibody such as rituximab or 2H7. In other embodiments, the humanized FcγRIIB antibodies bind to the same epitope as 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, and the humanized CD20 antibodies bind to the same epitope as rituximab or 2H7. In a most preferred embodiment, the humanized antibody specifically binds to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically the donor antibody is a non-human antibody, such as a rodent MAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses combinations comprising a humanized Fc RIIB antibody comprising at least one CDR grafted heavy chain and at least one CDR-grafted light chain and/or a humanized CD20 antibody.

In a preferred embodiment, the CDR regions of the humanized Fc RIIB specific antibody or humanized CD20 specific antibody are derived from a murine antibody specific for Fc RIIB or CD20, respectively. In some embodiments, the humanized antibodies described herein comprise alterations, including but not limited to amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein does not necessarily consist of the precise amino acid sequence of the framework region of a natural occurring human antibody variable region, but contains various alterations, including but not limited to amino acid deletions, insertions, modifications that alter the property of the humanized antibody, for example, improve the binding properties of a humanized antibody region that is specific for the same target as the murine Fc RIIB or CD20 specific antibody. In most preferred embodiments, a minimal number of alterations are made to the framework region in order to avoid large-scale introductions of non-human framework residues and to ensure minimal immunogenicity of the humanized antibody in humans. The donor monoclonal antibody is preferably a monoclonal antibody produced by clones 2B6, 3H7, 8B5.3.4, 1D5, 2E1, 2H9, 2D11, or 1F2 (having ATCC accession numbers PTA-4591, PTA-4592, PTA-7610, PTA-5958, PTA-5961, PTA-5962, PTA-5960, and PTA-5959, respectively) which bind Fc RIIB, or the monoclonal antibody is a CD20 antibody, such as rituximab or 2H7.

In a specific embodiment, the invention encompasses the use of combinations of a CD20 antibody and a CDR-grafted antibody which specifically binds Fc RIIB with a greater affinity than said antibody binds Fc RITA, wherein the CDR-grafted antibody comprises a heavy chain variable region domain comprising framework residues of the recipient antibody and residues from the donor monoclonal antibody, which specifically binds Fc RIIB with a greater affinity than said antibody binds Fc RIIA, e.g., monoclonal antibody produced from clones 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. In another specific embodiment, the invention encompasses the use of combinations of a CD20 antibody and a CDR-grafted antibody which specifically binds Fc RIIB with a greater affinity than said antibody binds Fc RITA, wherein the CDR-grafted antibody comprises a light chain variable region domain comprising framework residues of the recipient antibody and residues from the donor monoclonal antibody, which specifically binds Fc RIIB with a greater affinity than said antibody binds Fc RIIA, e.g., monoclonal antibody produced from clones 2B6, 3H7, 8B5.3.4, 1D5, 2E1, 2H9, 2D11, or 1F2.

Preferably the FcγRIIB humanized antibodies bind the extracellular domain of native human FcγRIIB. The humanized anti-FcγRIIB antibodies of the combinations can have a heavy chain variable region comprising the CDR1 amino acid sequence of: NYWIH (SEQ ID NO:1); or a heavy chain variable region comprising the CDR1 amino acid sequence of: DAWMD (SEQ ID NO:29); and/or a heavy chain variable region comprising CDR2 the amino acid sequence of: VIDPSDTYPN YNKKFK (SEQ ID NO:2); or a heavy chain variable region comprising CDR2 the amino acid sequence of: EIRNKANNLA TYYAESVKG (SEQ ID NO:30) and/or a heavy chain variable region comprising the CDR3 amino acid sequence of: NGDSDYYSGM DY (SEQ ID NO:3); or a heavy chain variable region comprising the CDR3 amino acid sequence of: YSPFAY (SEQ ID NO:31); and/or a light chain variable region comprising the CDR1 amino acid sequence of: RTSQSIGTNI H (SEQ ID NO:8); or a light chain variable region comprising the CDR1 amino acid sequence of: RASQEISGYL S (SEQ ID NO:38); and/or a light chain variable region comprising the CDR2 amino acid sequence of: NVSESIS (SEQ ID NO:9); a light chain variable region comprising the CDR2 amino acid sequence of: YVSESIS (SEQ ID NO:10); a light chain variable region comprising the CDR2 amino acid sequence of: YASESIS (SEQ ID NO:11); or a light chain variable region comprising the CDR2 amino acid sequence of: AASTLDS (SEQ ID NO:39) and/or a light chain variable region comprising the CDR3 amino acid sequence of: QQSNTWPFT (SEQ ID NO:12); or a light chain variable region comprising the CDR3 amino acid sequence of: LQYVSYPYT (SEQ ID NO:40).

In a specific embodiment, the invention encompasses the use of combinations of a CD20 antibody and a humanized antibody with the heavy chain variable domain having the amino acid sequence of SEQ ID NO:24, SEQ ID NO:37, SEQ ID NO:60, or SEQ ID NO:68 and a light chain variable domain having the amino acid sequence of SEQ ID NO:18, SEQ ID NO:20, SEQ ID NO:22; SEQ ID NO:46 or SEQ ID NO:62. In a specific embodiment, the combinations comprise a humanized antibody with the heavy chain variable domain having the amino acid sequence of SEQ ID NO:37 and the light chain variable domain having the amino acid sequence of SEQ ID NO:46. In yet another preferred embodiment, the humanized FcγRIIB antibodies further do not bind Fc activation receptors, e.g., FcγIIIA, FcγIIIB, etc.

In one specific embodiment, combinations comprising a CD20 antibody and a humanized 2B6 antibody are provided, wherein the VH region of the FcγRIIB antibody consists of the FR segments from the human germline VH segment VH1-18 (Matsuda et al. (1998) "The Complete Nucleotide Sequence Of The Human Immunoglobulin Heavy Chain Variable Region Locus," J. Exp. Med. 188:2151-2162) and JH6 (Ravetch et al. (1981) "Structure Of The Human Immunoglobulin Mu Locus: Characterization Of Embryonic And Rearranged J And D Genes," Cell 27(3 Pt. 2): 583-591), and one or more CDR regions of the 2B6 VH, having the amino acid sequence of SEQ ID NO:1, SEQ ID NO:2, or SEQ ID NO:3. In one embodiment, the 2B6 VH has the amino acid sequence of SEQ ID NO:24, SEQ ID NO:68, or SEQ ID NO:70. In another specific embodiment, the humanized 2B6 antibody further comprises a VL region, which consists of the FR segments of the human germline VL segment VK-A26 (Lautner-Rieske et al. (1992) "The Human Immunoglobulin Kappa Locus. Characterization Of The Duplicated A Regions," Eur. J. Immunol. 22:1023-1029) and JK4 (Hieter et al. (1982) "Evolution Of Human Immunoglobulin Kappa J Region Genes," J. Biol. Chem. 257:1516-1522), and one or more CDR regions of 2B6VL, having the amino acid sequence of SEQ ID NO:8, SEQ ID NO:9, SEQ ID NO:10, SEQ ID NO:11, and SEQ ID NO:12. In one embodiment, the 2B6 VL has the amino acid sequence of SEQ ID NO:18, SEQ ID NO:20, SEQ ID NO:22; SEQ ID NO:26, SEQ ID NO:62, or SEQ ID NO:66, and optionally in combination with one of the above-referenced 2B6 VH.

In some embodiments, the FcγRIIB antibody of the combination has a VH chain and/or VH domain comprising the amino acid sequence of SEQ ID NO:68. In some embodiments, the FcγRIIB antibody of the combination has a VL chain and/or VL domain comprising the amino acid sequence of SEQ ID NO:62. In some embodiments, the FcγRIIB antibody of the combination has a VH chain and/or VH domain comprising the amino acid sequence of SEQ ID NO:68 and a VL chain and/or VL domain comprising the amino acid sequence of SEQ ID NO:62. The FcγRIIB antibody can optionally further comprise a modified Fc domain having leucine at position 243, proline at position 292, leucine at position 300, isoleucine at position 305 and leucine at position 396.

In certain embodiments, the FcγRIIB antibody of the combination has a VH chain comprising the amino acid sequence of SEQ ID NO:70.
In some embodiments, the FcγRIIB antibody of the combination has a VL chain comprising the amino acid sequence of SEQ ID NO:66. In certain embodiments, the FcγRIIB antibody of the combination has a VH chain comprising the amino acid sequence of SEQ ID NO:70 and a VL chain comprising the amino acid sequence of SEQ ID NO:66. The FcγRIIB antibody can optionally further comprise a modified Fc domain having leucine at position 243, proline at position 292, leucine at position 300, isoleucine at position 305 and leucine at position 396.

In some embodiments, the FcγRIIB antibody of the combination has a VH domain and/or VH chain comprising the amino acid sequence of SEQ ID NO:71; see also FIG. 12. In some embodiments, the FcγRIIB antibody of the combination has a VL domain and/or VL chain comprising the amino acid sequence of SEQ ID NO:72; see also FIG. 11. In some embodiments, the FcγRIIB antibody of the combination has a VH domain and/or VH chain comprising the amino acid sequence of SEQ ID NO:71 and a VL domain and/or VL chain comprising the amino acid sequence of SEQ ID NO:72.

In another specific embodiment, combinations of a CD20 antibody and a humanized 3H7 antibody are provided, wherein the FcγRIIB VH region consists of the FR segments from a human germline VH segment and the CDR regions of the 3H7 VH, having the amino acid sequence of SED ID NO: 37. In another specific embodiment, the humanized 3H7 antibody further comprises a VL regions, which consists of the FR segments of a human germline VL segment and the CDR regions of 3H7VL, having the amino acid sequence of SEQ ID NO:46.

In particular, combinations of a CD20 antibody and a humanized antibody are provided wherein the FcγRIIB antibody immunospecifically binds to an extracellular domain of native human FcγRIIB, said FcγRIIB antibody comprising (or alternatively, consisting of) CDR sequences of 2B6, 3H7, or 8B5.3.4 in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2, a VH CDR3 and a VL CDR3; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR2, a VL CDR2 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR3, a VL CDR2 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

Humanized antibodies of the invention may be further characterized by epitope mapping, so that antibodies may be selected that have the greatest specificity for FcγRIIB and/or CD20. Epitope mapping methods of antibodies are well known in the art, and encompassed within the methods of the invention. In certain embodiments, FcγRIIB, or a fusion protein comprising one or more regions of FcγRIIB, may be used in mapping the epitope of an antibody of the invention. In a specific embodiment, the fusion protein contains the amino acid sequence of a region of an FcγRIIB fused to the Fc portion of human IgG2. Each fusion protein may further comprise amino acid substitutions and/or replacements of certain regions of the receptor with the corresponding region from a homolog receptor, such as FcγRIIA. Fusion proteins used to investigate the epitope of the anti-FcγRIIB antibodies comprise amino acid sequences of: KKFSRSDPN (SEQ ID NO:51); QKFSRLDPN (SEQ ID NO:52); QKFSRLDPT (SEQ ID NO:53); KKFSRLDPT (SEQ ID NO:54); QKFSHLDPT (SEQ ID NO:55); KKFSHLDPT (SEQ ID NO:56); APSSS (SEQ ID NO:57); and VPSMGSSS (SEQ ID NO:58). These molecules can help determine where the antibodies bind on the receptor.

The fusion proteins may be used in any biochemical assay for determination of binding to an anti-FcγRIIB antibody of the invention, e.g., an ELISA. In other embodiments, further confirmation of the epitope specificity may be done by using peptides with specific residues replaced with those from the FcγRIIA sequence.

B. Human Antibodies

Human CD20 and/or FcγRIIB antibodies to be used in the combinations of the invention can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "*Human Antibodies From Transgenic Mice,*" Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

C. Chimeric Antibodies

A chimeric antibody is a molecule in which different portions of the antibody are derived from different immunoglobulin molecules such as antibodies having a variable region derived from a non-human antibody and a human immunoglobulin constant region. In one embodiment, a combination of the invention comprises a chimeric FcγRIIB antibody and a CD20 antibody that is not a chimeric antibody. In other embodiments, a combination of the invention comprises a chimeric CD20 antibody and a FcγRIIB antibody that is not a chimeric antibody. In yet other embodiments, a combination of the invention comprises a chimeric FcγRIIB antibody and a chimeric CD20 antibody. In certain embodiments, neither the FcγRIIB antibody nor the CD20 antibody of the combination is a chimeric antibody.

The present invention provides the use of combinations of CD20 antibodies (chimeric or not chimeric) and chimeric antibodies of 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. Methods for producing chimeric antibodies are known in the art. See e.g., Morrison (1985) "*Transfectomas Provide Novel Chimeric Antibodies,*" Science 229:1202-1207; Oi et al. (1986) "*Chimeric Antibodies,*" BioTechniques 4:214-221; Gillies et al. (1989) "*High-Level Expression Of Chimeric Antibodies Using Adapted cDNA Variable Region Cassettes,*" J. Immunol. Methods 125:191-202; and U.S. Pat. Nos. 6,311,415, 5,807, 715, 4,816,567, and 4,816,397, which are incorporated herein by reference in their entirety. Chimeric CD20 antibodies or chimeric FcγRIIB antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan (1991) "*A Possible Procedure For Reducing The Immunogenicity Of Antibody Variable Domains While Preserving Their Ligand-Binding Properties,*" Molecular Immunology 28(4/5):489-498; Studnicka et al. (1994) "*Human-Engineered Monoclonal Antibodies Retain Full Specific Binding Activity By Preserving Non-CDR Complementarity-Modulating Residues,*" Protein Engineering 7:805-814; and Roguska et al. (1994) "*Humanization Of Murine Monoclonal Antibodies Through Variable Domain Resurfacing,*" Proc. Nat. Acad. Sci. 91:969-973), and chain shuffling (U.S. Pat. No. 5,565,332). Each of the above-identified references is incorporated herein by reference in its entirety.

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al. (1988) "*Reshaping Human Antibodies For Therapy,*" Nature 332:323-327, which are incorporated herein by reference in their entireties.)

D. Fc Region Modifications

The invention encompasses compositions, and methods thereof, comprising an antibody with a modified Fc region. In one embodiment, a combination of the invention comprises a FcγRIIB antibody that comprises a modified Fc region and a CD20 antibody that does not comprise a modified Fc region. In other embodiments, a combination of the invention comprises a CD20 antibody with a modified Fc region and a FcγRIIB antibody that does not comprise a modified Fc region. In yet other embodiments, a combination of the invention comprises a FcγRIIB antibody comprising a modified Fc region and a CD20 antibody comprising a modified Fc region. In certain embodiments, neither the FcγRIIB antibody nor the CD20 antibody of the combination comprises a modified Fc region.

The invention encompasses compositions (and methods thereof) comprising anti-Fc RIIIB and anti-CD20 antibodies, wherein the FcγRIIB antibody, the CD20 antibody, or both the FcγRIIB and CD20 antibody have Fc constant domains comprising one or more amino acid modifications which alter antibody effector functions such as those disclosed in U.S. Pat. No. 7,355,008; U.S. Patent Application Publication Nos. 2005-0064514; U.S. Pat. Nos. 5,624,821 and 5,648,260, European Patent No. EP 0 307 434 and U.S. application Ser. No. 11/502,820, filed Aug. 10, 2006, all of which are incorporated herein by reference in their entireties. These antibodies may exhibit improved ADCC activity (i.e., 2-fold, 10-fold, 100-fold, 500-fold, etc.) compared to comparable antibodies without amino acid modification. In certain embodiments, the Fc modifications of an antibody of the combination of the invention increases effector function, such as those Fc modifications described in U.S. patent application Ser. No. 11/271,140 by Stavenhagen (filed Nov. 10, 2005), which is herein incorporated by reference.

The present invention encompasses combinations of a CD20 antibody and a FcγRIIB antibody, wherein the CD20 antibody, the FcγRIIB antibody, or both the CD20 antibody and the FcγRIIB antibody comprises modifications, preferably in the Fc region, that modify the binding affinity of the Fc region of the antibody to one or more Fc R. Methods for modifying antibodies for modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821, each of which is incorporated herein by reference in their entirety. In some embodiments, the invention encompasses combinations of a CD20 antibody and a FcγRIIB antibody, wherein the CD20 antibody, the FcγRIIB antibody, or both the CD20 antibody and the FcγRIIB antibody have altered affinity for an activating FcγR, e.g., Fc RIIIA Preferably such modifications also have an altered Fc-mediated effector function. Modifications that affect Fc-mediated effector function are known in the art (See U.S. Pat. No. 6,194,551, which is incorporated herein by reference in its entirety). In other embodiments, the CD20 antibody of the combination with an FcγRIIB antibody (either with or without a modification in the Fc region) comprises modifications, preferably in the Fc region, that modify the binding affinity of the Fc region of the antibody to CD20.

In one particular embodiment, a combination of the invention comprises a CD20 antibody, a FcγRIIB antibody, or both a CD20 antibody and the FcγRIIB antibody that comprises a modified Fc region comprising one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof.

In some embodiments, the invention encompasses combinations of molecules wherein one or more of the FcγRIIB and/or CD20 antibodies in the combination comprises a variant Fc region having an amino acid modification at one or more of the following positions: 119, 125, 132, 133, 141, 142, 147, 149, 162, 166, 185, 192, 202, 205, 210, 214, 215, 216, 217, 218, 219, 221, 222, 223, 224, 225, 227, 229, 231, 232, 233, 235, 240, 241, 242, 243, 244, 246, 247, 248, 250, 251, 252, 253, 254, 255, 256, 258, 261, 262, 263, 268, 269, 270, 272, 274, 275, 276, 279, 280, 281, 282, 284, 287, 288, 289, 290, 291, 292, 293, 295, 298, 301, 303, 304, 305, 306, 307, 308, 309, 310, 311, 312, 313, 315, 316, 317, 318, 319, 320, 323, 326, 327, 328, 330, 333, 334, 335, 337, 339, 340, 343, 344, 345, 347, 348, 352, 353, 354, 355, 358, 359, 360, 361, 362, 365, 366, 367, 369, 370, 371, 372, 375, 377, 378, 379, 380, 381, 382, 383, 384, 385, 386, 387, 388, 389, 390, 392, 393, 394, 395, 396, 397, 398, 399, 400, 401, 402, 404, 406, 407, 408, 409, 410, 411, 412, 414, 415, 416, 417, 419, 420, 421, 422, 423, 424, 427, 428, 431, 433, 435, 436, 438, 440, 441, 442, 443, 446, or 447. Preferably, engineering of the Fc portion results in increased cell-mediated killing and/or complement mediated killing of the tumor cells.

For the antibodies in the combination that are specific for FcγRIIIB, Fc modifications may be made to reduce or abolish binding in the Fc domain to one or all FcγRs, particularly, to activating FcγRs such as Fc RIIIA and Fc RIIA.

The invention encompasses combinations of a CD20 antibody and a FcγRIIB antibody, wherein the CD20 antibody, the FcγRIIB antibody, or both the CD20 antibody and the FcγRIIB antibody comprises a variant Fc region consisting of or comprising any of the mutations listed in Table 2 below.

TABLE 2

| EXEMPLARY MUTATIONS | |
|---|---|
| Single Site Mutants | Double Site Mutants |
| K392R | Q347H, A339V |
| N315I | S415I, L251F |
| S132I | K290E, L142P |
| P396L | G285E, P247H |
| P396H | K409R, S166N |
| A162V | E334A, K334A |
| R292L | R292L, K334E |
| T359N | K288N, A330S |
| T366S | R255L, E318K |
| V379L | F243L, E318K |
| K288N | V279L, P395S |
| A330S | K246T, Y319F |
| F243L | F243I, V379L |
| E318K | K288M, K334E |
| V379M | K334E, E308D |
| S219Y | E233D, K334E |
| V282M | K246T, P396H |
| D401V | H268D, E318D |
| K222N | K246I, K334N |
| K334I | K320E, K326E |
| K334E | S375C, P396L |
| I377F | K288N, K326N |
| P247L | P247L, N421K |
| F372Y | S298N, W381R |
| K326E | R255Q, K326E |
| H224L | V284A, F372L |
| F275Y | T394M, V397M |
| L398V | P247L, E389G |
| K334N | K290T, G371D |
| S400P | P247L, L398Q |
| S407I | P247L, I377F |
| F372Y | K326E, G385E |
| T366N | S298N, S407R |
| K414N | E258D, N384K |
| M352L | F241L, E258G |
| T225S | K370N, S440N |
| I377N | K317N, F423deletion |
| K248M | P227S, K290E |
| R292G | K334E, E380D |
| S289N | P291S, P353Q |
| D270E | V240I, V281M |
| E233G | P232S, S304G |
| | P247L, L406F |
| | D399E, M428L |
| | L251F, F372L |
| | D399E, G402D |
| | K329T, P396L |
| | H268N, P396L |
| | K326I, P396L |
| | H268D, P396L |
| | K210M, P396L |
| | L358P, P396L |
| | K334N, P396L |
| | V379M, P396L |
| | P227S, P396L |
| | P217S, P396L |
| | Q419H, P396L |
| | K370E, P396L |
| | L242F, P396L |
| | R255L, P396L |
| | V240A, P396L |
| | T250A, P396L |
| | P247S, P396L |
| | L410H, P396L |
| | Q419L, P396L |
| | V427A, P396L |
| | E258D, P396L |
| | N384K, P396L |
| | V323I, P396L |
| | P244H, P396L |
| | V305L, P396L |
| | S400F, P396L |
| | V303I, P396L |
| | A330V, Q419H |
| | V263Q, E272D |
| | K326E, A330T |

In yet other embodiments, the invention encompasses combinations of a CD20 antibody and a FcγRIIB antibody, wherein the CD20 antibody, the FcγRIIB antibody, or both the CD20 antibody and the FcγRIIB antibody comprises a variant Fc region having more than two amino acid modifications. A non-limiting example of such variants is listed in Table 3 below. The invention encompasses mutations listed in Table 3 which further comprise one or more amino acid modifications such as those disclosed herein.

TABLE 3

EXEMPLARY COMBINATION VARIANTS

D399E, R292L, V185M
R301C, M252L, S192T
P291S, K288E, H268L, A141V
S383N, N384K, T256N, V262L, K218E, R214I, K205E, F149Y, K133M
S408I, V215I, V125L
G385E, P247H
V348M, K334N, F275I, Y202M, K147T
H310Y, T289A, Y407V, E258D
R292L, P396L, T359N
F275I, K334N, V348M
F243L, R255L, E318K
K334E, T359N, T366S
T256S, V305I, K334E, N390S
T335N, K370E, A378V, T394M, S424L
K334E, T359N, T366S, Q386R
K288N, A330S, P396L
P244H, L358M, V379M, N384K, V397M
P217S, A378V, S408R
P247L, I253N, K334N
D312E, K327N, I378S
D280E, S354F, A431D, L441I
K218R, G281D, G385R
P247L, A330T, S440G
T355N, P387S, H435Q
P247L, A431V, S442F
P343S, P353L, S375I, S383N
E216D, E345K, S375I
K288N, A330S, P396L
K222N, T335N, K370E, A378V, T394M
G316D, A378V, D399E
N315I, V379M, T394M
K326Q, K334E, T359N, T366S
A378V, N390I, V422I
V282E, V369I, L406F
V397M, T411A, S415N
T223I, T256S, L406F
L235V, V382M, S304G, V305I, V323I
P247L, W313R, E388G
D221Y, M252I, A330G, A339T, T359N, V422I, H433L
F243I, V379L, G420V
A231V, Q386H, V412M
T215P, K274N, A287G, K334N, L365V, P396L
P244A, K326I, C367R, S375I, K447T
R301H, K340E, D399E
C229Y, A287T, V379M, P396L, L443V
E269K, K290N, Q311R, H433Y
E216D, K334R, S375I
T335N, P387S, H435Q
K246I, Q362H, K370E
K334E, E380D, G446V
V303I, V369F, M428L
K246E, V284M, V308A
E293V, Q295E, A327T
Y319F, P352L, P396L
D221E, D270E, V308A, Q311H, P396L, G402D
K290T, N390I, P396L
K288R, T307A, K344E, P396L
V273I, K326E, L328I, P396L
K326I, S408N, P396L
K261N, K210M, P396L
F243L, V305I, A378D, F404S, P396L
K290E, V369A, T393A, P396L
K210N, K222I, K320M, P396L
P217S, V305I, I309N, N390H, P396L
K246N, Q419R, P396L
P217A, T359A, P396L
V215I, K290V, P396L
F275L, Q362H, N384K, P396L
A330V, H433Q, V427M

TABLE 3-continued

EXEMPLARY COMBINATION VARIANTS

V263Q, E272D, Q419H
N276Y, T393N, W417R
V282L, A330V, H433Y, T436R
V284M, S298N, K334E, R355W
A330V, G427M, K438R
S219T, T225K, D270E, K360R
K222E, V263Q, S298N
E233G, P247S, L306P
S219T, T225K, D270E
S254T, A330V, N361D, P243L
V284M, S298N, K334E, R355W, R416T
D270E, G316D, R416G
K392T, P396L, D270E
R255L, P396L, D270E
V240A, P396L, D270E
Q419H, P396L, D270E
K370E, P396L, D270E
P247L, N421K, D270E
R292P, V305I
R292P, V305I, F243L
V284M, R292L, K370N
F243L, R292P, Y300L, V305I, P396L
F243L, R292P, Y300L, P396L
F243L, R292P, Y300L

In most preferred embodiments, wherein the CD20 antibody, the FcγRIIB antibody, or both the CD20 antibody and the FcγRIIB antibody of the combination (e.g., the 2B6, 3H7, or 8B5.3.4 antibody, or any other CD20 antibody or FcγRIIB antibody described herein) has a modified Fc region with altered affinity for activating and/or inhibitory receptors, wherein the Fc domain has one or more amino acid modifications, wherein said one or more amino acid modifications is a substitution at position 288 with asparagine, at position 330 with serine and at position 396 with leucine (MgFc10); or a substitution at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 392 with threonine, and at position 396 with leucine (MgFc38); or a substitution at position 221 with glutamic acid, at position 270 with glutamic acid, at position 308 with alanine, at position 311 with histidine, at position 396 with leucine, and at position 402 with aspartic acid (MgFc42); or a substitution at position 240 with alanine, and at position 396 with leucine (MgFc52); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with leucine, and at position 396 with leucine (MgFc55); or a substitution at position 370 with glutamic acid and at position 396 with leucine (MgFc59); or a substitution at position 243 with leucine, at position 292 with proline, at position 300 with leucine, at position 305 with isoleucine, and at position 396 with leucine (MgFc88); or a substitution at position 243 with leucine, at position 292 with proline, at position 300 with leucine, and at position 396 with leucine (MgFc88A); or a substitution at position 243 with leucine, at position 292 with proline, and at position 300 with leucine (MgFc155) (See, also, Tables 5 & 6 of U.S. Pat. No. 7,355,008, which is herein incorporated by reference).

In a preferred embodiment, the CD20 antibody, the FcγRIIB antibody, or both the CD20 antibody and the FcγRIIB antibody of the combination (e.g., the 2B6, 3H7, or 8B5.3.4 antibody, or any other CD20 antibody or FcγRIIB antibody described herein) has a modified Fc region with a leucine at position 243, a proline at position 292, a leucine at position 300, an isoleucine at position 305 and a leucine at position 396.

In specific embodiments, the variant Fc region of the CD20 antibody, the FcγRIIB antibody, or both the CD20 antibody and the FcγRIIB antibody of the combination (e.g., the 2B6, 3H7, or 8B5.3.4 antibody, or any other CD20 antibody or FcγRIIB antibody described herein) has a leucine at position 247, a lysine at position 421 and a glutamic acid at position 270 (MgFc31/60); a threonine at position 392, a leucine at position 396, and a glutamic acid at position 270 (MgFc38/60); a threonine at position 392, a leucine at position 396, a glutamic acid at position 270, and a leucine at position 243 (MgFc38/60/F243L); a histidine at position 419, a leucine at position 396, and a glutamic acid at position 270 (MGFc51/60); a histidine at position 419, a leucine at position 396, a glutamic acid at position 270, and a leucine at position 243 (MGFc51/60/F243L); a lysine at position 255 and a leucine at position 396 (MgFc55); a lysine at position 255, a leucine at position 396, and a glutamic acid at position 270 (MGFc55/60); a lysine at position 255, a leucine at position 396, a glutamic acid at position 270, and a lysine at position 300 (MGFc55/60/Y300L); a lysine at position 255, a leucine at position 396, a glutamic acid at position 270, and a leucine at position 243 (MgFc55/60/F243L); a glutamic acid at position 370, a leucine at position 396, and a glutamic acid at position 270 (MGFc59/60); a glutamic acid at position 270, an aspartic acid at position 316, and a glycine at position 416 (MgFc71); a leucine at position 243, a proline at position 292, an isoleucine at position 305, and a leucine at position 396 (MGFc74/P396L); a glutamine at position 297, or any combination of the individual substitutions.

E. Carbohydrate Modifications

The invention also provides methods and compositions using or having CD20 and/or FcγRIIB antibodies with altered oligosaccharide content. Oligosaccharides as used herein refer to carbohydrates containing two or more simple sugars and the two terms may be used interchangeably herein. Carbohydrate moieties of the antibody combinations of the instant invention will be described with reference to commonly used nomenclature in the art. For a review of carbohydrate chemistry, see, e.g., Hubbard et al. (1981) "*Synthesis And Processing Of Asparagine-Linked Oligosaccharides,*" Ann. Rev. Biochem., 50: 555-583, which is incorporated herein by reference in its entirety. This nomenclature includes for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

In general, antibodies contain carbohydrate moeities at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al. (1998) "*IgG-Fc-Mediated Effector Functions: Molecular Definition Of Interaction Sites For Effector Ligands And The Role Of Glycosylation,*" Immunol. Rev. 163: 59-76; Wright et al. (1997) "*Effect Of Glycosylation On Antibody Function: Implications For Genetic Engineering,*" Trends Biotech. 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al. (2001) "*Sialylation Of Human IgG-Fc Carbohydrate By Transfected Rat Alpha2,6-Sialyltransferas,*" Biochem. Biophys. Res. Commun. 288: 243-249; Groenink et al. (1996) "*On The Interaction Between Agalactosyl IgG And Fc Gamma Receptors,*" Eur. J. Immunol. 26: 1404-1407; Boyd et al. (1995) "*The Effect Of The Removal Of Sialic Acid, Galactose And Total Carbohydrate On The Functional Activity Of Campath-1H,*" Mol. Immunol. 32: 1311-1318; Kumpel et al. (1994) "*Galactosylation Of Human IgG Monoclonal Anti-D Produced By EBV-Transformed B-Lymphoblastoid Cell Lines Is Dependent On Culture Method And Affects Fc Receptor-Mediated Functional Activity,*" Human Antibody Hybridomas, 5: 143-151. The invention encompasses combinations of a CD20 antibody and a FcγRIIB antibody, wherein the FcγRIIB antibody comprises a variation in the carbohydrate moiety that is attached to Asn 297. In one embodiment, the carbohydrate moiety has a galactose and/or galactose-sialic acid at one or both of the terminal GlcNAc and/or a third GlcNac arm (bisecting GlcNAc).

In some embodiments, the CD20 antibodies and/or the FcγRIIB antibodies of the combinations are substantially free of one or more selected sugar groups, e.g., one or more sialic acid residues, one or more galactose residues, one or more fucose residues. An antibody that is substantially free of one or more selected sugar groups may be prepared using common methods known to one skilled in the art, including for example recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such antibodies include for example, culturing cells under conditions which prevent or reduce the addition of one or more selected sugar groups, or post-translational removal of one or more selected sugar groups.

In some embodiments, the FcγRIIB antibodies of the combinations of the invention lack a fructose on its carbohydrate moiety, e.g., the carbohydrate attachment on Asn 297. The antibody may be prepared for example by (A) use of an engineered host cell that is deficient in fucose metabolism such that it has a reduced ability to fucosylate proteins expressed therein; (B) culturing cells under conditions which prevent or reduce fusocylation; (C) post-translational removal of fucose, e.g., with a fucosidase enzyme; or (D) purification of the antibody so as to select for the product which is not fucosylated. Most preferably, nucleic acid encoding the desired antibody is expressed in a host cell that has a reduced ability to fucosylate the antibody expressed therein. Preferably the host cell is a dihydrofolate reductase deficient chinese hamster ovary cell (CHO), e.g., a Lec 13 CHO cell (lectin resistant CHO mutant cell line; Ripka et al. (1986) "*Lectin-Resistant CHO Cells: Selection Of Four New Pea Lectin-Resistant Phenotypes,*" Somatic Cell & Molec. Gen. 12(1): 51-62; Ripka et al. (1986) "*Two Chinese Hamster Ovary Glycosylation Mutants Affected In The Conversion Of GDP-Mannose To GDP-Fucose,*" Arch. Biochem. Biophys. 249(2): 533-545), CHO-K1, DUX-B11, CHO-DP12 or CHO-DG44, which has been modified so that the antibody is not substantially fucosylated. Thus, the cell may display altered expression and/or activity for the fucoysltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al. (2002) "*Lack Of Fucose On Human IgG1 N-Linked Oligosaccharide Improves Binding To Human Fcgamma RIII And Antibody-Dependent Cellular Toxicity,*" J. Biol. Chem. 277(30): 26733-26740; both of which are incorporated herein by reference in their entirety.

In some embodiments, the altered carbohydrate modifications of the CD20 antibody or FcγRIIB antibody modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for e.g., see Shields et al. (2002) "*Lack Of Fucose On Human IgG1 N-Linked Oligosaccharide Improves Binding To Human Fcgamma RIII And Antibody-Dependent Cellular Toxicity,*" J. Biol. Chem. 277(30): 26733-26740; Davies et al. (2001) "*Expression Of GnTIII In A Recombinant Anti-CD20 CHO Production Cell Line: Expression Of Antibodies With Altered Glycoforms Leads To An Increase In ADCC Through Higher Affinity For FCγRIII,*" Biotechnology & Bioengineering, 74(4): 288-294). In another specific embodiment, the altered carbohydrate modifications enhance the binding of FcγRIIB antibodies of the combinations of the invention to Fc RIIB receptor. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al. (1988) "*Glycosylation Of A VH Residue Of A Monoclonal Antibody Against Alpha (1 - - - 6) Dextran Increases Its Affinity For Antigen,*" Journal of Exp. Med. 168(3): 1099-1109; Tao et al. (1989) "*Studies Of Aglycosylated Chimeric Mouse-Human IgG. Role Of Carbohydrate In The Structure And Effector Functions Mediated By The Human IgG Constant Region,*" J. Immunol., 143(8): 2595-2601; Routledge et al. (1995) "*The Effect Of Aglycosylation On The Immunogenicity Of A Humanized Therapeutic CD3 Monoclonal Antibody,*" Transplantation, 60(8): 847-853; Elliott et al. (2003) "*Enhancement Of Therapeutic Protein In Vivo Activities Through Glycoengineering,*" Nature Biotechnology, 21: 414-421; Shields et al. (2002) "*Lack Of Fucose On Human IgG1 N-Linked Oligosaccharide Improves Binding To Human Fcgamma RIII And Antibody-Dependent Cellular Toxicity,*" J. Biol. Chem. 277(30): 26733-26740; all of which are incorporated herein by reference in their entirety.

In some embodiments, the combinations of the invention encompass CD20 and/or FcγRIIB antibodies comprising one or more glycosylation sites, so that one or more carbohydrate moieties are covalently attached to the antibody. In other embodiments, the invention encompasses combinations of CD20 and FcγRIIB antibodies, wherein either or both comprise one or more glycosylation sites and one or more modifications in the Fc region, such as those disclosed supra and those known to one skilled in the art. In preferred embodiments, the one or more modifications in the Fc region of the FcγRIIB antibody of the combination enhance the affinity of the antibody for an activating Fc R, e.g., Fc RIIIA, relative to the antibody comprising the wild type Fc regions. Antibodies of the combinations of the invention with one or more glycosylation sites and/or one or more modifications in the Fc region have an enhanced antibody mediated effector function, e.g., enhanced ADCC activity. In some embodiments, the combinations comprise antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

The invention encompasses combinations of CD20 and/or FcγRIIB antibodies that have been modified by introducing one or more glycosylation sites into one or more sites of the antibodies, preferably without altering the functionality of the antibody, e.g., binding activity to CD20 or Fc RIIB, respectively. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the combinations of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody using methods well known in the art to which this invention pertains. See, for example, "*In Vitro Mutagenesis,*" RECOMBINANT DNA: A SHORT COURSE, J. D. Watson, et al. W.H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

In some embodiments, modification of the carbohydrate content of an antibody of the invention can be accomplished, e.g., by adding or deleting a glycosylation site. Methods for modifying the carbohydrate content of antibodies are well known in the art, see, e.g., U.S. Pat. Nos. 6,218,149 and 6,946,292; EP 0 359 096 B1; U.S. Publication No. US 2002-0028486; WO 03/035835; U.S. Pat. Nos. 6,218,149; 6,472,511; all of which are incorporated herein by reference in their entirety. In other embodiments, modification of the carbohydrate content of an antibody can be accomplished by deleting one or more endogenous carbohydrate moieties of the antibody.

In some specific embodiments, the invention encompasses the use of combinations of a CD20 antibody and a modified Fc RIIB antibody, wherein the N-glycosylation consensenus site $Asn_{50}$-Val-Ser of the CDR2 region has been modified, so that the glycosylation site at position 50 is eliminated. Although not intending to be bound by a particular mechanism of action, removal of the glycosylation site may limit potential variation in production of the antibody as well as potential immunogenicity in a pharmaceutical application. In a specific embodiment, the combinations of the invention comprise a humanized Fc RIIB antibody wherein the amino acid at position 50 has been modified, e.g., deleted or substituted. In another specific embodiment, an FcγRIIB antibody in the combination comprises an amino acid modification, e.g., deletion or substitution, at position 51. In one specific embodiment, the antibody combination of the invention comprises a humanized Fc RIIB antibody, wherein the amino acid at position 50 has been replaced with tyrosine. In another more specific embodiment, the combinations of the invention comprise a Fc RIIB antibody, wherein the amino acid at position 50 has been replaced with tyrosine and the amino acid at position 51 has been replaced with alanine.

F. FcγRIIB Agonists And Antagonists

In addition to the combined use of a CD20 antibody and a FcγRIIB-specific antibody, an analog, derivative, or an antigen-binding fragment thereof, other FcγRIIB agonist and antagonists may be used in accordance with the compositions and methods of the invention. FcγRIIB agonists and antagonists include, but are not limited to, proteinaceous molecules (e.g., proteins, polypeptides, soluble FcγRIIB polypeptides), peptides, fusion proteins (e.g., soluble FcγRIIB polypeptides conjugated to a therapeutic moiety), nucleic acid molecules (e.g., FcγRIIB antisense nucleic acid molecules, triple helices, dsRNA that mediates RNAi, or nucleic acid molecules encoding proteinaceous molecules), organic molecules, inorganic molecules, small organic molecules, drugs, and small inorganic molecules that block, inhibit, reduce or neutralize a function, an activity and/or the expression of a FcγRIIB polypeptide, expressed by an immune cell, preferably a B cell. In some embodiments, a FcγRIIB agonist or antagonist used in accordance with the combination compositions and methods of the invention is not a small organic molecule, a drug or an antisense molecule. FcγRIIB agonists and antagonists can be identified using techniques well-known in the art or described herein.

Prophylactic and therapeutic compounds that can be used in the combinations of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

In a preferred embodiment, proteins, polypeptides or peptides (including antibodies and fusion proteins) that are utilized as FcγRIIB antagonists are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as FcγRIIB antagonists are human or humanized.

G. Antibody Conjugates

The present invention encompasses combinations of a CD20 antibody and a FcγRIIB antibody, wherein either or both antibodies are recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Antibodies may be used for example to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT Publication No. WO 93/21232; EP 439,095; Naramura et al. (1994) "*Mechanisms Of Cellular Cytotoxicity Mediated By A Recombinant Antibody-IL2 Fusion Protein Against Human Melanoma Cells,*" Immunol. Lett., 39:91-99; U.S. Pat. No. 5,474,981; Gillies et al. (1992) "*Antibody-Targeted Interleukin* 2 *Stimulates T-Cell Killing Of Autologous Tumor Cells,*" Proc. Nat. Acad. Sci., 89:1428-1432; and Fell et al. (1991) "*Genetic Construction And Characterization Of A Fusion Protein Consisting Of A Chimeric F(ab') With Specificity For Carcinomas And Human IL-2,*" J. Immunol., 146:2446-2452, each of which is incorporated herein by reference in their entireties.

Further, the CD20 antibody, the FcγRIIB antibody or both the CD20 and FcγRIIB can be conjugated to a therapeutic agent or drug moiety that modifies a given biological response. The therapeutic agent or drug moiety conjugated to a CD20 antibody and a FcγRIIB antibody in a combination of the invention may or may not be the same. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, e.g., PCT Publication No. WO 97/34911), Fas Ligand (Takahashi et al. (1994) "*Human Fas Ligand: Gene Structure, Chromosomal Location And Species Specificity,*" Int. Immunol., 6:1567-1574), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH"); a protease, or a ribonuclease.

The CD20 antibody, the FcγRIIB antibody or both the CD20 and FcγRIIB antibodies can be fused to marker sequences, such as a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al. (1989) "*Bioassay For Trans-Activation Using Purified Human Immu-* nodeficiency Virus Tat-Encoded Protein: Trans-Activation Requires mRNA Synthesis," Proc. Natl. Acad. Sci. USA, 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al. (1984) *"The Structure Of An Antigenic Determinant In A Protein,"* Cell, 37:767-778) and the "flag" tag (Knappik et al. (1994) *"An Improved Affinity Tag Based On The FLAG Peptide For The Detection And Purification Of Recombinant Antibody Fragments,"* Biotechniques, 17(4):754-761).

The present invention further includes the use of compositions comprising heterologous polypeptides fused or conjugated to a CD20 or FcγRIIB antibody fragment. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al. (1991) *"Protection Against Endotoxic Shock By A Tumor Necrosis Factor Receptor Immunoadhesin,"* Proc. Nat. Acad. Sci. 88: 10535-10539; Zheng et al. (1995) *"Administration Of Non-cytolytic IL-10/Fc In Murine Models Of Lipopolysaccharide-Induced Septic Shock And Allogeneic Islet Transplantation,"* J. Immunol. 154:5590-5600; and Vie et al. (1992) *"Human Fusion Proteins Between Interleukin 2 nd IgM Heavy Chain Are Cytotoxic For Cells Expressing The Interleukin 2 Receptor,"* Proc. Nat. Acad. Sci. 89:11337-11341, all of which are incorporated by reference in their entireties.

Additional CD20 antibody or FcγRIIB antibody fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al. (1997) *"Applications Of DNA Shuffling To Pharmaceuticals And Vaccines,"* Curr. Opinion Biotechnol. 8:724-733; Harayama (1998) *"Artificial Evolution By DNA Shuffling,"* Trends Biotechnol. 16:76-82; Hansson, et al. (1999) *"Evolution Of Differential Substrate Specificities In Mu Class Glutathione Transferases Probed By DNA Shuffling,"* J. Mol. Biol. 287:265-276; and Lorenzo et al. (1998) *"PCR-Based Method For The Introduction Of Mutations In Genes Cloned And Expressed In Vaccinia Virus,"* BioTechniques 24:308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to FcγRIIB or CD20 may be recombined with one or more components, motifs, sections, parts, domains, fragments, etc., of one or more heterologous molecules.

The present invention also encompasses combinations, wherein a CD20 antibody, a FcγRIIB antibody, or both a CD20 and a FcγRIIB antibody is conjugated to a diagnostic or therapeutic agent or any other molecule for which serum half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), (phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

An antibody of the combinations of the invention can be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Moreover, an antibody of the combinations of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al. (1998) "*Comparison Of 1,4,7,10-Tetraazacyclododecane-N, N',N",N"'-Tetraacetic Acid (DOTA)-Peptide-ChL6, A Novel Immunoconjugate With Catabolizable Linker, To 2-Iminothiolane-2-[p-(bromoacetamido)benzyl]-DOTA-ChL6 In Breast Cancer Xenografts*," Clin. Cancer Res. 4:2483-2490; Peterson et al. (1999) "*Enzymatic Cleavage Of Peptide-Linked Radiolabels From Immunoconjugates*," Bioconjug. Chem. 10:553-557; and Zimmerman et al. (1999) "*A Triglycine Linker Improves Tumor Uptake And Biodistributions Of 67-Cu-Labeled Anti-Neuroblastoma MAb chCE7 F(ab')2 Fragments*," Nucl. Med. Biol. 26:943-950 each incorporated by reference in their entireties.

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-256, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-653, Marcel Dekker, Inc.; Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates*," Immunol. Rev., 62:119-158.

CD20 antibody and FcγRIIB antibody combinations of the invention that comprise an antibody or fragment thereof, with or without a therapeutic moiety conjugated to it, administered alone or in further combination with cytotoxic factor(s) and/or cytokine(s) can be used as a therapeutic.

Alternatively, an antibody of the combination can be conjugated to a second antibody to form an antibody heteroconjugate as described by Segal in U.S. Pat. No. 4,676,980, which is incorporated herein by reference in its entirety.

Antibodies of the combinations may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

H. Preparation and Characterization of Monoclonal Antibodies of the Invention

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest such as CD20 or FcγRIIB or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Monoclonal antibodies that specifically bind FcγRIIB with greater affinity than said monoclonal antibodies bind FcγRIIA can be produced by a method comprising: immunizing one or more FcγRIIA transgenic mice (see U.S. Pat. Nos. 5,877,396 and 5,824,487) with the purified extracellular domain of human FcγRIIB, amino acids 1-180; producing hybridoma cell lines from spleen cells of said mice, screening said hybridoma cells lines for one or more hybridoma cell lines that produce antibodies that specifically bind FcγRIIB with greater affinity than said antibodies bind FcγRIIA. FcγRIIB monoclonal antibodies that specifically bind FcγRIIB, particularly human FcγRIIB, with a greater affinity than said monoclonal antibodies bind FcγRIIA, can be produced by a method further comprising: immunizing one or more FcγRIIA transgenic mice with purified FcγRIIB or an immunogenic fragment thereof, booster immunizing said mice sufficient number of times to elicit an immune response, producing hybridoma cells lines from spleen cells of said one or more mice, screening said hybridoma cell lines for one or more hybridoma cell lines that produce antibodies that specifically bind FcγRIIB with a greater affinity than said antibodies bind FcγRIIA. In some methods, the mice are immunized with purified FcγRIIB which has been mixed with any adjuvant known in the art to enhance immune response. Adjuvants that can be used for producing monoclonal antibodies include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used for producing monoclonal antibodies include, Cholera toxin, paropox proteins, MPL® (Corixa Corporation; See also Lodmell et al. (2000) "*DNA Vaccination Of Mice Against Rabies Virus: Effects Of The Route Of Vaccination And The Adjuvant Monophosphoryl Lipid A (MPL)*," Vaccine, 18: 1059-1066; Ulrich et al. (2000) "*MPL® Immunostimulant: Adjuvant Formulations*," Methods in Molecular Medicine, 273-282; Johnson et al. (1999) "*3-O-Desacyl Monophosphoryl Lipid A Derivatives: Synthesis And Immunostimulant Activities*," Journal of Medicinal Chemistry, 42: 4640-4649; Baldridge et al. (1999) "*Monophosphoryl Lipid A (MPL) Formulations For The*

Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "*Active Immunotherapy With Ultraviolet B-Irradiated Autologous Whole Melanoma Cells Plus DETOX In Patients With Metastatic Melanoma*," Clin. Cancer Res. 4(3):619-627; and Gupta et al. (1995) "*Adjuvants For Human Vaccines—Current Status, Problems And Future Prospects*," Vaccine, 13(14):1263-1276 both of which are incorporated herein by reference.

Antibody fragments which recognize specific epitopes can be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and at least a portion of the hinge region of the heavy chain.

For example, antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al. (1995) "*Phage Display Of Disulfide-Stabilized Fv Fragments*," J. Immunol. Methods, 182:41-50; Ames et al. (1995) "*Conversion Of Murine Fabs Isolated From A Combinatorial Phage Display Library To Full Length Immunoglobulins*," J. Immunol. Methods, 184: 177-186; Kettleborough et al. (1994) "*Isolation Of Tumor Cell-Specific Single-Chain Fv From Immunized Mice Using Phage-Antibody Libraries And The Re-Construction Of Whole Antibodies From These Antibody Fragments*," Eur. J. Immunol., 24:952-958; Persic et al. (1997) "*An Integrated Vector System For The Eukaryotic Expression Of Antibodies Or Their Fragments After Selection From Phage Display Libraries*," Gene, 187:9-18; Burton et al. (1994) "*Human Antibodies From Combinatorial Libraries*," Advances in Immunology, 57:191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax et al. (1992) "*Expression Of A Heterodimeric Fab Antibody Protein In One Cloning Step*," BioTechniques, 12(6):864-869; and Sawai et al. (1995) "*Direct Production Of The Fab Fragment Derived From The Sperm Immobilizing Antibody Using Polymerase Chain Reaction And cDNA Expression Vectors*," Am. J. Repr. Immunol. 34:26-34; and Better et al. (1988) "*Escherichia coli Secretion Of An Active Chimeric Antibody Fragment*," Science, 240:1041-1043 (each of which is incorporated by reference in its entirety). Examples of techniques which can be used to produce single-chain Fvs and antibodies include those described in U.S. Pat. Nos. 4,946,778 and 5,258,498; Huston et al. (1991) "*Protein Engineering Of Single-Chain Fv Analogs And Fusion Proteins*," Methods in Enzymology, 203:46-88; Shu et al. (1993) "*Secretion Of A Single-Gene-Encoded Immunoglobulin From Myeloma Cells*," Proc. Nat. Acad. Sci., 90:7995-7999; and Skerra et al. (1988) "*Assembly Of A Functional Immunoglobulin Fv Fragment In Escherichia coli*," Science, 240:1038-1040.

Phage display technology can be used to increase the affinity of an antibody used in a combination of the invention for FcγRIIB or CD20. This technique would be useful in obtaining high affinity antibodies that could be used in the combinatorial methods of the invention. The technology, referred to as affinity maturation, employs mutagenesis or CDR walking and re-selection using FcγRIIB or CD20 or an antigenic fragment thereof to identify antibodies that bind with higher affinity to the antigen when compared with the initial or parental antibody (See, e.g., Glaser et al. (1992) "*Antibody Engineering By Codon-Based Mutagenesis In A Filamentous Phage Vector System*," J. Immunology 149: 3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al. (1998) "*Stepwise in vitro Affinity Maturation Of Vitaxin, An Alphav Beta3-Specific Humanized mAb*," Proc Natl. Acad. Sci. USA 95:6037-6042; Yelton et al. (1995) "*Affinity Maturation Of The Br96 Anti-Carcinoma Antibody By Codon-Based Mutagenesis*," J. Immunology 155:1994-2004). CDR walking which randomizes the light chain is also possible (See Schier et al. (1996) "*Isolation Of Picomolar Affinity Anti-C-ErbB-2 Single-Chain Fv By Molecular Evolution Of The Complementarity Determining Regions In The Center Of The Antibody Binding Site*," J. Mol. Bio. 263:551-567).

The antibodies used in the combinations of the invention may be characterized for specific binding to Fc RIIB or CD20 using any immunological or biochemical based method known in the art for characterizing, including quantitating, the interaction of the antibody to Fc RIIB or CD20. Specific binding of an antibody of a combination of the invention to Fc RIIB or CD20 may be determined for example using immunological or biochemical based methods including, but not limited to, an ELISA assay, surface plasmon resonance assays, immunoprecipitation assay, affinity chromatography, and equilibrium dialysis Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, CURRENT PROTOCOLS IN MOLECULAR BIOLOGY, Vol. 1, John Wiley & Sons, Inc., New York, which is incorporated by reference herein in its entirety).

Antibodies of the combinations of the invention can be assayed using any surface plasmon resonance based assays known in the art for characterizing the kinetic parameters of the interaction of the antibody with Fc RIIB or CD20. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullett et al. (2000) "*Surface Plasmon Resonance-Based Immunoassays*," Methods 22: 77-91; Dong et al. (2002) "*Some New Aspects In Biosensors*," Reviews in Mol. Biotech., 82: 303-323; Fivash et al. (1998) "*BIAcore For Macromolecular Interaction*," Current Opinions in Biotechnology 9: 97-101; Rich et al. (2000) "*Advances In Surface Plasmon Resonance Biosensor Analysis*," Current Opinions in Biotechnology 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occur is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

The invention encompasses characterization of the antibodies using certain characterization assays for identifying the function of the antibodies of the invention, such as the activity to modulate FcγRIIB signaling. For example, characterization assays can measure phosphorylation of tyrosine residues in the ITIM motif of FcγRIIB, or measure the inhibition of B cell receptor-generated calcium mobilization. The characterization assays can be cell-based or cell-free assays.

It has been well established in the art that, in mast cells, coaggregation of FcγRIIB with the high affinity IgE receptor, FcεRI, leads to inhibition of antigen-induced degranulation, calcium mobilization, and cytokine production (Metcalfe et al. (1997) "Mast Cells," Physiol. Rev. 77:1033-1079; Long (1999) "*Regulation Of Immune Responses Through Inhibitory Receptors*," Annu. Rev. Immunol. 17: 875-904). The molecular details of this signaling pathway have been recently elucidated (Ott (2002) "*Downstream Of Kinase, p62(dok), Is A Mediator Of Fc gamma IIB Inhibition Of Fc Epsilon RI Signaling*," J. Immunol. 162(9):4430-4439). Once coaggregated with FcεRI, FcγRIIB is rapidly phosphorylated on tyrosine in its ITIM motif, and then recruits Src Homology-2 containing inositol-5-phosphatase (SHIP), an SH2 domain-containing inositol polyphosphate 5-phosphatase, which is in turn phosphorylated and associates with Shc and p62$^{dok}$ (p62$^{dok}$ is the prototype of a family of adaptor molecules, which includes signaling domains such as an aminoterminal pleckstrin homology domain (PH domain), a PTB domain, and a carboxy terminal region containing PXXP motifs and numerous phosphorylation sites (Carpino et al. (1997) "*p62(dok): A Constitutively Tyrosine-Phosphorylated, GAP-Associated Protein In Chronic Myelogenous Leukemia Progenitor Cells*," Cell, 88: 197-204; Yamanashi et al. (1997) "*Identification Of The Abl-And rasGAP-Associated 62 kDa Protein As A Docking Protein, Dok*," Cell, 88:205-211).

Anti-FcγRIIB antibodies of the combinations of the invention can be characterized for the ability to modulate one or more IgE mediated responses. Cells lines co-expressing the high affinity receptor for IgE and the low affinity receptor for Fc RIIB can be used in characterizing the anti-FcγRIIB antibodies of the combinations of the invention in modulating IgE mediated responses. In a specific embodiment, cells from a rat basophilic leukemia cell line (RBL-H23; Barsumian et al. (1981) "*IgE-Induced Histamine Release From Rat Basophilic Leukemia Cell Lines: Isolation Of Releasing And Nonreleasing Clones*," Eur. J. Immunol. 11:317-323, which is incorporated herein by reference in its entirety) transfected with full length human Fc RIIB can be used in the methods of the invention. RBL-2H3 is a well characterized rat cell line that has been used extensively to study the signaling mechanisms following IgE-mediated cell activation. When expressed in RBL-2H3 cells and coaggregated with FIER1, FcγRIIB inhibits FcεRI-induced calcium mobilization, degranulation, and cytokine production (Malbec et al. (1998) "*Fc Epsilon Receptor I-Associated Lyn-Dependent Phosphorylation Of Fc Gamma Receptor IIB During Negative Regulation Of Mast Cell Activation*," J. Immunol. 160:1647-1658; Daeron et al. (1995) "*Regulation Of High-Affinity IgE Receptor-Mediated Mast Cell Activation By Murine Low-Affinity IgG Receptors*," J. Clin. Invest. 95:577-585; Ott (2002) "*Downstream Of Kinase, p62(dok), Is A Mediator Of Fc gamma IIB Inhibition Of Fc Epsilon RI Signaling*," J. Immunol. 162(9): 4430-4439).

In some embodiments, the anti-FcγRIIB antibodies of the combinations of the invention can be characterized for inhibition of FcER1 induced mast cell activation. For example, cells from a rat basophilic leukemia cell line (RBL-H23; Barsumian et al. (1981) "*IgE-Induced Histamine Release From Rat Basophilic Leukemia Cell Lines: Isolation Of Releasing And Nonreleasing Clones*," Eur. J. Immunol. 11:317-323) that have been transfected with FcγRIIB can be sensitized with IgE and stimulated either with F(ab')$_2$ fragments of rabbit anti-mouse IgG, to aggregate FcεRI alone, or with whole rabbit anti-mouse IgG to coaggregate FcγRIIB and FcεRI. In this system, indirect modulation of downstream signaling molecules can be assayed upon addition of an FcγRIIB antibody of the invention to the sensitized and stimulated cells. For example, tyrosine phosphorylation of FcγRIIB and recruitment and phosphorylation of SHIP, activation of MAP kinase family members, including but not limited to Erk1, Erk2, JNK, or p38; and tyrosine phosphorylation of p62$^{dok}$ and its association with SHIP and RasGAP can be assayed.

One exemplary assay for determining the inhibition of FcER1 induced mast cell activation by the FcγRIIB antibodies of the combinations of the invention can comprise of the following: transfecting RBL-H23 cells with human FcγRIIB; sensitizing the RBL-H23 cells with IgE; stimulating RBL-H23 cells with either F(ab')$_2$ of rabbit anti-mouse IgG (to aggregate FcER1 alone and elicit FcεRI-mediated signaling, as a control), or stimulating RBL-H23 cells with whole rabbit anti-mouse IgG to (to coaggregate FcγRIIB and FcεRI, resulting in inhibition of FcεRI-mediated signaling). Cells that have been stimulated with whole rabbit anti-mouse IgG antibodies can be further pre-incubated with the antibodies of the invention. Measuring FcεRI-dependent activity of cells that have been pre-incubated with the antibodies of the invention and cells that have not been pre-incubated with the antibodies of the invention, and comparing levels of FcεRI-dependent activity in these cells, would indicate a modulation of FcεRI-dependent activity by the antibodies of the invention.

The exemplary assay described above can be for example, used to identify antibodies that block ligand (IgG) binding to FcγRIIB receptor and antagonize FcγRIIB-mediated inhibition of FcεRI signaling by preventing coaggregating of FcγRIIB and FcεRI. This assay likewise identifies antibodies that enhance coaggregation of FcγRIIB and FcεRI and agonize FcγRIIB-mediated inhibition of FcεRI signaling by promoting coaggregating of FcγRIIB and FcεRI.

In a preferred embodiment, FcεRI-dependent activity is at least one or more of the following: modulation of downstream signaling molecules (e.g., modulation of phosphorylation state of FcγRIIB, modulation of SHIP recruitment, modulation of MAP Kinase activity, modulation of phosphorylation state of SHIP, modulation of SHIP and Shc association SHIP and Shc, modulation of the phosphorylation state of p62$^{dok}$, modulation of p62$^{dok}$ and SHIP association, modulation of p62$^{dok}$ and RasGAP association, modulation of calcium mobilization, modulation of degranulation, and modulation of cytokine production. In yet another preferred embodiment, FcεRI-dependent activity is serotonin release and/or extracellular Ca$^{++}$ influx and/or IgE dependent mast cell activation. It is known to one skilled in the art that coaggregation of FcγRIIB and FcεRI stimulates FcγRIIB tyrosine phosphorylation, stimulates recruitment of SHIP, stimulates SHIP tyrosine phosphorylation and association with Shc, and inhibits activation of MAP kinase family members including, but not limited to, Erk1, Erk2, JNK, p38. It is also known to those skilled in the art that coaggregation of FcγRIIB and FcεRI stimulates enhanced tyrosine phosphorylation of p62$^{dok}$ and its association with SHIP and RasGAP.

The anti-FcγRIIB antibodies of the combinations of the invention can be characterized for their ability to modulate an IgE mediated response by monitoring and/or measuring degranulation of mast cells or basophils, preferably in a cell-based assay. Preferably, mast cells or basophils for use in such assays have been engineered to contain human FcγRIIB using standard recombinant methods known to one skilled in the art. In a specific embodiment the anti-FcγRIIB antibodies of the combinations of the invention are characterized for their ability to modulate an IgE mediated response in a cell-based-hexosaminidase (enzyme contained in the granules) release assay. -hexosaminidase release from mast cells and basophils is a primary event in acute allergic and inflammatory condition (Aketani et al. (2001) "*Correlation Between Cytosolic Calcium Concentration And Degranulation In RBL-2H3 Cells In The Presence Of Various Concentrations Of Antigen-Specific IgEs*," Immunol. Lett. 75: 185-189; Aketani et al. (2000) "*A Screening Method For Antigen-Specific IgE Using Mast Cells Based On Intracellular Calcium Signaling*," Anal. Chem. 72: 2653-2658). Release of other inflammatory mediators including but not limited to serotonin and histamine may be assayed to measure an IgE mediated response in accordance with the methods of the invention. Although not intending to be bound by a particular mechanism of action, release of granules such as those containing-hexosaminidase from mast cells and basophils is an intracellular calcium concentration dependent process that is initiated by the cross-linking of Fc RIs with multivalent antigen.

One exemplary assay for characterizing the anti-FcγRIIB antibodies of the combinations of the invention in mediating an IgE mediated response is a -hexosaminidase release assay comprising the following: transfecting RBL-H23 cells with human Fc RIIB; sensitizing the cells with mouse IgE alone or with mouse IgE and an anti-Fc RIIB antibody of the invention; stimulating the cells with various concentrations of goat anti-mouse F(ab)$_2$, preferably in a range from 0.03 g/mL to g/mL for about 1 hour; collecting the supernatant; lysing the cells; and measuring the -hexosaminidase activity released in the supernatant by a colorometric assay, e.g., using p-nitrophenyl N-acetyl-1-D-glucosaminide. The released-hexosaminidase activity is expressed as a percentage of the released activity to the total activity. The released-hexosaminidase activity will be measured and compared in cells treated with antigen alone; IgE alone; IgE and an anti-Fc RIIB antibody of the invention. Although not intending to be bound by a particular mechanism of action, once cells are sensitized with mouse IgE alone and challenged with F(ab)$_2$ fragments of a polyclonal goat anti-mouse IgG, aggregation and cross linking of Fc RI occurs since the polyclonal antibody recognizes the light chain of the murine IgE bound to the Fc RI; which in turn leads to mast cell activation and degranulation. On the other hand, when cells are sensitized with mouse IgE and an anti-Fc RIIB antibody of the combinations of the invention and challenged with F(ab)$_2$ fragments of a polyclonal goat anti-mouse IgG; cross linking of Fc RI and Fc RIIB occurs, resulting in inhibition of Fc RI induced degranulation. In either case, goat anti mouse F(ab)$_2$ induces a dose-dependent-hexoaminidase release. In some embodiments, the anti-FcγRIIB antibodies bound to the Fc RIIB receptor and cross linked to Fc RI do not affect the activation of the inhibitory pathway, i.e., there is no alteration in the level of degranulation in the presence of an anti-Fc RIIB antibody. In other embodiments, the anti-FcγRIIB antibodies mediate a stronger activation of the inhibitory receptor, Fc RIIB, when bound by the anti-Fc RIIB antibody, allowing effective cross linking to Fc RI and activation of the inhibitory pathway of homo-aggregated Fc RIIB.

The effect of the anti-Fc RIIB antibodies of the combinations of the invention on IgE mediated cell response can be characterized using calcium mobilization assays using methodologies known to one skilled in the art. An exemplary calcium mobilization assay may comprise the following: priming basophils or mast cells with IgE; incubating the cells with a calcium indicator, e.g., Fura 2; stimulating cells as described supra; and monitoring and/or quantitating intracellular calcium concentration for example by using flow cytometry. The invention encompasses monitoring and/or quantitating intracellular calcium concentration by any method known to one skilled in the art see, e.g., Aketani et al. (2001) "*Correlation Between Cytosolic Calcium Concentration And Degranulation In RBL-2H3 Cells In The Presence Of Various Concentrations Of Antigen-Specific IgEs*," Immunol. Lett. 75: 185-189; Oka et al. (2002) "*FcRI Cross-Linking-Induced Actin Assembly Mediates Calcium Signalling In RBL-2H3 Mast Cells*," British J. of Pharm. 136:837-845; Ott (2002) "*Downstream Of Kinase, p62(dok), Is A Mediator Of Fc gamma IIB Inhibition Of Fc Epsilon RI Signaling*," J. Immunol. 162(9):4430-4439 and Mahmoud et al. (2001) "*Microdomains Of High Calcium Are Not Required For Exocytosis In RBL-2H3 Mucosal Mast Cells*," J. Cell Biol., 153(2):339-350; all of which are incorporated herein by reference.

In preferred embodiments, anti-Fc RIIB antibodies of the combinations of the invention inhibit IgE mediated cell activation. In other embodiments, the anti-Fc RIIB antibodies of the combinations of the invention block the inhibitory pathways regulated by Fc RIIB or block the ligand binding site on FcγRIIB and thus enhance immune response.

In one particular embodiment, the anti-FcγRIIB antibodies of the combinations block the ligand binding site of FcγRIIB. In a further specific embodiment, the blocking activity can block the negative regulation of immune-complex-triggered activation and consequently enhance the immune response. In a further specific embodiment, the enhanced immune response is an increase in antibody-dependent cellular response. In another specific embodiment, the anti-FcγRIIB antibodies of the combinations of the invention block crosslinking of FcγRIIB receptors to B cell and/or Fc receptors, leading to B cell, mast cell, dendritic cell, or macrophage activation.

The ability to study human mast cells has been limited by the absence of suitable long term human mast cell cultures. Recently two novel stem cell factor dependent human mast cell lines, designated LAD 1 and LAD2, were established from bone marrow aspirates from a patient with mast cell sarcoma/leukemia (Kirshenbaum et al. (2003) "*Characterization Of Novel Stem Cell Factor Responsive Human Mast Cell Lines LAD 1 And 2 Established From A Patient With Mast Cell Sarcoma/Leukemia; Activation Following Aggregation Of FcepsilonRI Or FcgammaRI*," Leukemia research, 27(8):677-682, which is incorporated herein by reference in its entirety.). Both cell lines have been described to express FcER1 and several human mast cell markers. The invention encompasses using LAD 1 and 2 cells in the methods of the invention for assessing the effect of the antibodies of the invention on IgE mediated responses. In a specific embodiment, cell-based β-hexosaminidase release assays such as those described supra may be used in LAD cells to determine any modulation of the IgE-mediated response by the anti-Fc RIIB antibodies of the combinations of the invention. In an exemplary assay, human mast cells, e.g., LAD 1, are primed with chimaeric human IgE anti-nitrophenol (NP) and challenged with BSA-NP, the polyvalent antigen, and cell degranulation is monitored by measuring the β-hexosaminidase released in the supernatant (Kirshenbaum et al. (2003) "*Characterization Of Novel Stem Cell Factor Responsive Human Mast Cell Lines LAD 1 And 2 Established From A Patient With Mast Cell Sarcoma/Leukemia; Activation Following Aggregation Of FcepsilonRI Or FcgammaRI*," Leukemia research, 27(8):677-682, which is incorporated herein by reference in its entirety).

In some embodiments, if human mast cells have a low expression of endogenous FcγRIIB, as determined using standard methods known in the art, e.g., FACS staining, it may be difficult to monitor and/or detect differences in the activation of the inhibitory pathway mediated by the anti-Fc RIIB antibodies of the combinations of the invention. The invention thus encompasses alternative methods, whereby the Fc RIIB expression may be upregulated using cytokines and particular growth conditions. FcγRIIB has been described to be highly up-regulated in human monocyte cell lines, e.g., THP1 and U937, (Tridandapani et al. (2002) "*Regulated Expression And Inhibitory Function Of FcRIIb In Human Monocytic Cells*," J. Biol. Chem., 277(7): 5082-5089) and in primary human monocytes (Pricop et al. (2001) "*Differential Modulation Of Stimulatory And Inhibitory Fc Gamma Receptors On Human Monocytes By Th1 And Th2 Cytokines*," J. Immunol., 166: 531-537) by IL-4. Differentiation of U937 cells with dibutyryl cyclic AMP has been described to increase expression of FcγRII (Cameron et al. (2002) "*Differentiation Of The Human Monocyte Cell Line, U937, With Dibutyryl CyclicAMP Induces The Expression Of The Inhibitory Fc Receptor, FcgammaRIIB*," Immunology Letters 83, 171-179). Thus the endogenous FcγRIIB expression in human mast cells for use in the methods of the invention may be up-regulated using cytokines, e.g., IL-4, IL-13, in order to enhance sensitivity of detection.

The anti-FcγRIIB antibodies of the combinations of the invention can be characterized for inhibition of B cell receptor (BCR)-mediated signaling. BCR-mediated signaling can include at least one or more down stream biological responses, such as activation and proliferation of B cells, antibody production, etc. Coaggregation of FcγRIIB and BCR leads to inhibition of cell cycle progression and cellular survival. Further, coaggregation of FcγRIIB and BCR leads to inhibition of BCR-mediated signaling.

Specifically, BCR-mediated signaling comprises at least one or more of the following: modulation of down stream signaling molecules (e.g., phosphorylation state of FcγRIIB, SHIP recruitment, localization of Btk and/or PLCγ, MAP kinase activity, recruitment of Akt (anti-apoptotic signal), calcium mobilization, cell cycle progression, and cell proliferation.

Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, $Ins(1,4,5)P_3$ production, and Erk and Akt phosphorylation (Brauweiler et al. (2001) "*Partially Distinct Molecular Mechanisms Mediate Inhibitory FcgammaRIIB Signaling In Resting And Activated B Cells*," J. Immunol. 167(1): 204-211). Accordingly, ex vivo B cells from SHIP deficient mice can be used to characterize the antibodies of the invention. One exemplary assay for determining FcγRIIB-mediated inhibition of BCR signaling by the antibodies of the combinations of the invention can comprise the following: isolating splenic B cells from SHIP deficient mice, activating said cells with lipopolysachharide, and stimulating said cells with either F(ab')$_2$ anti-IgM to aggregate BCR or with anti-IgM to coaagregate BCR with FcγRIIB. Cells that have been stimulated with intact anti-IgM to coaggregate BCR with FcγRIIB can be further pre-incubated with the FcγRIIB antibodies of the combinations of the invention. FcγRIIB-dependent activity of cells can be measured by standard techniques known in the art. Comparing the level of FcγRIIB-dependent activity in cells that have been pre-incubated with the FcγRIIB antibodies of the combinations of the invention and cells that have not been pre-incubated, and comparing the levels would indicate a modulation of FcγRIIB-dependent activity by the antibodies of the invention.

Measuring FcγRIIB-dependent activity can include, for example, measuring intracellular calcium mobilization by flow cytometry, measuring phosphorylation of Akt and/or Erk, measuring BCR-mediated accumulation of PI(3,4,5)P$_3$, or measuring FcγRIIB-mediated proliferation B cells.

The assays can be used, for example, to identify antibodies that modulate

FcγRIIB-mediated inhibition of BCR signaling by blocking the ligand (IgG) binding site to FcγRIIB receptor and antagonizing FcγRIIB-mediated inhibition of BCR signaling by preventing coaggregation of FcγRIIB and BCR. The assays can also be used to identify antibodies that enhance coaggregation of FcγRIIB and BCR and agonize FcγRIIB-mediated inhibition of BCR signaling.

The anti-FcγRIIB antibodies of the combinations of the invention can be characterized for FcγRII-mediated signaling in human monocytes/macrophages. Coaggregation of FcγRIIB with a receptor bearing the immunoreceptor tyrosine-based activation motif (ITAM) acts to down-regulate FcγR-mediated phagocytosis using SHIP as its effector (Tridandapani et al. (2000) "*The Adapter Protein LAT Enhances Fc Receptor-Mediated Signal Transduction In Myeloid Cells,*" J. Biol. Chem. 275: 20480-20487). Coaggregation of FcγRIIA with FcγRIIB results in rapid phosphorylation of the tyrosine residue on FcγRIIB's ITIM motif, leading to an enhancement in phosphorylation of SHIP, association of SHIP with Shc, and phosphorylation of proteins having the molecular weight of 120 and 60-65 kDa. In addition, coaggregation of FcγRIIA with FcγRIIB results in down-regulation of phosphorylation of Akt, which is a serine-threonine kinase that is involved in cellular regulation and serves to suppress apoptosis.

The anti-FcγRIIB antibodies of the combinations of the invention can be further characterized for their inhibition of FcγR-mediated phagocytosis in human monocytes/macrophages. For example, cells from a human monocytic cell line, THP-1 can be stimulated either with Fab fragments of mouse monoclonal antibody IV.3 against FcγRII and goat anti-mouse antibody (to aggregate FcγRIIA alone), or with whole IV.3 mouse monoclonal antibody and goat anti-mouse antibody (to coaggregate FcγRIIA and FcγRIIB). In this system, modulation of down stream signaling molecules, such as tyrosine phosphorylation of FcγRIIB, phosphorylation of SHIP, association of SHIP with Shc, phosphorylation of Akt, and phosphorylation of proteins having the molecular weight of 120 and 60-65 kDa can be assayed upon addition of antibodies of the invention to the stimulated cells. In addition, FcγRIIB-dependent phagocytic efficiency of the monocyte cell line can be directly measured in the presence and absence of the antibodies of the invention.

Another exemplary assay for determining inhibition of FcγR-mediated phagocytosis in human monocytes/macrophages by the FcγRIIB antibodies of the combinations of the invention can comprise the following: stimulating THP-1 cells with either Fab of IV.3 mouse anti-FcγRII antibody and goat anti-mouse antibody (to aggregate FcγRIIA alone and elicit FcγRIIA-mediated signaling); or with mouse anti-FcγRII antibody and goat anti-mouse antibody (to coaggregate FcγRIIA and FcγRIIB and inhibiting FcγRIIA-mediated signaling. Cells that have been stimulated with mouse anti-FcγRII antibody and goat anti-mouse antibody can be further pre-incubated with the antibodies of the invention. Measuring FcγRIIA-dependent activity of stimulated cells that have been pre-incubated with antibodies of the invention and cells that have not been pre-incubated with the antibodies of the invention and comparing levels of FcγRIIA-dependent activity in these cells would indicate a modulation of FcγRIIA-dependent activity by the antibodies of the invention.

The exemplary assay described can be used for example, to identify antibodies that block ligand binding of FcγRIIB receptor and antagonize FcγRIIB-mediated inhibition of FcγRIIA signaling by preventing coaggregation of FcγRIIB and FcγRIIA. This assay likewise identifies antibodies that enhance coaggregation of FcγRIIB and FcγRIIA and agonize FcγRIIB-mediated inhibition of FcγRIIA signaling.

The function of the antibodies of the combinations of the invention can be characterized by measuring the ability of THP-1 cells to phagocytose fluoresceinated IgG-opsonized sheep red blood cells (SRBC) by methods previously described (Tridandapani et al. (2000) "*The Adapter Protein LAT Enhances Fc Receptor-Mediated Signal Transduction In Myeloid Cells,*" J. Biol. Chem. 275: 20480-20487). For example, an exemplary assay for measuring phagocytosis comprises of: treating THP-1 cells with the antibodies of the invention or with a control antibody that does not bind to FcγRII, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate a modulation of FcγRIIA-dependent activity by the antibodies of the invention. This assay can be used to identify, for example, antibodies that block ligand binding of FcγRIIB receptor and antagonize FcγRIIB-mediated inhibition of phagocytosis. This assay can also identify antibodies that enhance FcγRIIB-mediated inhibition of FcγRIIA signaling.

In a preferred embodiment, the FcγRIIB antibodies of the combinations of the invention modulate FcγRIIB-dependent activity in human monocytes/macrophages in at least one or more of the following ways: modulation of downstream signaling molecules (e.g., modulation of phosphorylation state of FcγRIIB, modulation of SHIP phosphorylation, modulation of SHIP and Shc association, modulation of phosphorylation of Akt, modulation of phosphorylation of additional proteins around 120 and 60-65 kDa) and modulation of phagocytosis.

The FcγRIIB antibodies of the combinations of the invention can be characterized using assays known to those skilled in the art for identifying the effect of the antibodies on effector cell function of therapeutic antibodies, such as anti-CD20 antibodies of the combinations of the invention, e.g., their ability to enhance tumor-specific ADCC activity of therapeutic antibodies. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al. (2000) "*Assays For Antibody-Dependent Cell-Mediated Cytotoxicity (ADCC) And Reverse ADCC (redirected cytotoxicity) In Human Natural Killer Cells*," Methods Mol. Biol. 121: 179-192; Baggiolini et al. (1998) "*Cellular Models For The Detection And Evaluation Of Drugs That Modulate Human Phagocyte Activity*," Experientia, 44(10): 841-8; Lehmann et al. (2000) "*Phagocytosis: Measurement By Flow Cytometry*," J. Immunol. Methods, 243(1-2): 229-242; Brown (1994) "*In Vitro Assays Of Phagocytic Function Of Human Peripheral Blood Leukocytes: Receptor Modulation And Signal Transduction*," Methods Cell Biol., 45: 147-164; Munn et al. (1990) "*Phagocytosis Of Tumor Cells By Human Monocytes Cultured In Recombinant Macrophage Colony-Stimulating Factor*," J. Exp. Med., 172: 231-237, Abdul-Majid et al. (2002) "*Fc Receptors Are Critical For Autoimmune Inflammatory Damage To The Central Nervous System In Experimental Autoimmune Encephalomyelitis*," Scand. J. Immunol. 55: 70-81; Ding et al. (1998) "*Two Human T Cell Receptors Bind In A Similar Diagonal Mode To The HLA-A2/Tax Peptide Complex Using Different TCR Amino Acids*," Immunity 8:403-411, each of which is incorporated by reference herein in its entirety).

Antibodies of the combinations of the invention can be assayed for their effect on FcγR-mediated ADCC activity of therapeutic antibodies in effector cells, e.g., natural killer cells, using any of the standard methods known to those skilled in the art (See e.g., Perussia et al. (2000) "*Assays For Antibody-Dependent Cell-Mediated Cytotoxicity (ADCC) And Reverse ADCC (redirected cytotoxicity) In Human Natural Killer Cells*," Methods Mol. Biol. 121: 179-192). "Antibody-dependent cell-mediated cytotoxicity" and "ADCC" as used herein carry their ordinary and customary meaning in the art and refer to an in vitro cell-mediated reaction in which nonspecific cytotoxic cells that express Fc R5 (e.g., monocytic cells such as Natural Killer (NK) cells and macrophages) recognize bound antibody on a target cell and subsequently cause lysis of the target cell. In principle, any effector cell with an activating Fc R can be triggered to mediate ADCC. The primary cells for mediating ADCC are NK cells which express only Fc RIII, whereas monocytes, depending on their state of activation, localization, or differentiation, can express Fc RI, Fc RII, and Fc RIII. For a review of FcγR expression on hematopoietic cells see, e.g., Ravetch J. V. et al. (1991) "*Fc Receptors*," Annu. Rev. Immunol. 9: 457-92, which is incorporated herein by reference in its entirety.

Effector cells are leukocytes which express one or more Fc Rs and perform effector functions. Preferably, the cells express at least Fc RIII and perform ADCC effector function. Effector cells that may be used in the methods of the invention include but are not limited to peripheral blood mononuclear cells (PBMC), natural killer (NK) cells, monocytes, and neutrophils; with PBMCs and NK cells being preferred. The effector cells may be isolated from a native source thereof, e.g., from blood or PBMCs as described herein. Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. For example, PBMCs may be isolated by layering whole blood onto Ficoll-Hypaque and spinning the cells at 500 g, at room temperature for 30 minutes. The leukocyte layer can be harvested as effector cells. Other effector cells that may be used in the ADCC assays of the invention include but are not limited to monocyte-derived macrophages (MDMs). MDMs that are used as effector cells in the methods of the invention, are preferably obtained as frozen stocks or used fresh, (e.g., from Advanced Biotechnologies, Md.). In most preferred embodiments, elutriated human monocytes are used as effector cells in the methods of the invention. Elutriated human monocytes express activating receptors, FcγRIIIA and FcγRIIA and the inhibitory receptor, FcγRIIB. Human monocytes are commercially available and may be obtained as frozen stocks, thawed in basal medium containing 10% human AB serum or in basal medium with human serum containing cytokines. Levels of expression of FcγRs in the cells may be directly determined; e.g., using FACS analysis. Alternatively, cells may also be allowed to mature to macrophages in culture. The level of FcγRIIB expression may be increased in macrophages. Antibodies that may be used in determining the expression level of FcγRs include but are not limited to anti-human FcγRIIA antibodies, e.g., IV.3-FITC; anti-FcγRI antibodies, e.g., 32.2 FITC; and anti-FcγRIIIA antibodies, e.g., 3G8-PE.

Target cells used in the ADCC assays of the invention include, but are not limited to, B-lymphocytes; cells derived from Burkitts lymphoma, e.g., Raji cells with ATCC accession number CCL-86 (see, e.g., Epstein et al. (1965) "*Characteristics And Mode Of Growth Of Tissue Culture Strain (EB1) Of Human Lymphoblasts From Burkitt's Lymphoma*," J. Natl. Cancer Inst. 34: 231-240), Daudi cells with ATCC accession number CCL-213 (see, e.g., Klein et al. (1968) "*Surface IgM-Kappa Specificity On A Burkitt Lymphoma Cell In Vivo And In Derived Culture Lines*," Cancer Res. 28: 1300-1310). The target cells must be recognized by the antigen binding site of the antibody to be assayed. The target cells for use in the methods of the invention may have low, medium, or high expression level of a cancer antigen. The expression levels of the cancer antigen may be determined using common methods known to one skilled in the art, e.g., FACS analysis.

An exemplary assay for determining the effect of the antibodies of the invention on the ADCC activity of therapeutic antibodies is based on a $^{51}$Cr release assay comprising of: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell lysis); preferably, the target cells express one or more tumor antigens, osponizing the target cells with one or more antibodies that immunospecifically bind the tumor antigens expressed on the cell surface of the target cells, in the presence and absence of an antibody of the invention, e.g., 2B6, 3H7, 8B5.3.4, combining the opsonized radiolabeled target cells with effector cells in a microtitre plate at an appropriate ratio of target cells to effector cells; incubating the mixture of cells preferably for 16-18 hours, preferably at 37° C.; collecting supernatants; and analyzing the radioactivity in the supernatant samples. The cytotoxicity of the therapeutic antibodies in the presence and absence of the antibodies of the invention can then be determined, for example using the following formula: Percent specific lysis=(Experimental lysis-antibody-independent lysis/maximal lysis−antibody independent lysis)× 100%. A graph can be generated by varying either the target: effector cell ratio or antibody concentration.

The antibodies of the combinations of the invention can also be characterized for antibody dependent cellular cytotoxicity (ADCC) in accordance with the method described earlier, see, e.g., Ding et al. (1998) "*Two Human T Cell Receptors Bind In A Similar Diagonal Mode To The HLA-A2/Tax Peptide Complex Using Different TCR Amino Acids*," Immunity 8:403-411; which is incorporated herein by reference in its entirety.

In some embodiments, the invention encompasses characterizing the function of the antibodies of the combinations of the invention in enhancing ADCC activity of therapeutic antibodies in an in vitro based assay and/or in an animal model.

Preferably, the ADCC assays are done using more than one cancer cell line, characterized by the expression of at least one cancer antigen, wherein the expression level of the cancer antigen is varied among the cancer cell lines used. Although not intending to be bound by a particular mechanism of action, performing ADCC assays in more than one cell line wherein the expression level of the cancer antigen is varied, will allow determination of stringency of tumor clearance of the antibodies of the invention. In one embodiment, the ADCC assays are done using cancer cell lines with different levels of expression of a cancer antigen.

An exemplary assay for determining the ADCC activity of the tumor specific antibodies in the presence and absence of the antibodies of the combinations of the invention is a non-radioactive europium based fluorescent assay (BATDA, Perkin Elmer) and may comprise the following: labeling the targets cells with an acteoxylmethyl ester of fluorescence-enhancing ester that forms a hydrophilic ligand (TDA) with the membrane of cells by hydrolysis of the esters; this complex is unable to leave the cell and is released only upon lysis of the cell by the effectors; adding the labeled targets to the effector cells in presence of anti-tumor antibodies and an antibody of the invention; incubating the mixture of the target and effector cells a for 6 to 16 hours, preferably at 37° C. The extent of ADCC activity can be assayed by measuring the amount of ligand that is released and interacts with europium (DELFIA reagent; PerkinElmer). The ligand and the europium form a very stable and highly fluorescent chelate (EuTDA) and the measured fluorescence is directly proportional to the number of cells lysed. Percent specific lysis can be calculated using the formula: (Experimental lysis-antibody-independent lysis/maximal lysis antibody-independent lysis×100%).

In some embodiments, if the sensitivity of the fluorescence-based ADCC assay is too low to detect ADCC activity of the therapeutic antibodies, the invention encompasses radioactive-based ADCC assays, such as $^{51}$Cr release assay. Radioactive-based assays may be done instead of or in combination with fluorescent-based ADCC assays.

An exemplary $^{51}$Cr release assay for characterizing the antibodies of the combinations of the invention can comprise the following: labeling 1–2×10$^6$ target cells such as OVCAR-3 cells with $^{51}$Cr; opsonizing the target cells with antibodies 4D5 and CC49 in the presence and absence of an antibody of the invention and adding 5×10$^3$ cells to 96 well plate. Preferably 4D5 and CC49 are at a concentration varying from 1-15 ng/mL; adding the opsonized target cells to monocyte-derived macrophages (MDM) (effector cells); preferably at a ratio varying from 10:1 to 100:1; incubating the mixture of cells for 16-18 hours at 37° C.; collecting supernatants; and analyzing the radioactivity in the supernatant. The cytotoxicity of 4D5 and CC49 in the presence and absence of an antibody of the invention can then be determined, for example using the following formula percent specific lysis=(experimental lysis-antibody independent lysis/maximal lysis-antibody independent lysis)×100%.

In some embodiments, the in vivo activity of the antibodies of the combinations of the invention is determined in xenograft human tumor models particularly B cell tumors. Tumors may be established using any of the cancer cell lines described supra. In some embodiments, the tumors will be established with two cancer cell lines, wherein the first cancer cell line is characterized by a low expression of a cancer antigen and a second cancer cell line, wherein the second cancer cell line is characterized by a high expression of the same cancer antigen. Tumor clearance may then be determined using methods known to one skilled in the art, using an anti-tumor antibody which immunospecifically binds the cancer antigen on the first and second cancer cell line, and an appropriate mouse model, e.g., a Balb/c nude mouse model (e.g., Jackson Laboratories, Taconic), with adoptively transferred human monocytes and MDMs as effector cells. Any of the antibodies of the combinations described supra such as the Fc RIIB antibodies, may then be tested in this animal model to evaluate the role of anti-Fc RIIB antibody of the invention in tumor clearance. Mice that may be used in the invention include for example Fc RIII–/– (where Fc RIIIA is knocked out); Fc–/– nude mice (where Fc RI and Fc RIIIA are knocked out); or human Fc RIIB knock in mice or a transgenic knock-in mice, where mouse fcgr2 and fcgr3 1 oci on chromosome 1 are inactivated and the mice express human Fc RIIA, human Fc RIIA human Fc RIIB, human Fc RIIC, human Fc RIIIA, and human Fc RIIIB An exemplary method for testing the in vivo activity of an antibody of the combinations of the invention may comprise the following: establishing a xenograft murine model using a cancer cell line characterized by the expression of a cancer antigen and determining the effect of an antibody of the combinations of the invention on an antibody specific for the cancer antigen expressed in the cancer cell line in mediating tumor clearance.

In alternative embodiments, human FcγRIIB "knock in" mice expressing human FcγRIIB on murine effector cells may be used in establishing the in vivo activity of the antibodies of the combinations of the invention, rather than adoptively transferring effector cells. Founder mice expressing the human FcγRIIB may be generated by "knocking in" the human FcγRIIB onto the mouse FcγRIIB locus. The founders can then be back-crossed onto the nude background and will express the human FcγRIIB receptor. The resulting murine effector cells will express endogenous activating FcγRI and FcγRIIIA and inhibitory human FcγRIIB receptors.

Preferably, immunohistochemistry and histochemistry is performed on ascites and pleural effusion of patients to analyze structural characteristics of the neoplasia. Such methods are known to one skilled in the art and encompassed within the invention. The markers that may be monitored include for example cytokeratin (to identify ovarian neoplastic and mesothelial cells from inflammatory and mesenchymal cells); calretinin (to separate mesothelial from Her2neu positive neoplastic cells); and CD45 (to separate inflammatory cells from the rest of the cell population in the samples). Additional markers that may be followed include CD3 (T cells), CD20 (B cells), CD56 (NK cells), and CD14 (monocytes). It will be appreciated by one skilled in the art that the immunohistochemistry and histochemistry methods described supra, are analogously applied to any tumor cell for use in the methods of the invention. After s.c. inoculation of tumor cells, mice are followed for clinical and anatomical changes. As needed, mice may be necropsied to correlate total tumor burden with specific organ localization.

Preferably, the antibodies of the invention have an enhanced efficacy in decreasing tumor relative to Fc RIIB or CD20 antibodies alone when administered at the same dose, e.g., 10 g/g, over a time period of at least 14 days, at least 21 days, at least 28 days, or at least 35 days. In most preferred embodiments, the combinations of Fc RIIB antibodies and CD20 antibodies reduce tumor size by at least 10 fold, at least 100 fold, at least 1000 fold relative to administration of the Fc RIIB antibody, CD20 antibody or other cancer therapeutic antibody at the same dose. In yet another preferred embodiment, the antibodies of the combinations of the invention completely abolish the tumor.

I. Polynucleotides Encoding an Antibody

The present invention also includes polynucleotides that encode the antibodies of the invention (e.g., Fc RIIB mouse monoclonal antibody produced from clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively), or other monoclonal antibodies produced by immunization methods of the invention, and humanized versions thereof, and methods for producing same. In some embodiments, the Fc RIIB antibody is a monoclonal antibody produced by MGX D675 (ATCC accession number PTA-7609; deposited May 23, 2006, which is incorporated herein by reference).

In certain embodiments, a nucleic acid sequence of the invention encodes a H2B6VH-3a amino acid sequence comprising:

```
                                           (SEQ ID NO: 68)
QVQLVQSGAE VKKPGASVKV SCKASGYTFT

NYWIHWVRQA PGQGLEWIGV IDPSDTYPNY

NKKFKGRVTM TVDTSTSTAY MELRSLRSDD

TAVYYCARNG DSDYYSGMDY WGQGTTVTVS

S.
```

In specific embodiments, the nucleotide sequence comprises a H2B6VH-3a nucleotide sequence comprising:

```
                                           (SEQ ID NO: 67)
CAGGTTCAGC TGGTGCAGTC TGGAGCTGAG

GTGAAGAAGC CTGGGGCCTC AGTGAAGGTC

TCCTGCAAGG CTTCTGGTTA CACCTTTACC

AACTACTGGA TACACTGGGT GCGACAGGCC

CCTGGACAAG GGCTTGAGTG GATTGGAGTG

ATTGATCCTT CTGATACTTA TCCAAATTAC

AATAAAAAGT TCAAGGGCAG AGTCACCATG

ACCGTAGACA CATCCACGAG CACAGCCTAC

ATGGAGCTGA GGAGCCTGAG ATCTGACGAC

ACGGCCGTGT ATTACTGTGC GAGAAACGGT
```

```
-continued
GATTCCGATT ATTACTCTGG TATGGACTAC

TGGGGGCAAG GGACCACGGT CACCGTCTCC

CA.
```

In other embodiments, a nucleic acid sequence of the invention encodes a H2B6VL-5 amino acid sequence comprising:

```
                                           (SEQ ID NO: 62)
EIVLTQSPDF QSVTPKEKVT FTCRTSQSIG

TNIHWYQQKP DQSPKLLIKE VSESISGVPS

RFSGSGSGTD FTLTINSLEA EDAATYYCQQ

SNTWPFTFGG GTKVEIK.
```

In specific embodiments, a nucleotide sequence of the invention comprises a Hu2B6VL-5 nucleotide sequence comprising:

```
                                           (SEQ ID NO: 63)
GAAATTGTGC TGACTCAGTC TCCAGACTTT

CAGTCTGTGA CTCCAAAGGA GAAAGTCACC

TTCACCTGCA GGACCAGTCA GAGCATTGGC

ACAAACATAC ACTGGTACCA GCAGAAACCA

GATCAGTCTC CAAAGCTCCT CATCAAGGAG

GTTTCTGAGT CTATCTCTGG AGTCCCATCG

AGGTTCAGTG GCAGTGGATC TGGGACAGAT

TTCACCCTCA CCATCAATAG CCTGGAAGCT

GAAGATGCTG CAACGTATTA CTGTCAACAA

AGTAATACCT GGCCGTTCAC GTTCGGCGGA

GGGACCAAGG TGGAGATCAA

A.
```

In certain embodiments, a nucleic acid sequence of the invention encodes a H2B6HC-3 amino acid sequence comprising SEQ ID NO: 70. In specific embodiments, the nucleotide sequence encodes a H2B6HC-3 nucleotide sequence comprising:

```
                                           (SEQ ID NO: 69)
CAGGTTCAGC TGGTGCAGTC TGGAGCTGAG

GTGAAGAAGC CTGGGGCCTC AGTGAAGGTC

TCCTGCAAGG CTTCTGGTTA CACCTTTACC

AACTACTGGA TACACTGGGT GCGACAGGCC

CCTGGACAAG GGCTTGAGTG GATTGGAGTG

ATTGATCCTT CTGATACTTA TCCAAATTAC

AATAAAAAGT TCAAGGGCAG AGTCACCATG

ACCGTAGACA CATCCACGAG CACAGCCTAC

ATGGAGCTGA GGAGCCTGAG ATCTGACGAC

ACGGCCGTGT ATTACTGTGC GAGAAACGGT

GATTCCGATT ATTACTCTGG TATGGACTAC
```

-continued

```
TGGGGGCAAG GGACCACGGT CACCGTCTCC
TCAGCCTCCA CCAAGGGCCC ATCGGTCTTC
CCCCTGGCAC CCTCCTCCAA GAGCACCTCT
GGGGGCACAG CGGCCCTGGG CTGCCTGGTC
AAGGACTACT TCCCCGAACC GGTGACGGTG
TCGTGGAACT CAGGCGCCCT GACCAGCGGC
GTGCACACCT TCCCGGCTGT CCTACAGTCC
TCAGGACTCT ACTCCCTCAG CAGCGTGGTG
ACCGTGCCCT CCAGCAGCTT GGGCACCCAG
ACCTACATCT GCAACGTGAA TCACAAGCCC
AGCAACACCA AGGTGGACAA GAGAGTTGAG
CCCAAATCTT GTGACAAAAC TCACACATGC
CCACCGTGCC CAGCACCTGA ACTCCTGGGG
GGACCGTCAG TCTTCCTCTT ACCCCCAAAA
CCCAAGGACA CCCTCATGAT CTCCCGGACC
CCTGAGGTCA CATGCGTGGT GGTGGACGTG
AGCCACGAAG ACCCTGAGGT CAAGTTCAAC
TGGTACGTGG ACGGCGTGGA GGTGCATAAT
GCCAAGACAA AGCCGCCGGA GGAGCAGTAC
AACAGCACGC TCCGTGTGGT CAGCATCCTC
ACCGTCCTGC ACCAGGACTG GCTGAATGGC
AAGGAGTACA AGTGCAAGGT CTCCAACAAA
GCCCTCCCAG CCCCCATCGA GAAAACCATC
TCCAAAGCCA AGGGCAGCC CCGAGAACCA
CAGGTGTACA CCCTGCCCCC ATCCCGGGAT
GAGCTGACCA AGAACCAGGT CAGCCTGACC
TGCCTGGTCA AAGGCTTCTA TCCCAGCGAC
ATCGCCGTGG AGTGGGAGAG CAATGGGCAG
CCGGAGAACA ACTACAAGAC CACGCCTCTC
GTGCTGGACT CCGACGGCTC CTTCTTCCTC
TACAGCAAGC TCACCGTGGA CAAGAGCAGG
TGGCAGCAGG GGAACGTCTT CTCATGCTCC
GTGATGCATG AGGCTCTGCA CAACCACTAC
ACGCAGAAGA GCCTCTCCCT GTCTCCGGGT AAATGA.
```

In other embodiments, a nucleic acid sequence of the invention encodes a H2B6 LC-5 amino acid sequence comprising SEQ ID NO: 66. In specific embodiments, the nucleotide sequence encodes a H2B6LC-5 nucleotide sequence comprising:

```
                              (SEQ ID NO: 65)
GAAATTGTGC TGACTCAGTC TCCAGACTTT
CAGTCTGTGA CTCCAAAGGA GAAAGTCACC
TTCACCTGCA GGACCAGTCA GAGCATTGGC
ACAAACATAC ACTGGTACCA GCAGAAACCA
GATCAGTCTC CAAAGCTCCT CATCAAGGAG
GTTTCTGAGT CTATCTCTGG AGTCCCATCG
AGGTTCAGTG GCAGTGGATC TGGGACAGAT
TTCACCCTCA CCATCAATAG CCTGGAAGCT
GAAGATGCTG CAACGTATTA CTGTCAACAA
AGTAATACCT GGCCGTTCAC GTTCGGCGGA
GGGACCAAGG TGGAGATCAA ACGAACTGTG
GCTGCACCAT CTGTCTTCAT CTTCCCGCCA
TCTGATGAGC AGTTGAAATC TGGAACTGCC
TCTGTTGTGT GCCTGCTGAA TAACTTCTAT
CCCAGAGAGG CCAAAGTACA GTGGAAGGTG
GATAACGCCC TCCAATCGGG TAACTCCCAG
GAGAGTGTCA CAGAGCAGGA CAGCAAGGAC
AGCACCTACA GCCTCAGCAG CACCCTGACG
CTGAGCAAAG CAGACTACGA GAAACACAAA
GTCTACGCCT GCGAAGTCAC CCATCAGGGC
CTGAGCTCGC CCGTCACAAA GAGCTTCAAC
AGGGGAGAGT
GTTAG.
```

In certain embodiments, a nucleic acid sequence of the invention encodes a 8B5.3.4 VH amino acid sequence comprising SEQ ID NO:71. In specific embodiments, the nucleotide sequence comprises a 8B5.3.4 VH nucleotide sequence comprising:

```
                     (SEQ ID NO: 73; see also FIG. 12)
GAAGTGAAGC TTGAGGAGTC TGGAGGAGGC
TTGGTGCAAC CTGGAGGATC CATGAAACTC
TCTTGTGAAG CCTCTGGATT CACTTTTAGT
GACGCCTGGA TGGACTGGGT CCGTCAGTCT
CCAGAGAAGG GGCTTGAGTG GGTTGCTGAA
ATTAGAAACA AAGCTAAAAA TCATGCAACA
TACTATGCTG AGTCTGTGAT AGGGAGGTTC
ACCATCTCAA GAGATGATTC CAAAAGTAGT
GTCTACCTGC AAATGAACAG CTTAAGAGCT
GAAGACACTG GCATTTATTA CTGTGGGGCT
CTGGGCCTTG ACTACTGGGG CCAAGGCACC
ACTCTCACAG TCTCCTCG.
```

In other embodiments, a nucleic acid sequence of the invention encodes a 8B5.3.4 VL amino acid sequence comprising SEQ ID NO:72. In specific embodiments, a nucleotide sequence of the invention comprises a 8B5.3.4 VL nucleotide sequence comprising:

(SEQ ID NO:74; see also FIG. 11)
GACATTCAGA TGACACAGTC TCCATCCTCC

CTACTTGCGG CGCTGGGAGA AAGAGTCAGT

CTCACTTGTC GGGCAAGTCA GGAAATTAGT

GGTTACTTAA GCTGGCTTCA GCAGAAACCA

GATGGAACTA TTAAACGCCT GATCTACGCC

GCATCCACTT TAGATTCTGG TGTCCCAAAA

AGGTTCAGTG GCAGTGAGTC TGGGTCAGAT

TATTCTCTCA CCATCAGCAG TCTTGAGTCT

GAAGATTTTG CAGACTATTA CTGTCTACAA

TATTTTAGTT ATCCGCTCAC GTTCGGTGCT

GGGACCAAGC TGGAGCTGAA A.

The invention also provides combinations of CD20 and Fc RIIB antibodies comprising the above-referenced amino acid sequences.

The present invention encompasses the polynucleotide encoding the heavy chain variable region of the 2B6 antibody, with ATCC accession number PTA-4591, comprising:

(SEQ ID NO: 27)
CAGGTCCAAT TGCAGCAGCC TGTGACTGAG

CTGGTGAGGC CGGGGCTTC AGTGATGTTG

TCCTGCAAGG CTTCTGACTA CCCCTTCACC

AACTACTGGA TACACTGGGT AAAGCAGAGG

CCTGGACAAG GCCTGGAGTG GATCGGAGTG

ATTGATCCTT CTGATACTTA TCCAAATTAC

AATAAAAAGT TCAAGGGCAA GGCCACATTG

ACTGTAGTCG TATCCTCCAG CACAGCCTAC

ATGCAGCTCA GCAGCCTGAC ATCTGACGAT

TCTGCGGTCT ATTACTGTGC AAGAAACGGT

GATTCCGATT ATTACTCTGG TATGGACTAC

TGGGGTCAAG GAACCTCAGT CACCGTCTCC

TCA.

The present invention also encompasses the polynucleotide encoding the light chain variable region of the 2B6 antibody with ATCC accession number PTA-4591, comprising:

(SEQ ID NO: 25)
GACATCTTGC TGACTCAGTC TCCAGCCATC

CTGTCTGTGA GTCCAGGAGA GAGAGTCAGT

TTTTCCTGCA GGACCAGTCA GAGCATTGGC

ACAAACATAC ACTGGTATCA GCAAAGAACA

AATGGTTTTC CAAGGCTTCT CATAAAGAAT

-continued

GTTTCTGAGT CTATCTCTGG GATCCCTTCC

AGGTTTAGTG GCAGTGGATC AGGGACAGAT

TTTATTCTTA GCATCAACAG TGTGGAGTCT

GAAGATATTG CAGATTATTA TTGTCAACAA

AGTAATACCT GGCCGTTCAC GTTCGGAGGG

GGGACCAAGC TGGAAATAAA A.

The methods of the invention also encompass polynucleotides that hybridize under various stringency, e.g., high stringency, intermediate or lower stringency conditions, to polynucleotides that encode a Fc RIIB or CD20 antibody of the combination of the invention. The hybridization can be performed under various conditions of stringency. By way of example and not limitation, procedures using conditions of low stringency are as follows (see also Shilo et al. (1981) "*DNA Sequences Homologous To Vertebrate Oncogenes Are Conserved In Drosophila Melanogaster,*" Proc. Natl. Acad. Sci. U.S.A 78, 6789 6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 mg/ml denatured salmon sperm DNA. Hybridizations are carried out in the same solution with the following modifications: 0.02% PVP, 0.02% Ficoll, 0.2% BSA, 100 mg/ml salmon sperm DNA, 10% (wt/vol) dextran sulfate, and 5–20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 mg/ml denatured salmon sperm DNA. Filters are hybridized for 48 h at 65° C. in prehybridization mixture containing 100 mg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, MOLECULAR CLONING, A LABORATORY MANUAL, 2d Ed., Cold Spring Harbor Laboratory Press, Cold Spring Harbor, N.Y.; see also, Ausubel et al., eds., CURRENT PROTOCOLS IN MOLECULAR BIOLOGY series of laboratory technique manuals, 1987-1997, Current Protocols, 1994-1997 John Wiley and Sons, Inc.; see especially, Dyson, 1991, "*Immobilization of nucleic acids and hybridization analysis,*" In: ESSENTIAL MOLECULAR BIOLOGY: A PRACTICAL APPROACH, Vol. 2, T. A. Brown, ed., pp. 111-156, IRL Press at Oxford University Press, Oxford, UK).

The polynucleotides may be obtained, and the nucleotide sequence of the polynucleotides determined, by any method known in the art.

A polynucleotide encoding an antibody may be generated from nucleic acid from a suitable source (e.g., a cDNA library generated from, or nucleic acid, preferably poly A+ RNA, isolated from, any tissue or cells expressing the antibody, such as hybridoma cells selected to express an antibody of the invention, e.g., 2B6, 3H7 or 8B5.3.4) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1989, MOLECULAR CLONING, A LABORATORY MANUAL, 2d Ed., Cold Spring Harbor Laboratory Press, Cold Spring Harbor, N.Y.; see also, Ausubel et al., eds., CURRENT PROTOCOLS IN MOLECULAR BIOLOGY series of laboratory technique manuals, 1987-1997, Current Protocols, 1994-1997 John Wiley and Sons, Inc.; which are both incorporated by reference herein in their entireties), to generate antibodies having a different amino acid sequence, for example to create amino acid substitutions, deletions, and/or insertions In a specific embodiment, one or more of the CDRs are inserted within framework regions using routine recombinant DNA techniques. The framework regions may be naturally occurring or consensus framework regions, and preferably human framework regions (see, e.g., Chothia et al. (1998) "*Structural Determinants In The Sequences Of Immunoglobulin Variable Domain*," J. Mol. Biol. 278: 457-479 for a listing of human framework regions). Preferably, the polynucleotide generated by the combination of the framework regions and CDRs encodes an antibody that specifically binds to FcγRIIB with greater affinity than said antibody binds FcγRIIA. Preferably, as discussed supra, one or more amino acid substitutions may be made within the framework regions, and, preferably, the amino acid substitutions improve binding of the antibodies of the invention to FcγRIIB or CD20. Representative plasmids, pMGx608 (pCI-neo (Invitrogen, Inc.) containing a humanized 2B6 heavy chain with human VH1-18 and JH6 germline sequences as frameworks, 2B6 mouse CDRs and human IgG$_1$ Fc constant region) and pMGx611 (pCI-neo containing a humanized 2B6 light chain with human VK-A26 and JK4 as frameworks, human kappa as constant region, and mouse 2B6 light chain CDRs with N$_{50}$→Y and V$_{51}$→A in CDR2), having ATCC Accession numbers PTA-5963 and PTA-5964, respectively, were deposited under the provisions of the Budapest Treaty with the American Type Culture Collection (10801 University Blvd., Manassas, Va. 20110-2209) on May 7, 2004, respectively, and are incorporated herein by reference. The antibody formed by these heavy and light chains is designated h2B6YA.

In another embodiment, human libraries or any other libraries available in the art, can be screened by standard techniques known in the art, to clone the nucleic acids encoding the antibodies of the invention.

J. Recombinant Expression of Antibodies

Once a nucleic acid sequence encoding an antibody of the combinations of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al., 1989, MOLECULAR CLONING, A LABORATORY MANUAL, 2d Ed., Cold Spring Harbor Laboratory Press, Cold Spring Harbor, N.Y.; see also, Ausubel et al., eds., CURRENT PROTOCOLS IN MOLECULAR BIOLOGY series of laboratory technique manuals, 1987-1997, Current Protocols, 1994-1997 John Wiley and Sons, Inc.).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibodies of the combinations of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al. (1998) "*Powerful And Versatile Enhancer-Promoter Unit For Mammalian Expression Vectors*," Gene 45:101-105; Cockett et al. (1990) "*High Level Expression Of Tissue Inhibitor Of Metalloproteinases In Chinese Hamster Ovary Cells Using Glutamine Synthetase Gene Amplification*," Biotechnology 8:662-667).

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al. (1983) "*Easy Identification Of cDNA Clones*," EMBO J. 2:1791-1794), in which the antibody coding sequence may be ligated individually into the vector in frame with the lac Z coding region so that a fusion protein is produced; pIN vectors (Inouye et al. (1985) "*Up-Promoter Mutations In The Lpp Gene Of Escherichia coli*," Nucleic Acids Res. 13:3101-3110; Van Heeke et al. (1989) "*Expression Of Human Asparagine Synthetase In Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "*Adenovirus Tripartite Leader Sequence Enhances Translation Of mRNAs Late After Infection*," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "*Expression And Secretion Vectors For Yeast*," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "*Transfer Of Purified Herpes Virus Thymidine Kinase Gene To Cultured Mouse Cells*," Cell 11:223-232), hypoxanthine-guanine phosphoribosyltransferase (Szybalska et al. (1962) "*Genetics Of Human Cess Line. IV. DNA-Mediated Heritable Transformation Of A Biochemical Trait*," Proc. Natl. Acad. Sci. USA 48:2026-2034), and adenine phosphoribosyltransferase (Lowy et al. (1980) "*Isolation Of Transforming DNA: Cloning The Hamster aprt Gene*," Cell 22:817-823) genes can be employed in tk–, hgprt– or aprt– cells, respectively. Also, antimetabolite resistance can be used as the basis of selection for the following genes: dhfr, which confers resistance to methotrexate (Wigler et al. (1980) "*Transformation Of Mammalian Cells With An Amplifiable Dominant-Acting Gene*," Proc. Natl. Acad. Sci. USA 77:3567-3570; O'Hare et al. (1981) "*Transformation Of Mouse Fibroblasts To Methotrexate Resistance By A Recombinant Plasmid Expressing A Prokaryotic Dihydrofolate Reductase*," Proc. Natl. Acad. Sci. USA 78:1527-1531); gpt, which confers resistance to mycophenolic acid (Mulligan et al. (1981) "*Selection For Animal Cells That Express The Escherichia coli Gene Coding For Xanthine-Guanine Phosphoribosyltransferase*," Proc. Natl. Acad. Sci. USA 78:2072-2076); neo, which confers resistance to the aminoglycoside G-418 (Tachibana et al. (1991) "*Altered Reactivity Of Immunoglobulin Produced By Human-Human Hybridoma Cells Transfected By pSV2-Neo Gene*," Cytotechnology 6(3):219-226; Tolstoshev (1993) "*Gene Therapy, Concepts, Current Trials And Future Directions*," Ann. Rev. Pharmacol. Toxicol. 32:573-596; Mulligan (1993) "*The Basic Science Of Gene Therapy*," Science 260:926-932; and Morgan et al. (1993) "*Human Gene Therapy*," Ann. Rev. Biochem. 62:191-217). Methods commonly known in the art of recombinant DNA technology which can be used are described in Ausubel et al., eds, 1994, CURRENT PROTOCOLS IN MOLECULAR BIOLOGY, Vol. 1, John Wiley & Sons, Inc., New York; Kriegler, 1990, GENE TRANS- FER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY.; Colbere-Garapin et al. (1981) "*A New Dominant Hybrid Selective Marker For Higher Eukaryotic Cells*," J. Mol. Biol. 150:1-14; and hygro, which confers resistance to hygromycin (Santerre et al. (1984) "*Expression Of Prokaryotic Genes For Hygromycin B And G418 Resistance As Dominant-Selection Markers In Mouse L Cells*," Gene 30:147-156).

The expression levels of an antibody of the invention can be increased by vector amplification (for a review, see Bebbington and Hentschel, "*The use of vectors based on gene amplification for the expression of cloned genes in mammalian cells*," in DNA CLONING, Vol. 3. (Academic Press, New York, 1987). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "*Expression And Amplification Of Engineered Mouse Dihydrofolate Reductase Minigenes*," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "*Expression And Amplification Of Engineered Mouse Dihydrofolate Reductase Minigenes*," Nature 322:562-565; Kohler (1980) "*Immunoglobulin Chain Loss In Hybridoma Lines,*" Proc. Natl. Acad. Sci. USA 77:2197-2199). The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

K. Prophylactic And Therapeutic Methods

Cancer.

The combinations of antibodies of the invention can be used to prevent, inhibit or reduce the growth of primary tumors or metastasis of cancerous cells that express or are related to the expression or over-expression of CD20. In a specific embodiment, the combination of an antibody of the invention inhibits or reduces the growth of primary tumor or metastasis of cancerous cells by at least 99%, least 60%, at least 50%, at least 45%, at least 40%, at least 45%, at least 35%, at least 30%, at least 25%, at least 20%, or at least 10% relative to the growth of primary tumor or metastasis in absence of said antibody of the invention. In a preferred embodiment, the combination of antibodies of the invention inhibit or reduce the growth of primary tumor or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibodies.

The transition from a normal to a malignant state is a multistep process involving genetic and epigenetic changes. In fact, numerous alterations occur in the cellular regulatory circuits that facilitate this progression which enables tumor cells to evade the commitment to terminal differentiation and quiescence that normally regulate tissue homeostasis. Certain genes have been implicated in invasiveness and metastatic potential of cancer cells such as CSF-1 (colony stimulating factor 1 or macrophage colony stimulating factor). Although not intending to be bound by a particular mechanism of action, CSF-1 may mediate tumor progression and metastasis by recruiting macrophages to the tumor site where they promote progression of tumor. It is believed that macrophages have a trophic role in mediating tumor progression and metastasis perhaps by the secretion of angiogenic factors, e.g., thymidine phosphorylase, vascular endothelial-derived growth factor; secretion of growth factors such as epidermal growth factor that could act as a paracrine factor on tumor cells, and thus promoting tumor cell migration and invasion into blood vessels. (See, e.g., Lin et al. (2001) "*Colony-Stimulating Factor* 1 *Promotes Progression Of Mammary Tumors To Malignancy*," J. Exp. Med. 193(6): 727-739; Lin et al. (2002) "*The Macrophage Growth Factor Csf-*1 *In Mammary Gland Development And Tumor Progression*," Journal of Mammary Gland Biology and Neoplasm 7(2): 147-162; Scholl et al. (1993) "*Is Colony-Stimulating Factor-*1 *A Key Mediator Of Breast Cancer Invasion And Metastasis?*" Molecular Carcinogenesis, 7: 207-211; Clynes et al. (2000) "*Inhibitory Fc Receptors Modulate In Vivo Cytoxicity Against Tumor Targets*," Nature Medicine, 6(4): 443-446; Fidler et al. (1985) "*Macrophages And Metastasis—A Biological Approach To Cancer Therapy*," Cancer Research, 45: 4714-4726).

The present invention encompasses therapies which involve administering (A) an anti-FcγRIIB antibody or fragment thereof, and (B) an anti-CD20 antibody or a fragment thereof to an animal, preferably a mammal, and most preferably a human, to prevent, treat, manage or ameliorate CD20-associated cancers or tumors, such as a B cell malignancy, or one or more symptoms thereof. This combination therapy has a synergistic effect over either single antibody (e.g., Fc RIIB antibody or CD20 antibody) therapy alone and are an enhancement over other current therapies. In certain cases, patients who are refractory to current therapies can be treated with the combinations of the invention. In some embodiments, therapy by administration of a combination of the invention is further combined with administration of one or more other therapies such as, but not limited to, chemotherapies, radiation therapies, hormonal therapies, and/or biological therapies/immunotherapies.

The present invention encompasses treatment protocols that provide better prophylactic and therapeutic profiles than current single agent therapies or current combination therapies for a B cell malignancy, or one or more symptoms thereof. The invention provides FcγRIIB- and CD20 antibody-based therapies for the prevention, treatment, management, or amelioration of a CD20-associated cancer or tumor, such as a B cell malignancy, or one or more symptoms thereof. In particular, the invention provides prophylactic and therapeutic protocols for the prevention, treatment, management, or amelioration of a CD20-associated cancer or tumor, such as a B cell malignancy, or one or more symptoms thereof, comprising the administration of a FcγRIIB-specific antibody and an anti-CD20 antibody, or an analog, derivative or an antigen-fragment thereof, to a subject in need thereof.

The combinations of the invention are useful for treating or preventing any CD20-associated cancer or tumor, such as any B cell malignancies, particularly non-Hodgkin's lymphoma and chronic lymphocytic leukemia. Other B cell malignancies include small lymphocytic lymphoma, Burkitt's lymphoma, mantle cell lymphomas diffuse small cleaved cell lymphomas, most follicular lymphomas and some diffuse large B cell lymphomas (DLBCL). FcγRIIB, is a target for deregulation by chromosomal translocation in malignant lymphoma, particularly in B cell non-Hodgkin's lymphoma (See Callanan et al. (2000) "*The IgG Fc Receptor, FcgammaRIIB, Is A Target For Deregulation By Chromosomal Translocation In Malignant Lymphoma*," Proc. Natl. Acad. Sci. U.S.A., 97(1):309-314). Thus, the combinations of antibodies of the invention are useful for treating or preventing any chronic lymphocytic leukemia of the B cell lineage. Chronic lymphocytic leukemia of the B cell lineage are reviewed by Freedman (See review by Freedman (1990) "*Immunobiology Of Chronic Lymphocytic Leukemia*," Hemtaol. Oncol. Clin. North Am. 4:405-429). Although not intending to be bound by any mechanism of action, the agonistic antibodies of the invention inhibit or prevent CD20-associated cancers or tumors, such as B cell malignancies, by inhibiting B cell proliferation and/or activation. The invention also encompasses the use of the combinations of the invention in combination with other therapies known (e.g., chemotherapy and radiotherapy) in the art for the prevention and/or treatment of CD20-associated cancers or tumors, such as B cell malignancies. The invention also encompasses the use of the combinations of the invention in combination with other antibodies known in the art for the treatment and or prevention of CD20-associated cancers or tumors, such as B cell malignancies.

Autoimmune and Inflammatory Diseases.

The combinations of a CD20 antibody and a Fc RIIB antibody of the invention may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically effective amount of a combination of the invention comprising a CD20 antibody or fragment thereof and a Fc RIIB antibody or fragment thereof. The invention also provides methods for preventing, treating, or managing one or more symptoms associated with an inflammatory disorder in a subject, further comprising administering to said subject a therapeutically effective amount of one or more anti-inflammatory agents. The invention also provides methods for preventing, treating, or managing one or more symptoms associated with an autoimmune disease, further comprising administering to said subject a therapeutically effective amount of one or more immunomodulatory agents. Non-limiting examples of anti-inflammatory agents and immunomodulatory agents that can be administered simultaneously or sequentially with the combinations of the invention are provided elsewhere herein.

The anti-FcγRIIB and anti-CD20 antibodies of the invention can also be used in combination with any of the antibodies known in the art for the treatment and/or prevention of autoimmune disease or inflammatory disease. A non-limiting example of the antibodies or Fc fusion proteins that can be used for the treatment or prevention of inflammatory disorders and autoimmune disorders is presented in Tables 6A and 6B, respectively, of U.S. Pat. No. 7,355,008, which is herein incorporated by reference. The antibodies of the invention can for example, enhance the efficacy of treatment of the therapeutic antibodies or Fc fusion proteins presented in the above-referenced Tables 6A and 6B. For example, but not by way of limitation, the antibodies of the invention can enhance the immune response in the subject being treated with any of the antibodies or Fc fusion proteins in the above-referenced Tables 6A or 6B.

The combinations of the invention can also be used in conjunction with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of autoimmune or inflammatory disorders (Weeratna et al. (2001) "*CpG ODN Can Re-Direct The Th Bias Of Established Th2 Immune Responses In Adult And Young Mice*," FEMS Immunol Med. Microbiol., 32(1):65-71, which is incorporated herein by reference).

Examples of autoimmune disorders that may be treated by administering the FcγRIIB antibody and CD20 antibody combinations of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described elsewhere herein, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In certain embodiments of the invention, the FcγRIIB antibody and CD20 antibody combinations of the invention may be used to treat an autoimmune disease that is more prevalent in one sex. For example, the prevalence of Graves' disease in women has been associated with expression of Fc RIIB2 (see Estienne et al. (2002) "*Androgen-Dependent Expression Of Fc{gamma}RIIB2 By Thyrocytes From Patients With Autoimmune Graves' Disease: A Possible Molecular Clue For Sex Dependence Of Autoimmune Disease*," FASEB J. 16:1087-1092).

FcγRIIB antibody and CD20 antibody combinations of the invention of the invention can also be used to reduce the inflammation experienced by animals, particularly mammals, preferably humans with inflammatory disorders. In a specific embodiment, an antibody reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in the not administered said antibody. In another embodiment, a combination of antibodies reduce the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said antibodies.

Immunomodulatory and Anti-Inflammatory Agents.

The method of the present invention provides methods of treatment for autoimmune diseases and inflammatory diseases comprising administration of a combination of an FcγRIIB antibody and a CD20 antibody in conjunction with other treatment agents. Examples of immunomodulatory agents include, but are not limited to, methothrexate, ENBREL®, REMICADE™, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™) fenoprofen (NALFON™), indomethacin (INDOCIN™), ketoralac (TORADOL™), oxaprozin (DAYPRO™), nabumetone (RELAFEN™), sulindac (CLINORIL™) tolmentin (TOLECTIN™), rofecoxib (VIOXX™), naproxen (ALEVE™ NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes. The combinations of the invention may be administered to a subject simultaneously or sequentially with any of the above-referenced immunomodulatory agents.

Therapeutic Antibodies and Anti-Cancer Agents.

In a specific embodiment, the methods of the invention encompass the administration of one or more angiogenesis inhibitors in conjunction with the combinations of the invention, such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); EGFr blockers/inhibitors (IRESSA®, TARCEVA®, ERBITUX®, and ABX-EGF); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-); Vasculostatin; Vasostatin (calreticulin fragment); ZD6126; ZD 6474; farnesyl transferase inhibitors (FTI); and bisphosphonates. The combinations of the invention may be administered to a subject simultaneously or sequentially with any of the above-referenced angiogenesis inhibitors.

Anti-cancer agents that can be used in conjunction with the combinations of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixinab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. The combinations of the invention may be administered to a subject simultaneously or sequentially with any of the above-referenced anti-cancer agents.

L. Compositions and Methods of Administering

The invention provides methods and pharmaceutical compositions comprising anti-FcγRIIB and anti-CD20 antibody combinations of the invention. The invention also provides methods of treatment, prophylaxis, and amelioration of one or more symptoms associated with a disease, disorder or infection by administering to a subject an effective amount of a combination of the invention, or a pharmaceutical composition comprising a combination of the invention. In a preferred aspect, one or more of the antibodies in the combination is substantially purified (i.e., substantially free from substances that limit its effect or produce undesired side-effects), and preferably all of the antibodies in the combination are substantially purified. In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising the combination of antibodies of the invention, e.g., encapsulation in liposomes, microparticles, microcapsules, recombinant cells capable of expressing the antibody or fusion protein, receptor-mediated endocytosis (See, e.g., Wu et al. (1987) "Receptor-Mediated In Vitro Gene Transformation By A Soluble DNA Carrier System," J. Biol. Chem. 262:4429-4432), construction of a nucleic acid as part of a retroviral or other vector, etc.

In some embodiments, the antibodies of the combination of the invention are formulated in liposomes for targeted delivery of the antibodies of the invention. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Eppstein et al. (1985) "Biological Activity Of Liposome-Encapsulated Murine Interferon Gamma Is Mediated By A Cell Membrane Receptor," Proc. Natl. Acad. Sci. USA, 82: 3688-3692; Hwang et al. (1980) "Hepatic Uptake And Degradation Of Unilamellar Sphingomyelin/Cholesterol Liposomes: A Kinetic Study," Proc. Natl. Acad. Sci. USA, 77: 4030-4034; U.S. Pat. Nos. 4,485,045 and 4,544,545; all of which are incorporated herein by reference in their entirety.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome see, e.g., Bendas et al. (2001) "Immunoliposomes: A Promising Approach To Targeting Cancer Therapy," BioDrugs, 15(4): 215-224; Allen et al. (1987) "Large Unilamellar Liposomes With Low Uptake Into The Reticuloendothelial System," FEBS Lett. 223: 42-46; Klibanov et al. (1990) "Amphipathic Polyethyleneglycols Effectively Prolong The Circulation Time Of Liposomes," FEBS Lett., 268: 235-237; Blume et al. (1990) "Liposomes For The Sustained Drug Release In Vivo," Biochim. Biophys. Acta., 1029: 91-97; Torchilin. et al. (1996) "How Do Polymers Prolong Circulation Time Of Liposomes?," J. Liposome Res. 6: 99-116; Litzinger et al. (1994) "Effect Of Liposome Size On The Circulation Time And Intraorgan Distribution Of Amphipathic Poly(Ethylene Glycol)-Containing Liposomes," Biochim. Biophys. Acta, 1190: 99-107; Maruyama et al. (1991) "Effect Of Molecular Weight In Amphipathic Polyethyleneglycol On Prolonging The Circulation Time Of Large Unilamellar Liposomes," Chem. Pharm. Bull., 39: 1620-1622; Klibanov et al. (1991) "Activity Of Amphipathic Poly(Ethylene Glycol) 5000 To Prolong The Circulation Time Of Liposomes Depends On The Liposome Size And Is Unfavorable For Immunoliposome Binding To Target," Biochim Biophys Acta, 1062; 142-148; Allen et al. (1994) "The Use Of Glycolipids And Hydrophilic Polymers In Avoiding Rapid Uptake Of Liposomes By The Mononuclear Phagocyte System," Adv. Drug Deliv. Rev., 13: 285-309; all of which are incorporated herein by reference in their entirety. The invention also encompasses liposomes that are adapted for specific organ targeting, see, e.g., U.S. Pat. No. 4,544,545, or specific cell targeting, see, e.g., U.S. Patent Application Publication No. 2005-0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al. (1982) "*Irreversible Coupling Of Immunoglobulin Fragments To Preformed Vesicles. An Improved Method For Liposome Targeting*," J. Biol. Chem. 257: 286-288, which is incorporated herein by reference in its entirety.

The combinations of antibodies of the invention can also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, STEALTH LIPOSOMES, Boca Rotan: CRC Press, 233-44; Hansen et al. (1995) "*Attachment Of Antibodies To Sterically Stabilized Liposomes Evaluation, Comparison And Optimization Of Coupling Procedures*," Biochim. Biophys. Acta, 1239: 133-144; which are incorporated herein by reference in their entirety. In most preferred embodiments, immunoliposomes for use in the methods and compositions of the invention are further sterically stabilized. Preferably, the combinations of antibodies of the invention are linked covalently or non-covalently to a hydrophobic anchor, which is stably rooted in the lipid bilayer of the liposome. Examples of hydrophobic anchors include but are not limited to phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., GENE THERAPY: ADVANCES IN PHARMACOLOGY, Volume 40, Academic Press, San Diego, Calif., p. 399-435, which is incorporated herein by reference in its entirety. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors such as pyridylthiopropionyl-phosphatidylethanolamine See, e.g., Dietrich et al. (1996) "*Functional Immobilization Of A DNA-Binding Protein At A Membrane Interface Via Histidine Tag And Synthetic Chelator Lipids*," Biochemistry, 35: 1100-1105; Loughrey et al. (1987) "*A Non-Covalent Method Of Attaching Antibodies To Liposomes*," Biochim. Biophys. Acta, 901: 157-160; Martin et al. (1982) "*Irreversible Coupling Of Immunoglobulin Fragments To Preformed Vesicles. An Improved Method For Liposome Targeting*," J. Biol. Chem. 257: 286-288; Martin et al. (1981) "*Immunospecific Targeting Of Liposomes To Cells: A Novel And Efficient Method For Covalent Attachment Of Fab' Fragments Via Disulfide Bonds*," Biochemistry, 20: 4429-4438; all of which are incorporated herein by reference in their entirety. Although not intending to be bound by a particular mechanism of action, immunoliposomal formulations comprising an antibody or antibodies of the combination of the invention are particularly effective as therapeutic agents, since they deliver the antibody to the cytoplasm of the target cell, i.e., the cell comprising the Fc RIIB receptor and/or CD20 to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The invention encompasses immunoliposomes comprising antibodies of the combination of the invention or a fragment thereof. In some embodiments, the immunoliposomes further comprise one or more additional therapeutic agents, such as those disclosed herein.

The immunoliposomal compositions of the invention comprise one or more vesicle forming lipids, an antibody of the invention or a fragment or derivative thereof, and optionally a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and ganglioside GM1, which increases the serum half life of the liposome. Methods of conjugating hydrophilic polymers to liposomes are well known in the art and encompassed within the invention. For a review of immunoliposomes and methods of preparing them, see, e.g., U.S. Patent Application Publication No. 2003-0044407; PCT International Publication No. WO 97/38731, Vingerhoeads et al. (1994) "*Immunoliposomes In Vivo*," Immunomethods, 4: 259-272; Maruyama (2000) "*In Vivo Targeting By Liposomes*," Biol. Pharm. Bull. 23(7): 791-799; Abra et al. (2002) "*The Next Generation Of Liposome Delivery Systems: Recent Experience With Tumor-Targeted, Sterically-Stabilized Immunoliposomes And Active-Loading Gradients*," Journal J. Liposome Research, Res. 12 (1 &2): 1-3; Park (2002) "*Tumor-Directed Targeting Of Liposomes*," Bioscience Reports, 22(2): 267-281; Bendas et al. (2001) "*Immunoliposomes: A Promising Approach To Targeting Cancer Therapy*," BioDrugs, 14(4): 215-224; Bendas et al. (2001) "*Immunoliposomes: A Promising Approach To Targeting Cancer Therapy*," BioDrugs, 15(4): 215-224, J. Thomas August, ed., GENE THERAPY: ADVANCES IN PHARMACOLOGY, Volume 40, Academic Press, San Diego, Calif., p. 399-435, all of which are incorporated herein by reference in their entireties.

Methods of administering the combinations of antibodies of the invention include, but are not limited to, parenteral administration (e.g., intradermal, intramuscular, intraperitoneal, intravenous and subcutaneous), epidural, and mucosal (e.g., intranasal and oral routes). In a specific embodiment, the combinations of antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985, 309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the antibodies of the combinations of the invention are packaged in a hermetically sealed container, such as an ampoule or sachette indicating the quantity of antibody. In some embodiments, the FcγRIIB antibody of the combination is packaged in the same sealed container as the CD20 antibody. In other embodiments, the FcγRIIB antibody and CD20 antibody are packaged in different or separate sealed containers. In one embodiment, the antibodies of the invention are supplied as a dry sterilized lyophilized powder or water-free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. In one embodiment, a FcγRIIB antibody is supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg in the same hermetically sealed container as a CD20 antibody supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg. In another embodiment, a FcγRIIB antibody is supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg in a different hermetically sealed container as a CD20 antibody supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2° C. and 8° C. in their original container and the antibodies should be administered within 12 hours, preferably within 6 hours, within 5 hours, within 3 hours, or within 1 hour after being reconstituted.

In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the antibodies. In one embodiment, a FcγRIIB antibody is supplied as a liquid form at least 5 mg, more preferably at least 10 mg, at least 15 mg, at least 25 mg, at least 35 mg, at least 45 mg, at least 50 mg, or at least 75 mg in the same hermetically sealed container as a CD20 antibody supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg. In another embodiment, a FcγRIIB antibody is supplied as a liquid form at least 5 mg, more preferably at least 10 mg, at least 15 mg, at least 25 mg, at least 35 mg, at least 45 mg, at least 50 mg, or at least 75 mg in a different hermetically sealed container as a CD20 antibody supplied as a sterile lyophilized powder at a unit dosage of at least 5 mg, more preferably at least 10 mg, at least 15 mg, at least 25 mg, at least 35 mg, at least 45 mg, at least 50 mg, or at least 75 mg.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight independently for each antibody in the combination. Preferably, the dosage of each antibody administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of each of the antibodies of the combinations of the invention administered to a patient are 0.01 mg to 1000 mg/day. In another embodiment the antibodies of the invention are used in combination with other therapeutic compositions and the dosage administered to a patient are lower than when said combination of antibodies are used alone.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the combination of the invention, care must be taken to use materials to which the antibody does not absorb.

In another embodiment, the compositions can be delivered in a vesicle, in particular a liposome (See Langer (1990) "*New Methods Of Drug Delivery*," Science 249:1527-1533; Treat et al., in LIPOSOMES IN THE THERAPY OF INFECTIOUS DISEASE AND CANCER, Lopez-Berestein and Fidler (eds.), Liss, New York, pp. 317-327 and 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising one or more antibodies of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting of Long-Circulating Emulsions*," PDA Journal of Pharmaceutical Science & Technology 50:372-397; Cleek et al. (1997) "*Biodegradable Polymeric Carriers for a bFGF Antibody for Cardiovascular Application*," Pro. Int'l. Symp. Control. Rel. Bioact. Mater. 24:853-854; and Lam et al. (1997) "*Microencapsulation of Recombinant Humanized*

*Monoclonal Antibody for Local Delivery,*" Proc. Int'l. Symp. Control Rel. Bioact. Mater. 24:759-760, each of which is incorporated herein by reference in its entirety. In one embodiment, a pump may be used in a controlled release system (See Langer, supra; Sefton (1987) "*Implantable Pumps,*" CRC Crit. Ref. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis,*" Surgery 88:507-516; and Saudek et al. (1989) "*A Preliminary Trial Of The Programmable Implantable Medication System For Insulin Delivery,*" N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); "*Controlled Drug Bioavailability,*" DRUG PRODUCT DESIGN AND PERFORMANCE, Smolen and Ball (eds.), Wiley, New York (1984); Ranger et al. (1983) "Ranger et al. (1983) "*Chemical And Physical Structure Of Polymers as Carriers For Controlled Release Of Bioactive Agents: A Review,*" J. Macromol. Sci. Rev. Macromol. Chem. 23:61-126; See also Levy et al. (1985) "*Inhibition Of Calcification Of Bioprosthetic Heart Valves By Local Controlled-Release Diphosphonate,*" Science 228:190-192; During et al. (1989) "*Controlled Release Of Dopamine From A Polymeric Brain Implant: In Vivo Characterization,*" Ann. Neurol. 25:351-356; Howard et al. (1989) "*Intracerebral Drug Delivery In Rats With Lesion-Induced Memory Deficits,*" J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990) "*New Methods Of Drug Delivery,*" Science 249:1527-1533. Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel,*" Radiotherapy & Oncology 39:179-189, Song et al. (1995) "*Antibody Mediated Lung Targeting of Long-Circulating Emulsions,*" PDA Journal of Pharmaceutical Science & Technology 50:372-397; Cleek et al. (1997) "*Biodegradable Polymeric Carriers for a bFGF Antibody for Cardiovascular Application,*" Pro. Int'l. Symp. Control. Rel. Bioact. Mater. 24:853-854; and Lam et al. (1997) "*Microencapsulation of Recombinant Humanized Monoclonal Antibody for Local Delivery,*" Proc. Int'l. Symp. Control Rel. Bioact. Mater. 24:759-760, each of which is incorporated herein by reference in its entirety.

In a specific embodiment where the composition of the invention comprises one or more nucleic acids encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis,*" Proc. Natl. Acad. Sci. USA 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight for each antibody in the combination. Preferably, the dosage of each antibody of the combination administered to a subject is between 0.1 mg/kg and 20 mg/kg of the subject's body weight and more preferably the dosage of each antibody of the combination administered to a subject is between 1 mg/kg to 10 mg/kg of the subject's body weight. The dosage and frequency of administration of the combination antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of the combination antibodies of the invention can include a single treatment or, preferably, can include a series of treatments. In a preferred example, a subject is treated with combinations of antibodies of the invention in the range of between about 0.1 to 30 mg/kg body weight of each antibody of the combination, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

M. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of antibodies of the invention and a pharmaceutically acceptable carrier.

In one particular embodiment, the pharmaceutical composition comprises of a therapeutically effective amount of (A) an antibody or a fragment thereof that binds FcγRIIB with a greater affinity than said antibody or a fragment thereof binds FcγRIIA, (B) an anti-CD20 antibody, and (C) a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The present invention also provides pharmaceutical compositions and kits comprising a FcγRIIB antagonist and anti-CD20 agent for use in the prevention, treatment, management, or amelioration of a B cell malignancy, or one or more symptoms thereof. In particular, the present invention provides pharmaceutical compositions and kits comprising a FcγRIIB antagonist, an analog, derivative or an anti-FcγRIIB antibody or an antigen-binding fragment thereof and a CD20 antibody or fragment thereof.

In various embodiments, a CD20 antibody or fragment thereof and a FcγRIIB antibody or fragment thereof of the combination of the invention, and optionally in further combination with other prophylactic or therapeutic agents, can be administered simultaneously or less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of disease, the route of administration, as well as age, body weight, response, and the past medical history of the patient. Suitable regimens can be selected by one skilled in the art by considering such factors and by following, for example, dosages reported in the literature and recommended in the PHYSICIAN'S DESK REFERENCE ($56^{th}$ ed., 2002).

The combinations of antibodies of this invention may also be advantageously utilized in combination with other monoclonal or chimeric antibodies, Fc fusion proteins, or with lymphokines, cytokines or hematopoietic growth factors (such as, e.g., IL-2, IL-3, IL-4, IL-7, IL-10 and TGF-), which enhance Fc RIIB and/or CD20, for example, serve to increase the number or activity of effector cells which interact with the antibodies and, increase immune response. In certain embodiments, a cytokine is conjugated to an anti-FcγRIIB antibody and/or CD20 antibody of the combinations.

The antibodies of the combinations of this invention may also be advantageously utilized in combination with one or more drugs used to treat a disease, disorder, or infection such as, for example anti-cancer agents or anti-inflammatory agents, e.g., as detailed elsewhere herein.

N. Kits

The invention provides a pharmaceutical pack or kit comprising one or more containers filled with FcγRIIB-specific antibodies and CD20-specific antibodies. The FcγRIIB antibodies and CD20 antibodies can be in the same or different containers in the pharmaceutical pack or kit. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more FcγRIIB-specific antibodies and a CD20 antibody or fragment thereof. In another embodiment, a kit further comprises one or more other prophylactic or therapeutic agents useful for the treatment of CD20-associated disease in one or more containers.

O. Characterization and Demonstration of Therapeutic Utility

Several aspects of the pharmaceutical compositions or prophylactic or therapeutic agents of the invention are preferably tested in vitro, e.g., in a cell culture system, and then in vivo, e.g., in an animal model organism, such as a rodent animal model system, for the desired therapeutic activity prior to use in humans. For example, assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed, e.g., inhibition of or decrease in growth and/or colony formation in soft agar or tubular network formation in three-dimensional basement membrane or extracellular matrix preparation. The tissue sample can be obtained by biopsy from the patient. This test allows the identification of the therapeutically most effective prophylactic or therapeutic molecule(s) for each individual patient. Alternatively, instead of culturing cells from a patient, therapeutic agents and methods may be screened using cells of a tumor or malignant cell line. In various specific embodiments, in vitro assays can be carried out with representative cells of cell types involved in an autoimmune or inflammatory disorder (e.g., T cells), to determine if a pharmaceutical composition of the invention has a desired effect upon such cell types. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc. Additional assays include raft association, CDC, ADCC and apoptosis assays as known in the art and described in the Examples.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Preferred animal models for use in the methods of the invention are for example, transgenic mice expressing Fc R on mouse effector cells, e.g., any mouse model described in U.S. Pat. No. 5,877,396 (which is incorporated herein by reference in its entirety). Transgenic mice for use in the methods of the invention include but are not limited to mice carrying human Fc RIIIA, mice carrying human Fc RIIA, mice carrying human Fc RIIB and human Fc RIIIA, mice carrying human Fc RIIB and human Fc RITA.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The anti-inflammatory activity of the combination therapies of invention can be determined by using various experimental animal models of inflammatory arthritis known in the art and described in Crofford L. J. and Wilder R. L., "*Arthritis and Autoimmunity in Animals*", in ARTHRITIS AND ALLIED CONDITIONS: A TEXTBOOK OF RHEUMATOLOGY, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principal animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "*Arthritis and Autoimmunity in Animals*", in ARTHRITIS AND ALLIED CONDITIONS: A TEXTBOOK OF RHEUMATOLOGY, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al. (2000) "*Carrageenan-Induced Arthritis in the Rat*," Inflammation, 24(2): 141-155. Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al. (1962) "*Carrageenan-Induced Edema in Hind Paw of the Rat as an Assay for Anti-inflammatory Drugs*" Proc. Soc. Exp. Biol Med. 111, 544-547. This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al. (1992) "*Experimental Colitis in Animal Models*," Scand. J. Gastroentrol. 27:529-537; Strober (1985) "*Animal Models Of Inflammatory Bowel Disease—An Overview*," Dig. Dis. Sci. 30(12 Suppl):3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al. (1997) "*Induction of Airway Mucus Production By T Helper 2 (Th2) Cells: A Critical Role For Interleukin 4 In Cell Recruitment But Not Mucus Production*," J. Exp. Med. 186:1737-1747).

Animal models for autoimmune disorders can also be used to assess the efficacy of the combination therapies of invention. Animal models for autoimmune disorders such as type 1 diabetes, thyroid autoimmunity, systemic lupus erythematosus, and glomerulonephritis have been developed (Flanders et al. (1999) "*Prevention Of Type 1 Diabetes From Laboratory To Public Health*," Autoimmunity 29:235-246; Krogh et al. (1999) "*Models To Study The Pathogenesis Of Thyroid Autoimmunity*," Biochimie 81:511-515; Foster (1999) "*Relevance Of Systemic Lupus Erythematosus Nephritis Animal Models To Human Disease*," Semin. Nephrol. 19:12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the combination therapies and optional prophylactic and/or therapeutic agents for use in humans. The dosage lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the combination therapies used in accordance with the present invention also can be determined by using various experimental animal models for the study of cancer such as the SCID mouse model or transgenic mice or nude mice with human xenografts, animal models, such as hamsters, rabbits, etc., known in the art and described in RELEVANCE OF TUMOR MODELS FOR ANTICANCER DRUG DEVELOPMENT (1999, eds. Fiebig and Burger); CONTRIBUTIONS TO ONCOLOGY (1999, Karger); THE NUDE MOUSE IN ONCOLOGY RESEARCH (1991, eds. Bowen and Winograd); and ANTICANCER DRUG DEVELOPMENT GUIDE (1997 ed. Teicher), herein incorporated by reference in their entireties.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

EXAMPLE 1

Characterization of Monoclonal Anti-FcγRIIB Antibodies

Monoclonal anti-FcγRIIB Antibodies and CD20 co-stain Human B Lymphocytes. A double staining FACS assay was used to characterize the antibody produced from clones 2B6 and 3H7 in human B lymphocytes. Cells were stained with anti-CD20 antibody which was FITC conjugated, to select the B-lymphocyte population, as well as the antibodies produced from clone 3H7 and 2B6, labeled with goat anti-mouse peroxidase. The horizontal axis represents the intensity of the anti-CD20 antibody fluorescence and the vertical axis represents the intensity of the monoclonal antibody fluorescence. As shown in FIGS. 1B and 1C, cells are double stained with the anti-CD20 antibody as well as the antibodies produced from clones 2B6 and 3H7, however, the antibody produced from clone 2B6 shows more intense staining than that produced from clone 3H7. FIG. 1A shows the staining of the isotype control, mouse IgG1.

Effect of Ch2B6 Antibodies on Tumor Growth. Balb/c Nude female mice (Taconic, Md.) were injected at day 0 with 5×10$^6$ Daudi cells subcutaneously. Mice (5 mice per group) also received i.p. injection of PBS (negative control), 10 g/g ch4.4.20 (anti-FITC antibody, negative control), 10 g/g RITUXAN® (positive control) or 10 g/g ch2B6 once a week starting at day 0. Mice were observed twice a week following injection and tumor size (length and width) was determined using a caliper. Tumor size in mg was estimated using the formula: (length×width)/2.

Figure 2:
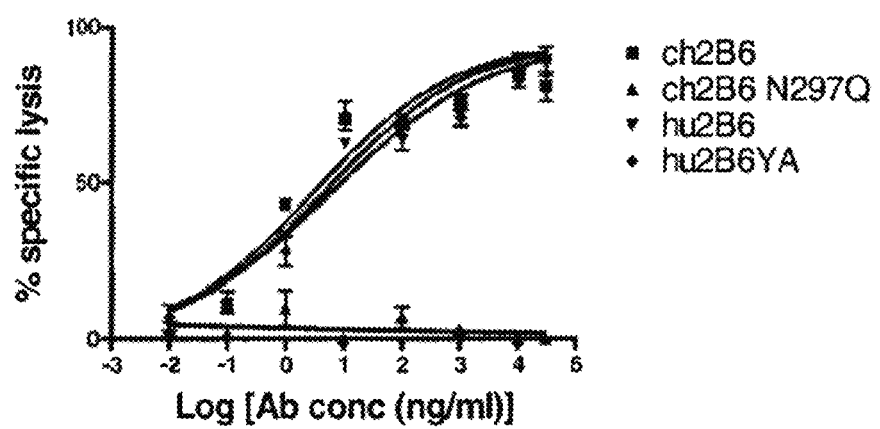
FIG. 2: Estimated tumor size in individual mice. Injection days are indicated by arrows.

Results. As shown in FIG. 2, Daudi cells form subcutaneous tumors in Balb/c nude females starting around day 21 post tumor cell injection. At day 35, subcutaneous tumors were detected in mice receiving PBS (5 mice out of 5) or 10 g/g ch4.4.20 (5 mice out of 5). Tumors were rarely detected in mice receiving 10 g/g RITUXAN® (1 mouse out of 5) and were not detected in mice receiving 10 g/g ch2B6 (0 mice out of 5).

Effect of 2B6 Variants on Tumor Growth in a Murine Xenograft Model. Eight week old Balb/c FoxN1 female mice (Taconic, Germantown, N.Y.) were injected subcutaneously at day 0 with $5 \times 10^6$ Daudi cells as well as intraperitoneally with 2B6 antibody variants (ch2B6, chN297Q, h2B6, h2B6YA, h2B6YA 31/60, h2B6YA 38/60, h2B6YA 55/60, or h2B6 YA 71 at 2.5 g, 7.5 g, or 25 g), Rituximab (positive control at 2.5 g, 7.5 g, 25 g, or 250 g) or PBS (negative control). Mice were then treated with antibodies or PBS once a week until day 42 (total of 7 injections) and tumor size was measured twice a week using a caliper. Tumor weight was estimated using the formula: (width2× length)/2.

Figure 3G:
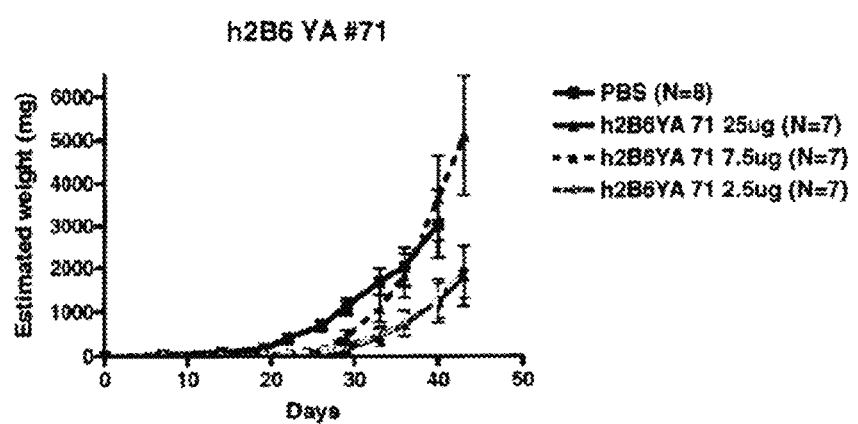
Figures 4A, 4B, 4C, 4D:
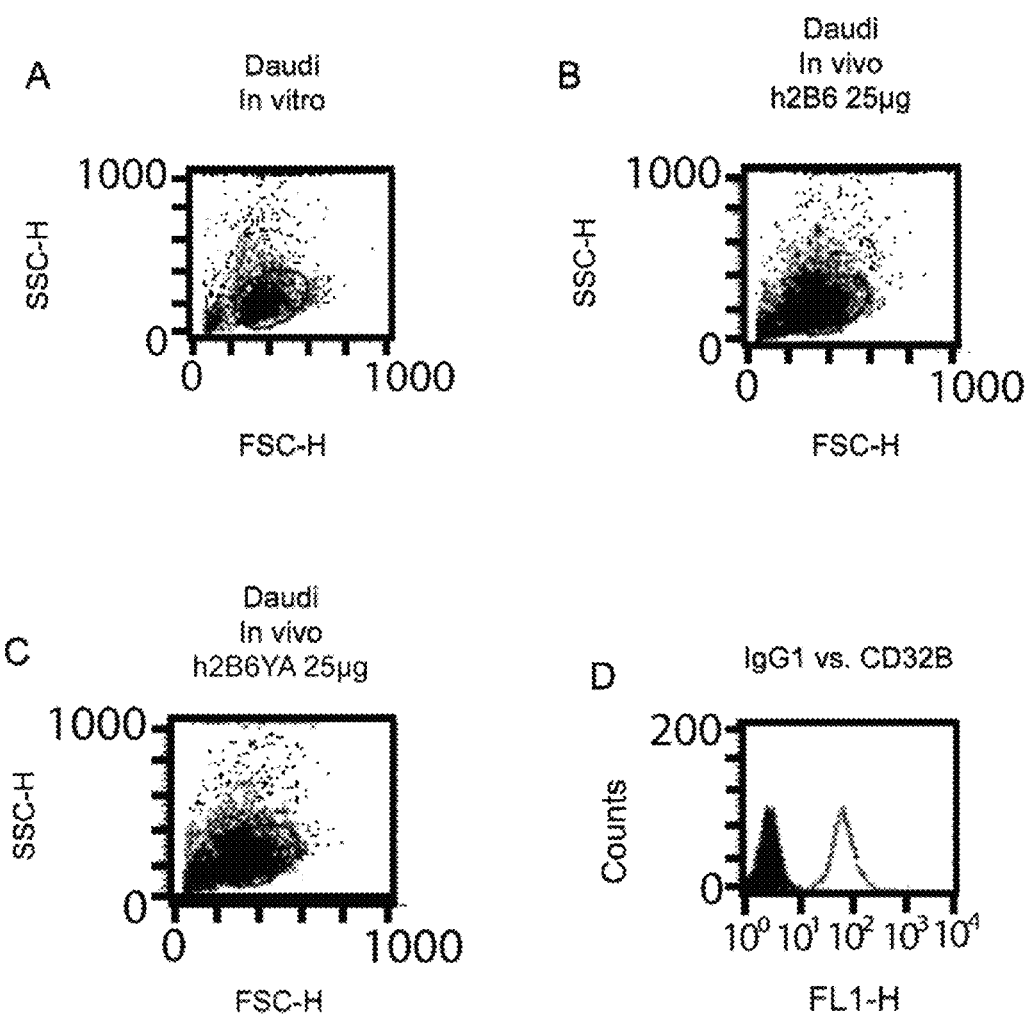

Results. To evaluate the efficacy of anti-CD32B mAb variants in the prevention of tumor cell growth in vivo, Balb/c FoxN1 mice were simultaneously injected with Daudi cells and anti-CD32B mAb variants (FIGS. 3A-G). Treatment with the positive control, Rituximab, significantly reduced tumor cell growth in a dose dependent fashion (FIG. 3A). Three different variants of anti-CD32B mAb 2B6 (chimeric 2B6 (ch2B6), humanized 2B6 (h2B6), and a variant in the Fv region (h2B6YA)) were all effective at slowing tumor growth (FIG. 3B). The h2B6YA variant showed a remarkable reduction in tumor growth at a dose of 2.5 g (0.1 g/gm). The same dose of Rituximab was not as effective at preventing tumor growth. Four different h2B6YA mAb variants with Fc mutations (h2B6YA 31/60, h2B6YA 38/60, h2B6YA 55/60, and h2B6YA 71) were analyzed to determine if anti-tumor activity in vivo could be improved. Mutants h2B6YA 31/60, h2B6YA 38/60, and h2B6YA 55/60 functioned as well or better than h2B6YA, which contained a wild type Fc (FIGS. 3C, 3D, 3E, and 3F). Mutant h2B6YA 71 showed dose independent activity (FIG. 3G). Tumor cell growth was slowed at doses of 2.5 g and 25 g; however, little or no effect on tumor growth was noted at the 7.5 g dose (FIG. 3G).

These results demonstrate that h2B6YA 31/60 and h2B6YA 55/60 have improved in vivo anti-tumor activity compared to ch2B6 or h2B6YA.

Ex Vivo Staining of Daudi for CD20 and CD32B. Daudi tumors were collected from mice treated with h2B6 or h2B6YA at 25 g. CD20 and CD32B expression was compared with those of Daudi cell expanded in vitro. FACS analysis was performed as described below.

As shown in FIGS. 4A-4I, cells expanded in vivo maintain CD20 and CD32B expression even after anti-CD32B treatment.

EXAMPLE 2

Expression of CD32B on B-CLL Cells

The ability of CD32B-specific antibodies to react with CD32B on cells isolated from patients with B-CLL was tested by staining isolated cells in FACS analysis.

Protocol for isolating B cells from patients. Mononuclear leukocytes from peripheral blood leukocytes from normal donors and B cell neoplasia patients were isolated by using Ficoll-Paque PLUS (Amesrham Pharmacia Biotech) gradient centrifugation and cryopreserved in aliquots in liquid nitrogen. An aliquot of freshly isolated PBMCs from each patient was washed in PBS containing 10% human serum and analyzed immediately for CD32B expression by standard FACS analysis. Single-cell suspension from lymph node biopsy specimens will be prepared in similar manner, will be immediately analyzed, and will be cryopreserved in liquid nitrogen.

Two cytospin slides were obtained from each samples and one stained immediately with May-Grunwald Giemsa (MGG) for morphological evaluation. Prior to analysis, an aliquot of patient's cells was thawed, the viability evaluated upon thawing and, if necessary (viability upon recovery<80%), subjected to Ficoll-Paque PLUS centrifugation. The amount of tumor cells was estimated by clonality by using anti-kappa or lambda chain antibodies in FACS analysis. Leukocyte phenotyping was performed by using directed conjugated anti-CD3, CD20, CD56, CD14, and CD16 antibodies and proper FSC and SCC gating. B-CLL B cells were further analyzed for CD5, CD23, CD25, CD27, CD38, CD69, and CD71 (Damle et al. (2002) "*B-Cell Chronic Lymphocytic Leukemia Cells Express A Surface Membrane Phenotype Of Activated, Antigen-Experienced B Lymphocytes,*" Blood 99:4087-4093; Chiorazzi et al. (2003) "*B Cell Chronic Lymphocytic Leukemia: Lessons Learned From Studies Of The B Cell Antigen Receptor,*" Ann Rev Immunol 21:841-894). Computerized logs were maintained recording the number of vials, number of cells per vial, and cell viability before and after cryopreservation, number of tumor cells or leukocyte phenotype.

Protocol for FACS analysis. Cells were incubated with the anti-CD32B monoclonal antibody, 2B6, followed by a secondary (Cy5 conjugated) goat-anti mouse $(Fab)_2$ fragment antibody. After washes, FITC or PE-conjugated lineage-specific antibodies (anti-CD3, CD 19, CD 20 and CD5) were added and the samples were analyzed by using FACSCalibur in a two-color format. CD3-positive cells (T cells) are used as an internal control as they do not express CD32B and do not react with 2B6 antibody. CD20, CD19 and CD5 antibodies identify B cell lineage sub-populations. Preliminary studies were conducted in >10 healthy human subjects to calibrate the amount of individual anti-CD32B antibodies based on the reactivity with the donor's B cells identified by CD20-positivity. For each antibody, the smallest amount of antibody that gave 100% reactivity and the highest MCF value in titration experiments was selected for subsequent use.

Figure 5:
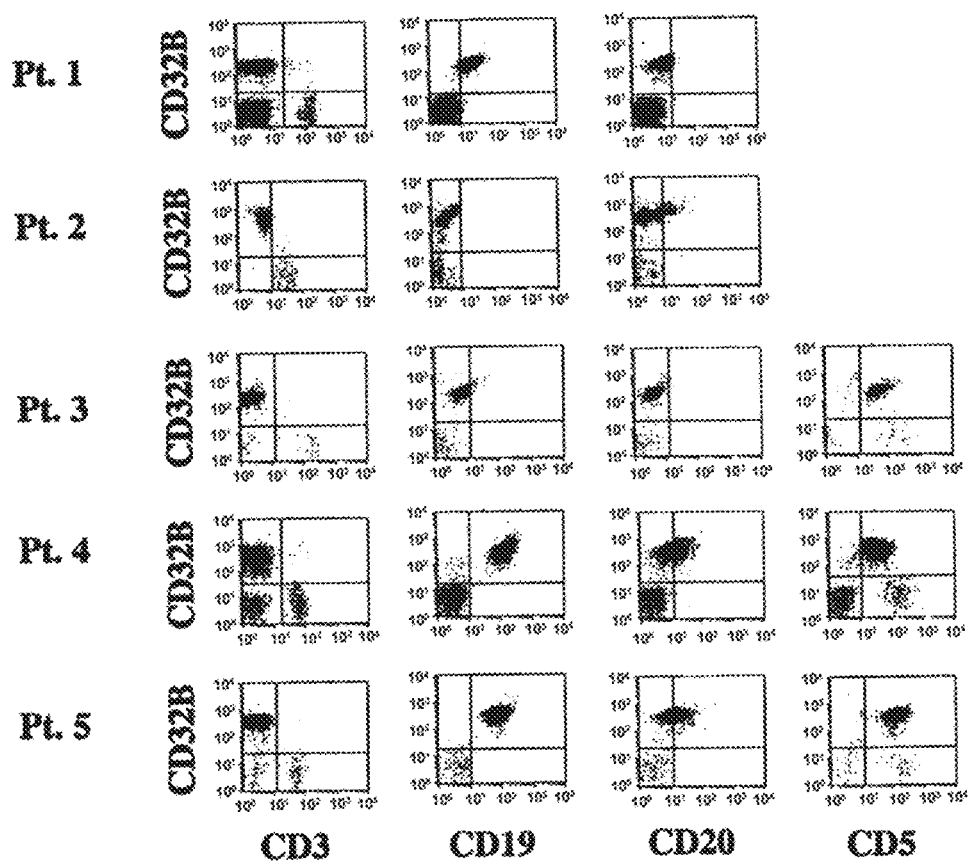
FIG. 5: Expression of surface membrane markers on B-CLL cells from five different patients. PBMCs from patients diagnosed with B-CLL were isolated by using Ficoll-Paque density gradient centrifugation and analyzed for expression of CD32B together with CD3, CD19, CD20 or CD5 (last three patients). Cells were stained using 2B6 antibody to detect CD32B followed by F(ab)'2 fragments of Cy5-labeled goat anti mouse IgG, and CD3, and counterstained with directly FITC or PE-labeled mouse antibodies against CD19, CD20, or CD5. Stained cells were analyzed by FACSCalibur (Becton Dickinson).

Results: As shown in FIG. 5, B cells isolated from B-CLL patients stained intensely with anti-CD32B antibodies. Cells from all five patients are consistently CD32B-positive being reactive with 2B6 antibody, but express B cell-lineage markers only to various degrees. The results indicate that CD32B is expressed on B cells isolated from patients with B-CLL.

EXAMPLE 3

Expression of CD32B in Lymph Nodes from Patients with Non-Hodgkin's Lymphoma

To investigate expression of CD32B in lymph nodes from patients with non-Hodgkin's lymphomas, histological analysis and immunohistochemistry was performed on a series of lymphatic tissues from patients with a confirmed diagnosis of B cell neoplasia based on histological and FACS analysis criteria.

Tissue specimens. Frozen lymph nodes were obtained from the Cooperative Human Tissue Network (CHTN), Mid-Atlantic Division (Charlottesville, Va.). The tissue was received in dry ice, and upon arrival sectioned in two portions, one for histopathological analysis of the tumor and the other portion for Immunohistochemistry analysis.

Histopathological analysis and Immunohistochemistry. All eleven cases were fixed in 10% Neutral Buffered Formalin (NBF) and paraffinized in a tissue processor (Miles Scientific). After paraffinization, tissue blocks were sectioned with a Leica Microtome (Leica Microsystems, Bannockburn, Ill.) at 5 microns. The sections were placed in slides, deparaffinized with xylene and proceeded with an Hematoxylin and Eosin (H-E) tissue staining protocol (Luna, Histopathologic methods and Color Atlas Of Special Stains and Tissue Artifacts 1992 American Histolabs, Inc., Publications Division, Kolb Center, 7605-F Airpark Road, Gaithersburg, Md. 2087. Daudi B cells, a malignant cell line involved in B cell lymphomas, were used as positive controls. Normal tonsil and lymph nodes were used as additional controls to understand the distribution of the cells expressing CD20 and CD32B in normal tissues.

The remaining portions of these samples were placed in cryomolds and embedded in OCT cryocompound (Tissue-Tek). Once the blocks were ready, each was sectioned under a Cryostat (Leica Microsystems) at 6 microns. The slides were placed in 4° C. acetone and fixed for 10 minutes. Hours after fixation the slides were air dried and washed with phosphate buffer saline (PBS). Then endogenous peroxide activity was blocked by a 30 minute incubation in a 0.3% hydrogen peroxide solution. The slides were washed in PBS and incubated for 30 minutes with 10% normal goat serum in 2% normal human serum. After this step, the slides were divided in two groups. Two monoclonal antibodies were utilize and incubated on the same tissue in parallel, an anti-CD20 (1F5—a hybridoma, ATCC No. HB-9645, purified at Macrogenics) and the murine monoclonal anti-CD32B antibody, 2B6. Each group was incubated with one monoclonal antibody and their respective Isotype control, IgG1 (BD Biosciences, San Jose, Calif.) for the 2B6/anti-CD32B group and IgG2a (BD Biosciences) for the 1F5/anti-CD20 group. Mouse IgG1 and murine IgG2a were used as Isotype controls for anti-CD32B and anti-CD20, respectively. After one hour of incubation at room temperature, the slides were washed in PBS and incubated with a secondary antibody Goat anti Mouse labeled peroxidase (Jackson ImmunoResearch Laboratories, West Grove, Pa.). After washing with PBS, the sections were incubated in amino-9-ethylcarbazol (AEC) and hydrogen peroxide (Koretz et al. (1987) "*Metachromasia Of 3-Amino-9-Ethylcarbazole (Aec) And Its Prevention In Immunoperoxidase Techniques*," Histochemistry 86:471-478). Hematoxylin was used as a counterstain.

The expression of anti CD20 and CD32B was scored under a light microscope at low power magnification based on the following criteria: a score of zero (−) meant no detectable reactivity; a score of plus/minus (+/−) meant detectable reaction in 1-10% of the cells; one plus (+) was equivalent to 10-30% positive cells; two pluses (++) for tissue with positive cells ranging from 30-70%; and three pluses (+++) for those tissues where 70% to 100% were positive.

Figure 6:
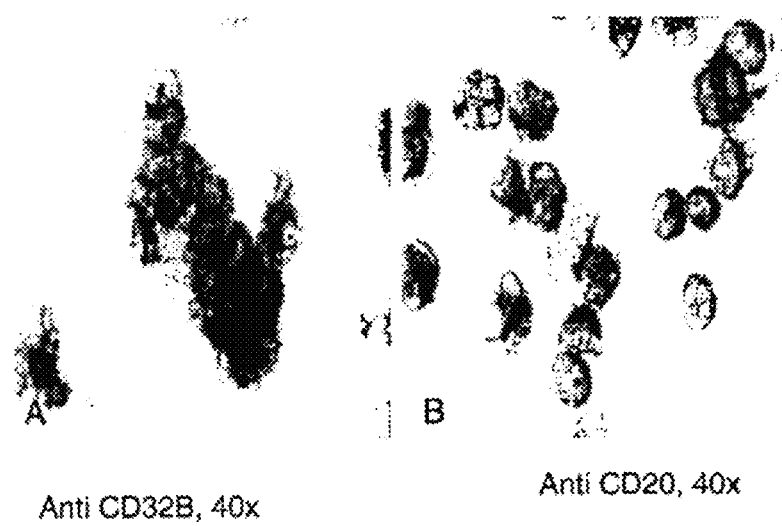
FIGS. 6A-6B: Immunohistochemical staining of Daudi B Cells.
Figure 7A:
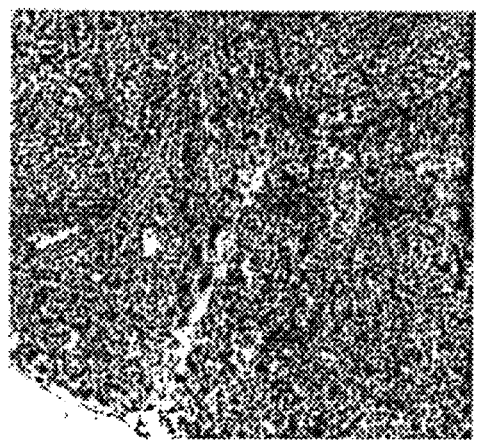
FIGS. 7A-7C: Immunohistochemical staining of normal tonsil tissue.
Figure 7B:
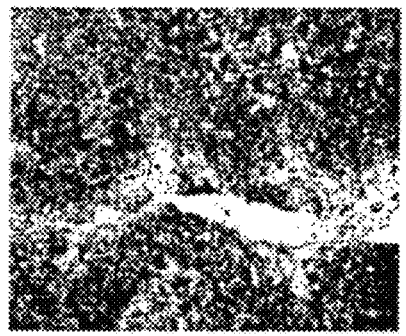
Figure 7C:
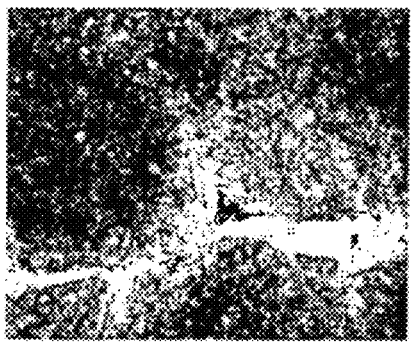
Figure 8A:
FIGS. 8A-8C: Immunohistochemical staining of normal lymph nodes.
Figure 8B:
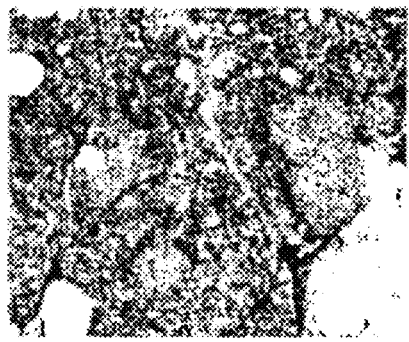
Figure 8C:
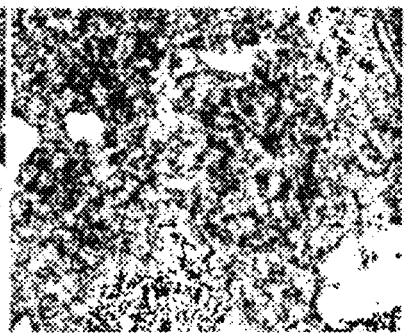

Results. Both positive controls, i.e., a malignant cell line involved in B cell lymphomas (Daudi cells; FIGS. 6A-6B) and normal tissues known to contain lymphatic tissue (tonsil: FIGS. 7A-7C; lymph nodes: FIGS. 8A-8C), responded positively to anti-Cd32B and anti-CD20 antibodies by immunohistochemistry. Normal tonsil tissues and lymph nodes stain differently with anti-CD32B antibodies and anti-CD20 antibodies. Lymphatic follicles showing germinal centers react with anti-CD20, while the cells in the follicles surrounding germinal centers react with anti-CD32B. Thus, morphological differences can be detected by immunohistochemistry with these two antibodies.

A total of ten lymph nodes and one spleen (11 cases) obtained from CHTN were analyzed. The results are summarized in Table 4.

TABLE 4

Summary of Immunohistochemistry Results

| Patient Code | Final Pathologic Diagnosis | Tissue | 2B6 | 1F5 |
| --- | --- | --- | --- | --- |
| MG04-CHTN-19 | Diffuse Large B Cell Lymphoma | Lymph Node | ++ | ++ |
| MG04-CHTN-22 | Diffuse Large B Cell Lymphoma | Lymph Node | ++ | +/− |
| MG04-CHTN-26 | Follicular Lymphoma With areas of Diffuse Large B cell Lymphoma | Lymph Node | + | ++ |
| MG04-CHTN-27 | Diffuse Large B Cell Lymphoma | Lymph Node | +++ | + |
| MG05-CHTN-03 | Diffuse Small Lymphocytic Lymphoma with Plasmacytoid features | Lymph Node | +++ | +/− |
| MG05-CHTN-05 | Diffuse Large B Cell Lymphoma | Lymph Node | + | ++ |
| MG04-CHTN-30 | Small Lymphocytic Lymphoma | Lymph Node | − | − |
| MG04-CHTN-31 | Diffuse Large B Cell Lymphoma | Lymph Node | ++ | + |
| MG04-CHTN-36 | Diffuse Large B Cell Lymphoma | Spleen | +++ | ++ |
| MG04-CHTN-41 | Mantle Cell Lymphoma/Diffuse Small Cleaved Cell Lymphoma | Lymph Node | ++ | +/− |
| MG04-CHTN-05 | Diffuse Large B Cell Lymphoma | Lymph Node | − | − |

Eight cases were Diffuse Large B Cell Lymphomas, two were Small Lymphocytic Lymphomas, and one was Mantle Cell Lymphoma/Diffuse Small Cleaved Cell Lymphoma. In the small lymphocytic lymphoma category, one had plasmacytoid features. All hematoxylin and eosin (H&E)-stained slides were reviewed for confirmation of the diagnosis.

The expression of CD20 was negative in 18% of the cases and weakly positive in ~30%, and intermediate/strongly positive in the remaining 50% of the cases. CD32B was detected in 80% of the cases and was found to be negative in only two cases.

CD32B expression was detected on 80% of NHL test cases. Expression of CD32B was often detected in more cells than CD20 was detected. CD32B may be a useful target of treatment of NHL.

EXAMPLE 4

In Vivo Tumor Clearance Studies in Murine Tumor Xenograft Models of Lymphomas

The ability to prevent tumors in a mouse model of lymphoma is an important criterion to determine the potential for an antibody to proceed into clinical studies.

A number of well characterized Burkitt's lymphoma cell lines are available for use as models of NHL (Epstein et al. (1966) "Morphological And Virological Investigations On Cultured Burkitt Tumor Lymphoblasts (Strain Raji)," J Natl Cancer Inst 37:547-559; Klein et al. (1968) "Surface IgM-Kappa Specificity On A Burkitt Lymphoma Cell In Vivo And In Derived Culture Lines," Cancer Res. 28: 1300-1310; Klein et al. (1975) "An EBV-Genome-Negative Cell Line Established From An American Burkitt Lymphoma; Receptor Characteristics. EBV Infectibility And Permanent Conversion Into Ebv-Positive Sublines By In Vitro Infection," Intervirology 5:319-334; Nilsson et al. (1977) "Tumorigenicity Of Human Hematopoietic Cell Lines In Athymic Nude Mice," Intl J Cancer 19:337-344; Ohsugi et al. (1980) "Tumorigenicity Of Human Malignant Lymphoblasts: Comparative Study With Unmanipulated Nude Mice, Antilymphocyte Serum-Treated Nude Mice, And X-Irradiated Nude Mice," J Natl Cancer Inst 65:715-718). A xenograft model of lymphoma formation has been established in nude mice similar to previously reported models (Vallera et al. (2003) "Preclinical Studies Targeting Normal And Leukemic Hematopoietic Cells With Yttrium-90-Labeled Anti-CD45 Antibody In Vitro And In Vivo In Nude Mice," Cancer Biother Radiopharm 18:133-145; Vuist et al. (1989) "Potentiation By Interleukin 2 Of Burkitt's Lymphoma Therapy With Anti-Pan B (anti-CD19) Monoclonal Antibodies In A Mouse Xenotransplantation Model," Cancer Res 49:3783-3788).

In brief, the Burkitt's lymophoma cell line, Daudi (5–10× $10^6$ cells), was transplanted subcutaneously into an immunodeficient nu/nu mouse strain. The BALB/c nu/nu mouse strain was used together with adoptively transferred human PBMC purified from a healthy donor as effector cells. A prevailing effector cell population in human PBMC is represented by NK cells, which exert ADCC via their CD16A (FcγRIIIa). A nu/nu mouse strain in which the murine CD16A gene has been knocked out and which has been genetically engineered to express human CD16A was also be used. This CD16A−/− huCD16Atg, nu/nu mouse allowed for the examination of anti-tumor activity in the context of a human Fc receptor without the need for the adoptive transfer of human cells. Synergism of combination therapy with a CD20 antibody and a FcγRIIB antibody were studied.

Mice were treated with a CD20 antibody (rituximab; hereafter in this Example and FIGS. 9-10, "CD20 Ab"), an FcγRIIB antibody comprising a VH chain as depicted in SEQ ID NO:70 and a VL chain as depicted in SEQ ID NO:66 (hereafter in this Example and FIGS. 9-10, "FcgRIIB Ab"), or a combination of CD20 Ab and FcγRIIB Ab injected i.p. on days 1, 4, 7, and 15 at a dose of 30 µg/g of body weight or 1 µg/g of body weight. Palivizumab (SYNAGIS®, MedImmune) an irrelevant anti-RSV antibody, as well as PBS alone were used as a negative control.

In these studies, tumor growth and morbidity were monitored to compare antibody treated and control groups. Mice were sacrificed immediately if moribund or at the completion of the studies. The tumors was then be excised and gross and microscopic necropsy performed. Cytopathology on paraffin-embedded sections and immunohistochemistry on frozen sections was also performed for a morphological and immunological evaluation of the tumor and cellular infiltrates.

As can be seen in FIG. 9A, the PBS and palivizumab negative controls resulted in a continuous increase in tumor volume over the course of the study, as did treatment with the 30 µg/g body weight of the CD20 Ab antibody alone. The FcγRIIB Ab at a 30 µg/g body weight dose resulted in a decrease of tumor volume as compared to the negative controls. However, it was surprisingly discovered that a combination of a 30 µg/g body weight dose of FcγRIIB Ab+CD20 Ab resulted in a significant drop in tumor weight over the course of the study. The FcγRIIB Ab+CD20 Ab combination was synergistic and reduced the tumor volume more dramatically than either antibody alone. Similarly, FIG. 9B shows that the synergistic combination of FcγRIIB Ab+CD20 Ab resulted in 100% (complete (CR)+partial (PR)) responders by day 21. In contrast, FcγRIIB Ab or CD20 Ab alone resulted in percentage of (complete+partial) responders that was nearly the same as the negative control groups (25%-50%).

While the synergistic decrease observed in the FcγRIIB Ab+CD20 Ab group took a longer time to achieve, the same trends were seen in the animals that received a 30-fold decrease in dose (1 µg/g body weight) (FIG. 10A). FIG. 10B shows that the FcγRIIB Ab+CD20 Ab combination therapy resulted in 100% (complete+partial) responders was achieved by day 49 and was maintained throughout the course of the study. In contrast, the maximum (complete+partial) responders percentage was between 25% and 50% in each of the other groups, except the combination therapy group, which took several days longer to achieve.

Thus, the results of this study shows that a combination of anti-FcγRIIB antibody and a anti-CD20 antibody work synergistically to reduce tumor size, and the response is long-lasting.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. A method for treating a B cell malignancy in a subject, said method comprising administering to a subject in need thereof a pharmaceutical composition comprising:
   (A) an effective amount of a first isolated antibody, or an antigen-binding fragment thereof, that specifically binds the extracellular domain of native human FcγRIIB with greater affinity than said antibody or fragment thereof binds native human FcγRIIA, wherein said first antibody comprises:
      (1) a heavy chain variable domain having the amino acid sequence of SEQ ID NO: 24, SEQ ID NO: 28, SEQ ID NO: 60, or SEQ ID NO: 68; and
      (2) a light chain variable domain having the amino acid sequence of SEQ ID NO: 62;
      or
      (1) a heavy chain variable domain having the amino acid sequence of SEQ ID NO: 60 or SEQ ID NO: 68; and
      (2) a light chain variable domain having the amino acid sequence of SEQ ID NO: 18, SEQ ID NO: 20, SEQ ID NO: 22, SEQ ID NO: 26, or SEQ ID NO: 62;
   (B) an effective amount of a second isolated antibody, or an antigen-binding fragment thereof, that specifically binds human CD20; and
   (C) a pharmaceutically acceptable carrier;
   wherein said effective amounts of said first and second antibodies or said fragments thereof cause said pharmaceutical composition to mediate a synergistically reduced tumor volume relative to the tumor volume reductions mediated by:
      (1) a pharmaceutical composition comprising said effective amount of said first antibody or fragment thereof but without said second antibody or fragment thereof; and
      (2) a pharmaceutical composition comprising said effective amount of said second antibody or fragment thereof but without said first antibody or fragment thereof.

2. The method of claim 1, wherein at least one of the first antibody or the second antibody is a monoclonal antibody, a human antibody, a humanized antibody, a single chain antibody or a chimeric antibody.

3. The method of claim 1, wherein at least one of the first antibody or the second antibody further comprises an Fc domain having at least one amino acid substitution relative to the amino acid sequence of a wild-type Fc region.

4. The method of claim 3, wherein the Fc domain of the heavy chain of the first antibody and/or the second antibody comprises at least one amino acid substitution at position 240, 243, 247, 255, 270, 292, 300, 305, 316, 370, 392, 396, 416, 419, or 421 with another amino acid at that position, wherein the numbering is according to the EU index as in Kabat.

5. The method of claim 4, wherein the Fc domain of the heavy chain of the first antibody and/or the second antibody has:
   (1) a leucine at position 247, a lysine at position 421 and a glutamic acid at position 270;
   (2) a threonine at position 392, a leucine at position 396, and a glutamic acid at position 270; or
   (3) a lysine at position 255, a leucine at position 396, and a glutamic acid at position 270.

6. The method of claim 5, wherein the heavy chain further comprises an isoleucine at position 305.

7. The method of claim 4, wherein the Fc domain of the heavy chain of the first antibody and/or the second antibody has:
   (1) a leucine at position 243, a proline at position 292, a leucine at position 300, an isoleucine at position 305, and a leucine at position 396;
   (2) a leucine at position 243, a proline at position 292, a leucine at position 300, and a leucine at position 396; or
   (3) a leucine at position 243, a proline at position 292, a leucine at position 300.

8. The method of claim 1, wherein the first antibody fragment and/or the second antibody fragment is a F(ab')2 fragment or a F(ab) fragment.

9. The method of claim 1, wherein the first antibody and/or the second antibody is operably linked to a heterologous polypeptide or conjugated to a therapeutic agent.

10. The method of claim 1, wherein the first antibody reduces binding of an Ig-Fc to FcγRIIB.

11. The method of claim 1, wherein the second antibody is rituximab, 1F5 antibody (ATCC Deposit HB-9645), ibritumomab, tositumomab, or an antigen-binding fragment thereof.

12. The method of claim 1, wherein said B cell malignancy is a B cell lymphocytic leukemia or non-Hodgkin's lymphoma.

13. The method of claim 1, wherein said pharmaceutical composition further comprises one or more additional anti-cancer agents.

14. The method of claim 13, wherein said anti-cancer agent is a chemotherapeutic agent, a radiation therapeutic agent, or a hormonal therapeutic agent.

15. The method of claim 1, wherein the first antibody comprises a heavy chain variable domain having the amino acid sequence of SEQ ID NO: 68 and a light chain variable domain having the amino acid sequence of SEQ ID NO: SEQ ID NO: 62.

16. The method of claim 1, wherein said first antibody comprises a heavy chain having the amino acid sequence of SEQ ID NO: 70 and a light chain having the amino acid sequence of SEQ ID NO: 66.

\* \* \* \* \*